(12) United States Patent
Gillespie et al.

(10) Patent No.: US 7,524,870 B2
(45) Date of Patent: *Apr. 28, 2009

(54) BIARYLOXYMETHYLARENECARBOXYLIC ACIDS AS GLYCOGEN SYNTHASE ACTIVATORS

(75) Inventors: Paul Gillespie, Westfield, NJ (US); Robert Alan Goodnow, Jr., Gillette, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 381 days.

This patent is subject to a terminal disclaimer.

(21) Appl. No.: 11/283,925

(22) Filed: Nov. 21, 2005

(65) Prior Publication Data

US 2006/0122256 A1 Jun. 8, 2006

Related U.S. Application Data

(60) Provisional application No. 60/633,133, filed on Dec. 3, 2004, provisional application No. 60/715,527, filed on Sep. 9, 2005.

(51) Int. Cl.
*C07D 401/02* (2006.01)
*A61K 31/44* (2006.01)

(52) U.S. Cl. ............ 514/337; 548/146; 548/206; 546/268.1; 546/339; 514/336; 514/340; 514/365; 514/372

(58) Field of Classification Search ............ None
See application file for complete search history.

(56) References Cited

U.S. PATENT DOCUMENTS 6,214,887 B1 4/2001 Gilles et al.

FOREIGN PATENT DOCUMENTS

| DE | 28 42 243 A1 | 4/1980 |
|---|---|---|
| EP | 0 110 229 A2 | 6/1984 |
| EP | 0 299 789 A1 | 1/1989 |
| EP | 1 452 530 | 9/2004 |
| GB | 773594 | 5/1957 |
| JP | 08 333287 | 12/1996 |
| WO | WO 93/24442 A1 | 12/1993 |
| WO | WO 97/40017 A2 | 10/1997 |
| WO | WO 99/58518 A2 | 11/1999 |
| WO | WO 03/089419 A1 | 10/2003 |
| WO | WO 2004012656 A2 * | 2/2004 |
| WO | WO 2004/028634 | 4/2004 |
| WO | WO 2004/058679 | 7/2004 |
| WO | WO 2004/067524 | 8/2004 |
| WO | WO 2004/071447 A2 | 8/2004 |
| WO | WO 2005/000781 | 1/2005 |
| WO | WO 2005/123668 A1 | 12/2005 |

OTHER PUBLICATIONS

Malamas M.S., et al., J. Med. Chem., vol. 43, No. 7, pp. 1293-1310 (2000), XP002190818.
Kardas D., et al., J. Mater. Chem., vol. 11, No. 3, pp. 741-748 (2001), XP009070374.
Harris, M. I. *Diabetes Care* 1998 21 (3S) Supplement, 11C.
De Fronzo, R. A. *Drugs* 1999, 58 Suppl. 1, 29.
Inzucchi, S. E. *JAMA* 2002, 287, 360.
Turner, R. C. et al. *JAMA* 1999, 281, 2005.
Tadayyon, M. and Smith, S.A. *Expert Opin. Investig. Drugs* 2003, 12, 307.
Salas, M. and Caro, J. J. *Adv. Drug React. Tox. Rev.* 2002, 21, 205-217.
Cid, E. et al. *J. Biol. Chem.* 2000, 275, 33614.
Bai, G. et al. *J. Biol. Chem.* 1990, 265, 7843.
Browner, M. F. et al. *Proc. Nat. Acad. Sci. U. S. A.* 1989, 86, 1443.
Henry, R. R. et al. *J. Clin. Invest.* 1996, 98, 1231-1236.
Nikoulina, S. E. et al. *J. Clin. Enocrinol. Metab.* 2001, 86, 4307-4314.
Eriksson, J. et al. *N. Engl. J. Med.* 1989, 331, 337.
Schulman, R. G. et al. *N. Engl. J. Med.* 1990, 332, 223.
Thorburn, A. W. et al. *J. Clin. Invest.* 1991, 87, 489.
Orhu-Melander, M. et al. *Diabetes* 1999, 48, 918.
Lawrence, J. C., Jr. and Roach, P. J. *Diabetes* 1997, 46, 541.
Gomis, R. R. et al. *J. Biol. Chem.* 2002, 277, 23246.
Holman, G. D. and Kasuga, M. *Diabetologia* 1997, 40, 991.
Villar-Palasi, C. and Guinovart, J. J. *FASEB J.* 1997, 11, 544.
Cohen, P. *Biochem. Soc. Trans.* 1993, 21, 555.
Yeaman, S. J. *Biochem. Soc. Trans.* 2001, 29, 537.
Leloir, L. F. et al. *Arch. Biochem. Biophys.* 1959, 81, 508.
Virkamaki, A. and Yki-Jarvinen, H. *Diabetes* 1999, 48, 1101.

* cited by examiner

*Primary Examiner*—Zinna N Davis
(74) *Attorney, Agent, or Firm*—George W. Johnston; Patricia S. Rocha-Tramaloni

(57) ABSTRACT

The present invention relates to compounds of formula (I)

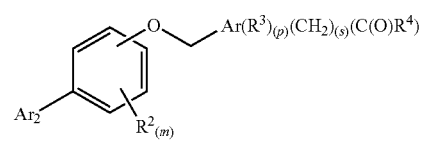

wherein Ar, $Ar_2$, $R^2$, $R^3$, $R^4$, m, p and s are as defined in the description and claims, and pharmaceutically acceptable salts thereof. The compounds are useful for the treatment and/or prophylaxis of diseases that are associated with the activation of the glycogen synthase enzyme, such as diabetes.

13 Claims, No Drawings

BIARYLOXYMETHYLARENECARBOXYLIC ACIDS AS GLYCOGEN SYNTHASE ACTIVATORS

This application claims the benefit of U.S. Provisional Application No. 60/715,527, filed Sep. 9, 2005 and U.S. Provisional Application No. 60/633,133, filed Dec. 3, 2004. The entire contents of the above-identified applications are hereby incorporated by reference.

BACKGROUND OF THE INVENTION

The present invention is concerned with novel biaryloxymethylarenecarboxylic acids and their, pharmaceutically acceptable salts, their manufacture and their use as medicaments. The present invention further relates to pharmaceutical compositions containing these compounds.

Diabetes mellitus is a common and serious disorder, affecting 10 million people in the U.S. [Harris, M. I. Diabetes Care 1998 21 (3S) Supplement, 11C], putting them at increased risk of stroke, heart disease, kidney damage, blindness, and amputation. Diabetes is characterized by decreased insulin secretion and/or an impaired ability of peripheral tissues to respond to insulin, resulting in increased plasma glucose levels. The incidence of diabetes is increasing, and the increase has been associated with increasing obesity and a sedentary life. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. However, these factors are often unable to control the disease, and there are a number of drug treaments available, including insulin, metformin, sulfonylureas, acarbose, and thiazolidinediones. Each of these treatments has disadvantages and there is an ongoing need for new drugs to treat diabetes.

Metformin is an effective agent that reduces fasting plasma glucose levels and enhances the insulin sensitivity of peripheral tissue, mainly through an increase in glycogen synthesis [De Fronzo, R. A. Drugs 1999, 58 Suppl. 1, 29]. Metformin also leads to reductions in the levels of LDL cholesterol and triglycerides [Inzucchi, S. E. JAMA 2002, 287, 360]. However, it loses its effectiveness over a period of years [Turner, R. C. et al. JAMA 1999, 281, 2005].

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [Tadayyon, M. and Smith, S. A. Expert Opin. Investig. Drugs 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [Inzucchi, S. E. JAMA 2002, 287, 360] and, like metformin, they lose efficacy over time [Turner, R. C. et al. JAMA 1999, 281, 2005]. A further problem often encountered in patients treated with sulfonylureas is hypoglycemia [Salas, M. and Caro, J. J. Adv. Drug React. Tox. Rev. 2002, 21, 205-217].

Acarbose is an inhibitor of the enzyme alpha-glucosidase which breaks down disaccharides and complex carbohydrates in the intestine. It has lower efficacy than metformin or the sulfonylureas, and it causes intestinal discomfort and diarrhea which often lead to the discontinuation of its use [Inzucchi, S. E. JAMA 2002, 287, 360].

Because none of these treatments is effective over the long term without serious side effects, there is a need for new drugs for the treatment of type 2 diabetes.

In skeletal muscle and liver, there are two major pathways of glucose utilization: glycolysis, or oxidative metabolism, where glucose is oxidized to pyruvate; and glycogenesis, or glucose storage, where glucose is stored in the polymeric form glycogen. The key step in the synthesis of glycogen is the addition of the glucose derivative UDP-glucose to the growing glycogen chain, and this step is catalyzed by the enzyme glycogen synthase [Cid, E. et al. J. Biol. Chem. 2000, 275, 33614]. There are two isoforms of glycogen synthase, found in liver [Bai, G. et al. J. Biol. Chem. 1990, 265, 7843] and in other peripheral tissues including muscle [Browner, M. F. et al. Proc. Nat Acad. Sci. U.S.A. 1989, 86, 1443]. There is clinical and genetic evidence implicating glycogen synthase in type 2 diabetes. Both basal and insulin-stimulated glycogen synthase activity in muscle cells from diabetic subjects were significantly lower than in cells from lean non-diabetic subjects [Henry, R. R. et al. J. Clin. Invest. 1996, 98, 1231-1236; Nikoulina, S. E. et al. J. Clin. Enocrinol. Metab. 2001, 86, 4307-4314]. Furthermore, several studies have shown that levels of glycogen are lower in diabetic patients than in control subjects [Eriksson, J. et al. N. Engl. J. Med. 1989, 331, 337; Schulman, R. G. et al. N. Engl. J. Med. 1990, 332, 223; Thorburn, A. W. et al. J. Clin. Invest 1991, 87, 489], and in addition, genetic studies have shown associations in several populations between type 2 diabetes and mutation in the GYS1 gene encoding the muscle isoform of glycogen synthase [Orhu-Melander, M. et al. Diabetes 1999, 48, 918].

Glycogen synthase is subject to complex regulation, involving phosphorylation at at least nine sites [Lawrence, J. C., Jr. and Roach, P. J. Diabetes 1997, 46, 541]. The dephosphorylated form of the enzyme is active. Glycogen synthase is phosphorylated by a number of enzymes of which glycogen synthase kinase 3β (GSK3β) is the best understood [Tadayyon, M. and Smith, S. A. Expert Opin. Investig. Drugs 2003, 12, 307], and glycogen synthase is dephosphorylated by protein phosphatase type I (PP1) and protein phosphatase type 2A (PP2A). In addition, glycogen synthase is regulated by an endogenous ligand, glucose-6-phosphate which allosterically stimulates the activity of glycogen synthase by causing a change in the conformation of the enzyme that renders it more susceptible to dephosphorylation by the protein phosphatases to the active form of the enzyme [Gomis, R. R. et al. J. Biol. Chem. 2002, 277, 23246].

Several mechanisms have been proposed for the effect of insulin in reducing blood glucose levels, each resulting in an increase in the storage of glucose as glycogen. First, glucose uptake is increased through recruitment of the glucose transporter GLUT4 to the plasma membrane [Holman, G. D. and Kasuga, M. Diabetologia 1997, 40, 991]. Second, there is an increase in the concentration of glucose-6-phosphate, the allosteric activator of glycogen synthase [Villar-Palasi, C. and Guinovart, J. J. FASEB J. 1997, 11, 544]. Third, a kinase cascade beginning with the tyrosine kinase activity of the insulin receptor results in the phosphorylation and inactivation of GSK3β, thereby preventing the deactivation of glycogen synthase [Cohen, P. Biochem. Soc. Trans. 1993, 21, 555; Yeaman, S. J. Biochem. Soc. Trans. 2001, 29, 537].

Because a significant decrease in the activity of glycogen synthase has been found in diabetic patients, and because of its key role in glucose utilization, the activation of the enzyme glycogen synthase holds therapeutic promise for the treatment of type 2 diabetes. The only known allosteric activators of the enzyme are glucose-6-phosphate [Leloir, L. F. et al. *Arch. Biochem. Biophys.* 1959, 81, 508] and glucosamine-6-phosphate [Virkamaki, A. and Yki-Jarvinen, H. *Diabetes* 1999, 48, 1101].

SUMMARY OF THE INVENTION

Briefly stated, novel biaryloxymethylarenecarboxylic acids have been found to be glycogen synthase activators. Consequently, the compounds of the present invention are useful for the treatment and/or prophylaxis of type 2 diabetes, and/or impaired glucose tolerance, as well as other conditions wherein the activation of the glycogen synthase enzyme gives a therapeutic benefit.

Some biaryloxymethylarenecarboxylic acids are known in the art. However, none of these known compounds have been associated with either the treatment of diseases mediated by the activation of the glycogen synthase enzyme or to any pharmaceutical composition for the treatment of diseases mediated by the activation of the glycogen synthase enzyme.

H. S. Andersen et al. WO 9740017 discloses the structure and synthetic route to 3-(biphenyl-4-yloxymethyl)-benzoic acid as an intermediate in the synthesis of SH2 inhibitors. E. Winkelmann et al. DE 2842243 discloses 5-(biphenyl-4-yloxymethyl)-thiophene-2-carboxylic acid as a hypolipemic agent.

M. M. Mjalli et al. (Transtech Pharma Inc.) PCT Int. Appl. WO 2004071447 discloses 375 compounds as inhibitors of protein tyrosine phosphatase for the treatment of diabetes. Eleven of these compounds have the following general structure.

brovascular disease, congestive heart failure, etc. or for the treatment of Alzheimer's disease. Among these patents and patent applications are the following: PCT Int. Appl. WO 9704773, U.S. Pat. No. 5,985,886, PCT Int. Appl. WO 9704781, PCT Int. Appl. WO 9704774, PCT Int. Appl. WO 9607653, US 2003004202, PCT Int. Appl. WO 9630358, PCT Int. Appl. WO 2004028634.

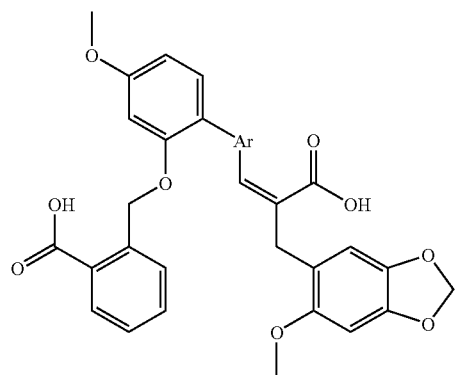

T. Inaba et al (Japan Tobacco, Inc.) PCT Int. Appl. WO 2003048140 discloses 4-[[4-[4-[(4-carboxyphenyl)methoxy]phenyl]-2-thiazolyl]methyl]-benzoic acid (CAS Number 540734-96-1) as an inhibitor of protein tyrosine phosphatase 1B

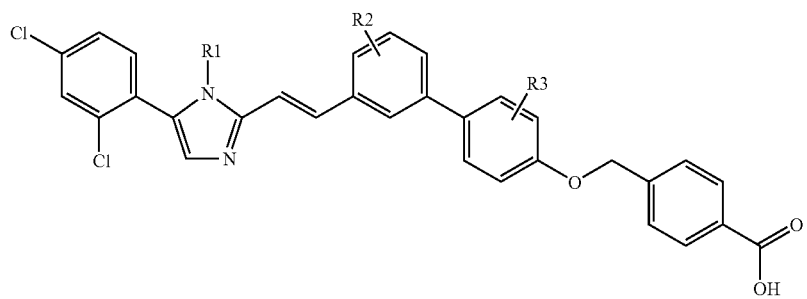

S. S. Ghosh et al. (Mitokor, Inc.) PCT Int. Appl. WO 2004058679 discloses compounds with the following general structure as ligands of adenine nucleotide translocase for the treatment of a variety of diseases including Alzheimer's disease, diabetes and obesity.

C. Braisted et al. *J. Am. Chem. Soc.* 2003, 125, 3714-3715 discloses compounds with the following general structure as IL-2 inhibitors useful for the treatment of inflammation.

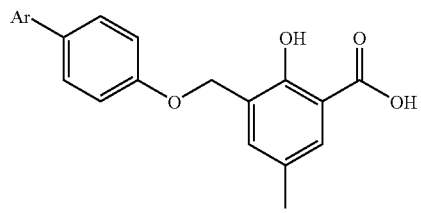

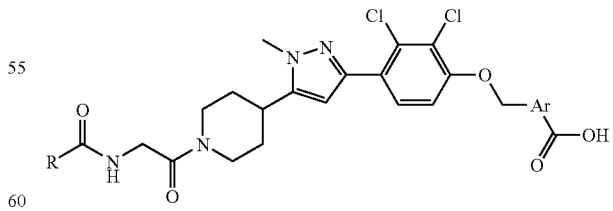

A number of patents and patent applications from Smith-Kline Beecham and The University of Illinois disclose compounds with the general structure shown below as endothelin receptor antagonists for the treatment of renal failure, cere- E. S. Priestley et al. (Bristol-Myers Squibb Company, USA) PCT Int. Appl. WO 2003026587 and H. Hashimoto et al. (Japan Tobacco, Inc.) PCT Int. Appl. WO 2003000254 disclose compounds with the following general structure for the treatment of Hepatitis C.

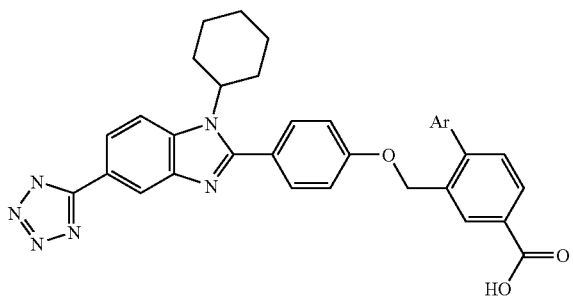

H. Shinkai et al. (Japan Tobacco Inc.) PCT Int. Appl. WO 2001027088 discloses 2-[[2-chloro-5-[5-(1,1-dimethylethyl)-1H -benzimidazol-2-yl]phenoxy]methyl]-benzoic acid (CAS Number 335014-96-5) as a lipoprotein lipase enhancer for the treatment of arteriosclerosis.

P. Lacombe et al. (Merck Frosst Canada & Co.) PCT Int. Appl. WO 2001019814 and T. P. Broten et al. (Merck Frosst Canada & Co.) PCT Int. Appl. WO 2002015902 disclose 3-[3-[2-[(4-carboxyphenyl)methoxy]-5-chlorophenyl]-2-thienyl]-benzoic acid (CAS Number 330811-34-2) and 4-[3-[2-[(4-carboxyphenyl)methoxy]-5-chlorophenyl]-2-thienyl]-benzoic acid (CAS Number 330811-33-1) for the treatment of prostaglandin-mediated diseases such as urinary incontinence.

J. Butera et al. (American Home Products Corporation) U.S. Pat. No. 6,214,877 and PCT Int. Appl. WO 9961410 disclose compounds of the following general structure as inhibitors of protein tyrosine phosphatase for the treatment of diabetes.

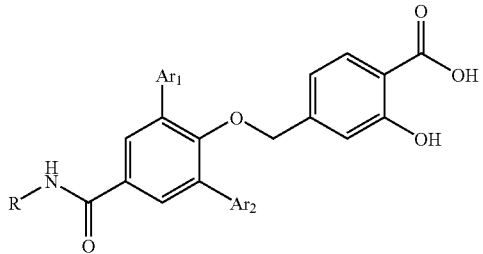

T. Mueller et al. DE 4142514 discloses 2-(biphenyl-3-yloxymethyl)-benzoic acid and 3-(biphenyl-3-yloxymethyl)-benzoic acid as fungicides.

Marfat et al. (Pfizer Inc.) U.S. Pat. No. 5,322,847 and PCT Int. Appl. WO 9117163 disclose 3-[[4-(2-methyl-1H-imidazo[4,5-c]pyridin-1-yl)phenoxy]methyl]-benzoic acid as a platelet activating factor blocker and leukotriene D4 receptor blocker useful in the treatment of illnesses including myocardial infarction and stroke.

F. J. Brown et al. *J. Med. Chem.* 1989, 32, 807-826 discloses 4-[[3-hydroxy-2-propyl-4-(2-quinolinyl)phenoxy]methyl]-3-methoxy-benzoic acid (CAS Number 118683-37-7) as a compound tested in a assay for leukotriene D4 antagonist activity.

M. Isogai et al. (Hitachi, Ltd.) Eur. Par. Appl. EP 110299 discloses 4-[[[4'-(octyloxy)[1,1'-biphenyl]4-yl]oxy]methyl]-benzoic acid as an intermediate useful in the preparation of liquid crystal compositions.

G. L. Araldi et al. (Applied Research Systems Ars Holding N.V.) PCT Int. Appl. WO 2004012656 disclose 5-[[4-(2-benzoxazolyl)phenoxy]methyl]-2-furancarboxylic acid, (CAS Number 654665-86-8), 5-[[4-(1,3,4-oxadiazol-2-yl)phenoxy]methyl]-2-furancarbox-ylic acid (CAS Number 654665-84-6), and 5-[([1,1'-biphenyl]4-yloxy)methyl]-2-furan-carboxylic acid (CAS Number 327990-68-1) as prostaglandin EP2 agonists, useful for the treatment of illnesses such as asthma, inflammatory diseases, infertility, and osteoporosis. One of these compounds, 5-[([1,1'-biphenyl]-4-yloxy)methyl]-2-furan-carboxylic acid, is commercially available from ChemDiv, Inc., San Diego, Calif., and Ambinter SARL, Paris, France.

D. E. Clark et al. (Pharmagene Laboratories Ltd.) PCT Int. Appl. WO 2004067524 disclose compounds with the following general structure as prostaglandin EP4 receptor antagonists useful for the treatment of pain, including migraine. One of these compounds (4-(biphenyl-4-yloxymethyl)-5-methyl-furan-2-carboxylic acid) is commercially available from ChemBridge Corporation, San Diego, Calif., and TimTec, Inc. Newark, Del.

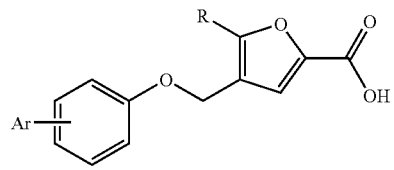

According to one aspect of the present invention, there is provided a compound of formula (I)

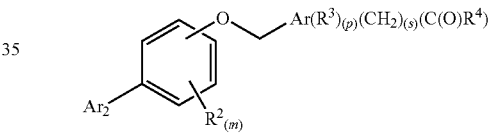

wherein Ar, $Ar_2$, $R^2$, $R^3$, $R^4$, m, p and s are as defined below.

According to another aspect of the present invention, there is provided a pharmaceutical composition comprising a compound of formula (I), or pharmaceutically acceptable salts thereof, and a pharmaceutically acceptable carrier and/or adjuvant.

According to a further aspect of the present invention, there is provided a method for treating or preventing diseases which are associated with activation of the glycogen synthase enzyme, comprising administering to a patient in need thereof, a therapeutically effective amount of a compound of formula (I).

These and other features, aspects and advantages of the present invention will become better understood with reference to the following description and claims.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, preferably to fluorine and chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Alkyl groups can optionally be substituted e.g. with halogen, hydroxy, lower-alkoxy, lower-alkoxy-carbonyl, $NH_2$, N(H, lower-alkyl) and/or N(lower-alkyl)$_2$. Unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl". Unsubstituted lower-alkyl groups are preferred.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Alkoxy and lower-alkoxy groups may optionally have a substitution pattern as described earlier in connection with the term "alkyl". Unsubstituted alkoxy and lower-alkoxy groups are preferred.

The term "amino acid" refers to both natural amino acids, to their enantiomers, and to unnatural amino acids. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to azetidinecarboxylic acid, 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4 diaminoisobutyric acid, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, allo-isoleucine, N-methylglycine, N-methylisoleucine, N-methylvaline, norvaline, norleucine, ornithine and pipecolic acid.

The term "aryl" relates to an aromatic carbocyclic or heterocyclic ring or ring system, preferably having from 5 to 6 carbon atoms. Examples of aryl groups include phenyl, furanyl, thiophenyl, pyridinyl, thiazolyl and oxazolyl, which can optionally be mono- or multiply-substituted by lower-alkyl, lower-alkoxy, halogen, CN, $CF_3$, hydroxy, $NO_2$, $NH_2$, N(H, lower-alkyl) and/or N(lower-alkyl)$_2$. Preferred substituents are lower-alkyl, lower-alkoxy, halogen, and/or $NO_2$.

The term "carbocyclic ring" refers to a substituted or unsubstituted monocyclic or bicyclic aromatic hydrocarbon ring system of 5 to 10 members, preferably 5 or 6 members. Preferred groups include phenyl, naphthyl, tolyl, xylyl, etc.

The term "heterocyclic ring" refers to a 5- or 6-membered ring which can comprise 1, 2 or 3 atoms selected from nitrogen, oxygen and/or sulfur such as tetrahydropyridine, dihydrofuran, dihydropyran, furyl, pyrrolyl, pyridyl, 1,2-, 1,3- and 1,4-diazinyl, thienyl, oxazolyl, oxadiazolyl, isoxazolyl, thiazolyl, isothiazolyl or imidazolyl. The heterocyclic ring may be optionally substituted with an aryl group or have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulfuric acid, phosphoric acid, citric acid, formic acid, maleic acid, acetic acid, fumaric acid, succinic acid, tartaric acid, methanesulfonic acid, p-toluenesulfonic acid and the like, which are non toxic to living organisms. Preferred salts with acids are formates, maleates, citrates, hydrochlorides, hydrobromides and methanesulfonic acid salts.

This term also encompasses carboxylate salts having organic and inorganic cations, such as alkali and alkaline earth metal cations (for example, lithium, sodium, potassium, magnesium, barium and calcium); ammonium; or organic cations, for example, dibenzylammonium, benzylammonium, 2-hydroxyethylammonium, bis(2-hydroxyethyl) ammonium, phenylethylbenzylammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term "leaving group" relates to a group which is removed or replaced during a reaction. Examples of leaving groups are halogen, mesylate and tosylate.

In detail, the present invention relates to compounds of formula (I)

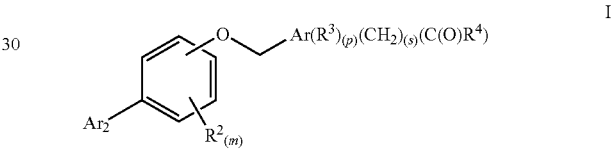

wherein

Ar is an aromatic carbocyclic or heterocyclic ring;

$Ar_2$ is a substituted or unsubstituted cyclic ring selected from the group consisting of benzo[1,3]dioxol-5-yl, furan-2-yl, isoquinolin-5-yl, isoxazol-4-yl, 1-naphthyl, pyrazol-1-yl, pyrazol-4-yl, pyridin-3-yl, thiophen-2-yl, thiophen-3-yl and phenyl and where substituted the substituents are selected from the group consisting of acetamido, aminocarbonyl, benzyl, benzyloxy, halogen, hydroxyl-lower alkyl, lower alkyl, lower alkoxy-lower alkyl, phenoxy, phenyl, lower alkoxy and trifluoro-methoxy;

$R^2$ and $R^3$ are independently selected from the group consisting of lower alkyl, lower alkoxy, trifluoromethyl, halogen, hydroxy, amino, alkylamino, diakylamino, cyano and nitro;

$R^4$ is hydroxy or an amino acid attached through a nitrogen atom of the amino acid;

m is 0, 1, 2, 3 or 4;

p is 0, 1 or 2, and s is 0, 1 or 2 or a pharmaceutically acceptable salt thereof, provided that when $Ar_2$ is phenyl, the phenyl ring is substituted by at least one substituent selected from the group consisting of acetamido, aminocarbonyl, benzloxy, hydroxyl-lower alkyl, lower-alkoxy-lower alkyl, phenoxy, phenyl, pyrazol-1-yl and trifluoromethoxy and when Ar2 is substituted or unsubstituted phenyl, there are not two lower alkyl substituents ortho to the point of attachment of the Ar2 ring.

Compounds of formula (I) represent a preferred embodiment of the present invention and pharmaceutically acceptable salts of compounds of formula (I) individually also represent a preferred embodiment of the present invention.

Some preferred compounds are those where Ar$_2$ is phenyl substituted in the meta position by acetamido, aminocarbonyl or hydroxymethyl.

A further preferred compound is that where Ar$_2$ is pyridine-3-yl.

Another preferred compound is one where the pyridine-3-yl is substituted by halogen.

Yet another preferred compound is one where Ar$_2$ is phenyl substituted in the ortho position by trifluoromethoxy.

Other preferred compounds are those where Ar$_2$ is phenyl substituted in the ortho by methoxymethyl, benzyloxy or phenoxy.

Another preferred compound is one where Ar$_2$ is 1-naphthyl.

Another preferred compound is one where Ar$_2$ is benzo[1,3]dioxol-5-yl.

Another preffered compound is one where Ar$_2$ is thiophen-3-yl.

Other preferred compounds are those of the formula

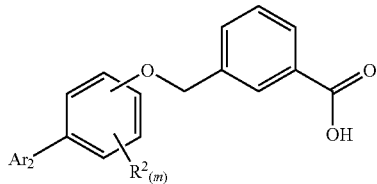

1A wherein Ar$_2$, R$^2$ and m are as in formula 1.

Another group of preferred compounds are those of the formula

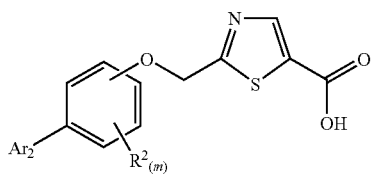

1B wherein Ar$_2$, R$^2$ and m are as in formula 1.

Yet another group of preferred compounds are those of the formula

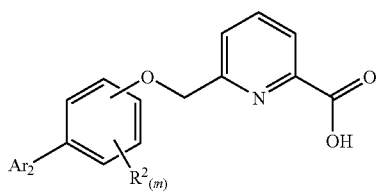

1C wherein Ar$_2$, R$^2$ and m are as in formula 1.

Another group of preferred compounds are those of the formula

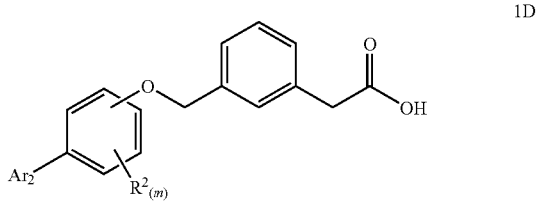

1D wherein Ar$_2$, R$^2$ and m are as in formula 1.

Other preferred compounds of general formula (I) are those selected from the group consisting of
3-(3'-Acetylamino-biphenyl-4-yloxymethyl)-benzoic acid;
3-(4-Benzo[1,3]dioxol-5-yl-phenoxymethyl)-benzoic acid;
3-(3'-Carbamoyl-biphenyl-4-yloxymethyl)-benzoic acid;
3-[4-(2-Chloro-pyridin-3-yl)-phenoxymethyl]-benzoic acid;
3-[4-(6-Chloro-pyridin-3-yl)-phenoxymethyl]-benzoic acid;
3-[4-(3,5-Dimethyl-isoxazol-4-yl)-phenoxymethyl]-benzoic acid;
3-[4-(2-Fluoro-pyridin-3-yl)-phenoxymethyl]-benzoic acid;
3-[4-(6-Fluoro-pyridin-3-yl)-phenoxymethyl]-benzoic acid;
3-(4-Furan-2-yl-phenoxymethyl)-benzoic acid;
3-(3'-Hydroxymethyl-biphenyl-4-yloxymethyl)-benzoic acid;
3-(4-Isoquinolin-5-yl-phenoxymethyl)-benzoic acid;
3-(2'-Methoxymethyl-biphenyl-4-yloxymethyl)-benzoic acid;
3-(3'-Methoxymethyl-biphenyl-4-yloxymethyl)-benzoic acid;
3-(4-Naphthalen-1-yl-phenoxymethyl)-benzoic acid;
3-(2'-Phenoxy-biphenyl-4-yloxymethyl)-benzoic acid;
3-(3'-Pyrazol-1-yl-biphenyl-4-yloxymethyl)-benzoic acid;
3-(4-Pyridin-3-yl-phenoxymethyl)-benzoic acid;
3-(4-Thiophen-3-yl-phenoxymethyl)-benzoic acid;
3-(2'-Trifluoromethoxy-biphenyl-4-yloxymethyl)-benzoic acid;
3-(4'-Trifluoromethoxy-biphenyl-4-yloxymethyl)-benzoic acid;
2-(3'-Acetylamino-biphenyl-4-yloxymethyl)-thiazole-4-carboxylic acid;
2-(4-Benzo[1,3]dioxol-5-yl-phenoxymethyl)-thiazole-4-carboxylic acid;
2-(2'-Benzyloxy-biphenyl-4-yloxymethyl)-thiazole-4-carboxylic acid;
2-[4-(1-Benzyl-1H-pyrazol-4-yl)-phenoxymethyl]-thiazole-4-carboxylic acid;
2-([1,1';3',1'']Terphenyl-4-yloxymethyl)-thiazole-4-carboxylic acid;
2-(3'-Carbamoyl-biphenyl-4-yloxymethyl)-thiazole-4-carboxylic acid;
2-[4-(2-Chloro-pyridin-3-yl)-phenoxymethyl]-thiazole-4-carboxylic acid;
2-[4-(6-Fluoro-pyridin-3-yl)-phenoxymethyl]-thiazole-4-carboxylic acid;
2-(3'-Hydroxymethyl-biphenyl-4-yloxymethyl)-thiazole-4-carboxylic acid;
2-(4-Isoquinolin-5-yl-phenoxymethyl)-thiazole-4-carboxylic acid;
2-(2'-Methoxymethyl-biphenyl-4-yloxymethyl)-thiazole-4-carboxylic acid;
2-(3'-Methoxymethyl-biphenyl-4-yloxymethyl)-thiazole-4-carboxylic acid;
2-(4-Naphthalen-1-yl-phenoxymethyl)-thiazole-4-carboxylic acid;

2-(2'-Phenoxy-biphenyl-4-yloxymethyl)-thiazole-4-carboxylic acid;
2-(4-Thiophen-3-yl-phenoxymethyl)-thiazole-4-carboxylic acid;
2-(2'-Trifluoromethoxy-biphenyl-4-yloxymethyl)-thiazole-4-carboxylic acid;
6-(4-Benzo[1,3]dioxol-5-yl-phenoxymethyl)-pyridine-2-carboxylic acid;
6-(2'-Methoxymethyl-biphenyl-4-yloxymethyl)-pyridine-2-carboxylic acid;
6-(4-Thiophen-2-yl-phenoxymethyl)-pyridine-2-carboxylic acid;
[3-(3'-Acetylamino-biphenyl-4-yloxymethyl)-phenyl]-acetic acid;
[3-(3'-Hydroxymethyl-biphenyl-4-yloxymethyl)-phenyl]-acetic acid;
[3-(2'-Methoxymethyl-biphenyl-4-yloxymethyl)-phenyl]-acetic acid;
{3-[4-(2-Methoxy-pyridin-3-yl)-phenoxymethyl]-phenyl}-acetic acid; and
[3-(2'-Trifluoromethoxy-biphenyl-4-yloxymethyl)-phenyl]-acetic acid Compounds of formula I that have one or more asymmetric carbon atoms can exist in the form of optically pure enantiomers or as racemates. The invention embraces all of these forms.

It will be appreciated, that the compounds of general formula I in this invention may be derivatized at functional groups to provide derivatives which are capable of conversion back to the parent compound in vivo.

As described above, the compounds of formula I of the present invention may be used as medicaments for the treatment and/or prophylaxis of diseases mediated by the activation of the glycogen synthase enzyme. Preferably, the compounds of the present invention may be used to treat type 2 diabetes.

The invention therefore also relates to pharmaceutical compositions comprising a compound as defined above and a pharmaceutically acceptable carrier and/or adjuvant.

The compounds of formula I can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol, and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 4 dosage units.

The pharmaceutical preparations conveniently contain about 1-500 mg, preferably 1-100 mg, of a compound of formula 1.

The following Examples serve to illustrate the present invention in more detail. They are, however, not intended to limit its scope in any manner.

General Methods

The compounds used in the present invention can be prepared by any conventional means. Suitable processes for synthesizing these compounds are provided in the examples. Generally, compounds of formula I can be prepared according to one of the synthetic routes described below: Nucleophilic Displacement or Suzuki Coupling. The sources of the starting materials for these reactions are described subsequently.

Nucleophilic Displacement

As shown in Scheme 1, compounds of the invention can be prepared by nucleophilic displacement of a leaving group LG from a compound of formula 5 by a hydroxybiaryl of formula 4 to form a compound of formula 6 in which R1 represents a protective group commonly used for the protection of a carboxylic acid. The protective group is then cleaved to give the compound of the invention of formula 1.

Many protective groups R1 are known to those of skill in the art of organic synthesis. For example, several suitable protective groups are enumerated in "Protective Groups in Organic Synthesis" [T. W. Greene and P. G. M. Wuts, $2^{nd}$ Edition, John Wiley & Sons, N.Y. 1991]. Preferred protective groups are those compatible with the reaction conditions used to prepare compounds of the invention. Examples of such protective groups are lower alkyl straight-chain or branched esters (e.g., methyl (R1=CH$_3$), ethyl (R1=CH$_2$CH$_3$), or tert-butyl (R1=C(CH$_3$)$_3$) esters), or the benzyl ester (R1=CH$_2$C$_6$H$_5$).

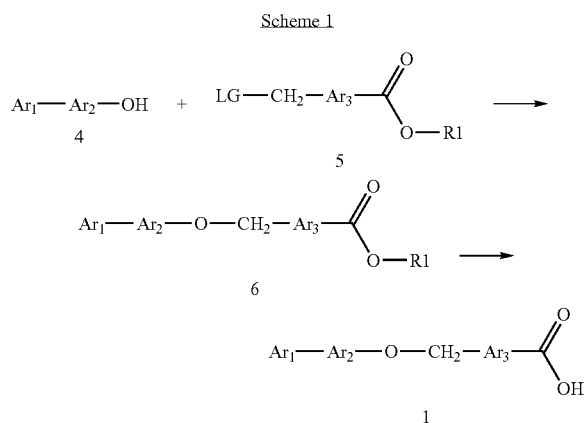

Scheme 1

The nucleophilic displacement of the leaving group LG in compound 5 can be effected by any conventional means. For example, in the case where LG represents the leaving group chlorine, bromine, or iodine, the reaction can conveniently be carried out by treating compound 5 with compound 4 in the presence of a base such as an alkali metal hydride (for example, sodium hydride) in an inert solvent (e.g., N,N-dimethylformamide) or an alkali metal carbonate (for example, potassium carbonate) in an inert solvent (e.g., a polar aprotic solvent such as N,N-dimethylformamide or a ketone such as acetone or methyl ethyl ketone) at a temperature between about room temperature and about 100 degrees.

The conversion of compound 6, in which R1 represents a protective group commonly used for the protection of a carboxylic acid, to compound 1 by deprotection of the carboxylic acid protective group is carried out using reaction conditions that are well known in the field of organic synthesis, and many of which are outlined in "Protective Groups in Organic Synthesis" [T. W. Greene and P. G. M. Wuts, 2$^{nd}$ Edition, John Wiley & Sons, N.Y. 1991]. For example, in the case where R1 is methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature. As another example, in the case where R1 is a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature. As a final (but not limiting) example, in the case where R1 is a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

Suzuki Coupling

As shown in Scheme 2, compounds of the invention can be prepared by a reaction sequence starting with nucleophilic displacement of a leaving group LG from a compound of formula 5 by a compound of formula 7, in which X represents a group that can act as a leaving group in a noble metal-catalyzed coupling reaction such as a Suzuki reaction or a Stille reaction, to form a compound of formula 9 in which R1 represents a protective group commonly used for the protection of a carboxylic acid.

The compound of formula 9 can then be reacted with an organometallic reagent of formula 10 (for example, a boronic acid or an organotin reagent) under noble metal catalysis to give a biaryl compound of formula 11. The protective group is then cleaved to give the compound of the invention of formula 1.

Many protective groups R1 are known to those of skill in the art of organic synthesis. For example, several suitable protective groups are enumerated in "Protective Groups in Organic Synthesis" [T. W. Greene and P. G. M. Wuts, 2$^{nd}$ Edition, John Wiley & Sons, N.Y. 1991]. Preferred protective groups are those compatible with the reaction conditions used to prepare compounds of the invention. Examples of such protective groups are lower alkyl straight-chain or branched esters (e.g., methyl (R1=CH$_3$), ethyl (R1=CH$_2$CH$_3$), or tert-butyl (R1=C(CH$_3$)$_3$) esters), or the benzyl ester (R1=CH$_2$C$_6$H$_5$).

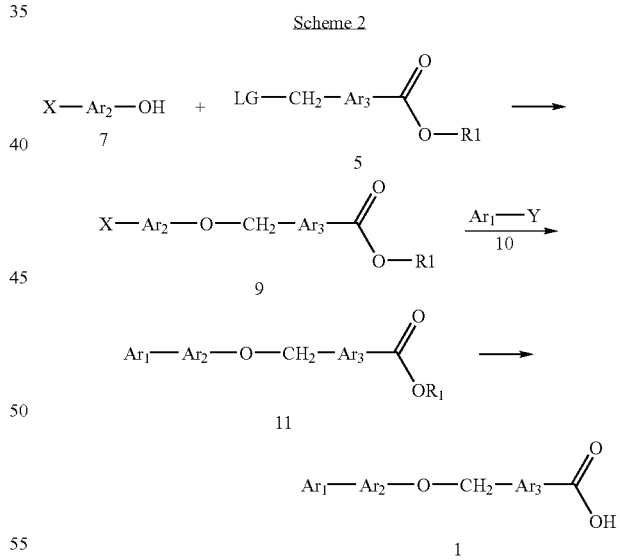

Scheme 2

The nucleophilic displacement of the leaving group LG in compound 5 can be effected by any conventional means. For example, in the case where LG represents the leaving group chlorine, bromine, or iodine, the reaction can conveniently be carried out by treating compound 5 with compound 7 in the presence of a base such as an alkali metal hydride (for example, sodium hydride) in an inert solvent (e.g., N,N-dimethylformamide) or an alkali metal carbonate (for example, potassium carbonate) in an inert solvent (e.g., a polar aprotic solvent such as N,N-dimethylformamide or a ketone such as acetone or methyl ethyl ketone) at a temperature between about room temperature and about 100 degrees.

The reaction of a compound of formula 9, where X represents a leaving group such as iodine, bromine, or triflate, with a compound of formula 10, where Y represents boronic acid, boronate ester, trimethyltin or tri-n-butyl-tin, to give a compound of formula 11 can be effected using Suzuki or Stille coupling conditions which are well known to one of average skill in the art. For example, the reaction can be conveniently carried out by reacting a compound of formula 9 where X represents iodine with a compound of formula 10 where Y represents $B(OH)_2$, in a convenient inert solvent such as a polar aprotic solvent (e.g., N,N-dimethylformamide) or an ether (e.g., dioxane) or water, in the presence of a catalytic amount of a palladium(0) complex (e.g., tetrakis(triphenylphos-phine)palladium(0)) or a compound which can be reduced in situ to give palladium(0) (for example, palladium (II) acetate or bis(triphenylphosphine)palladium(II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexylphosphine)palladium, and also in the presence of an inorganic base, for example, an alkali metal carbonate, bicarbonate or phosphate (e.g., potassium phosphate or sodium carbonate) at a temperature between about room temperature and about 100 degrees, and preferably at between about room temperature and about 50 degrees. It is also possible to use an alkali metal hydroxide such as sodium hydroxide or potassium hydroxide as the base in this reaction, but as is clear to one of average skill in the art, this may lead to other side reactions such as hydrolysis of any hydrolytically labile moiety (for example, a carboxylate ester) in the molecule, and this effect may be desired or not desired by the experimenter. Consequently, the selection of the base depends on whether or not it is desired to avoid a hydrolysis reaction. If so, then an alkali metal hydroxide should not be selected as the base and one of the other bases outlined above should be selected.

The conversion of compound 11, in which R1 represents a protective group commonly used for the protection of a carboxylic acid, to compound 1 by deprotection of the carboxylic acid protective group is carried out using reaction conditions that are well known in the field of organic synthesis, and many of which are outlined in "Protective Groups in Organic Synthesis" [T. W. Greene and P. G. M. Wuts, $2^{nd}$ Edition, John Wiley & Sons, N.Y. 1991]. For example, in the case where R1 is methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature. As another example, in the case where R1 is a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature. As a final (but not limiting) example, in the case where R1 is a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

Depending on the reaction conditions and the substrate employed, it is sometimes possible to prepare the carboxylic acid of formula 1 directly from the Suzuki reaction of a compound of formula 9, where X represents a leaving group such as iodine, bromine, or triflate, with a boronic acid of formula 10, where Y represents $B(OH)_2$ without a separate hydrolysis step. For example, a compound of formula 9 where X represents iodide can be treated with a boronic acid of formula 10, where Y represents $B(OH)_2$ in the presence of a complex of palladium(0) with a trialkylphosphine (scuh as bis(tri-cyclohexylphosphine)palladium) in the presence of potassium carbonate in an aqueous solvent such as a mixture of water and dioxane, at elevated temperature, such as at about 170 degrees. The reaction is carried out in a sealed tube and the heating is conveniently carried out using microwave irradiation. Alternatively, reactions conditions known in the literature can be employed. Examples of such conditions can be seen in the supplementary material for the article by W. Jiang et al. *J. Med. Chem.* 2003, 46, 441444, and also in S. C. Tucker et al. *Tetrahedron* 2001, 57, 2545-2554.

Starting Materials: Compounds of Formula 4

Many compounds of formula 4 are known compounds and can be synthesized according to literature procedures. Some examples are included in the table.

| Name | Reference |
| --- | --- |
| 2-(3-Amino-4-hydroxy-phenyl)-thiophene | M. A. Al'perovich et al. Zhumal Obshchei Khimii 1964, 34, 645-50 CAN 60: 83351 |
| 4-(2-Bromo-thiophen-3-yl)-phenol | A. Cravino et al. J. Phys. Chem. B 2002, 106, 70-76 |
| 2-Chloro-5-(4-chloro-3,5-diethyl-1H-pyrazol-1-yl)-4-fluoro-phenol | H. Ohyama et al. U.S. Pat. No. 4,752,326 |
| 4-Chloro-2-(3-ethyl-5-methyl-1(2)H-pyrazol-4-yl)-phenol | K. Takagi et al. Chem. Pharm. Bull. 1975, 23, 2427-31 |
| 4-(5-Chloro-3-methyl-pyrazol-1-yl)-phenol | A. Michaelis et al. Chem. Ber. 1900, 33, 2595-2607 |
| 2-(4-Chloro-pyridin-3-yl)-phenol | W. S. Yue et al. Org. Lett. 2002, 4, 2201-2204. |
| 4-(5-Chloro-thiophen-2-yl)-phenol | S. Gronowitz et al. Acta Pharm. Suec. 1974, 11, 211-224 |
| 4-(5-Chloro-thiophen-3-yl)-phenol | S. Gronowitz et al. Acta Pharm. Suec. 1974, 11, 211-224 |
| 2-(3,5-Diethyl-isoxazol-4-yl)-phenol | R. Royer et al. Bull. Soc. Chim. France 1963, 1746-1752 |
| 3,5-Dimethoxy-2-(2-methyl-naphthalen-1-yl)-phenol | G. Bringmann et al. J. Org. Chem. 2002, 67, 5595-5610. |
| 3-(3,5-Dimethyl-pyrazol-1-yl)-phenol | D. J. Alsop U.S. Pat. No. 3,929,828 |
| 5-(3,5-Dimethyl-1H-pyrazol-4-yl)-2-methyl-phenol | F. Langer et al. Monatsh. Chem. 1957, 88, 298-306 |
| 2-(3,5-Dimethyl-isoxazol-4-yl)-3-methyl-phenol | E. Bonfand et al. Synlett. 2000, 475-478. |
| 3,5-Dimethyl-2-(2-methyl-naphthalen-1-yl)-phenol | G. Bringmann et al. Tetrahedron: Asymmetry 1999, 10, 3025-3032 |
| 4-(3,5-Dimethyl-pyrazol-1-yl)-phenol | L. Claisen et al. Liebigs Ann. Chem. 1894, 278, 295 |
| 2-(3,5-Dimethyl-pyrazol-1-yl)-phenol | G. Fukata et al. Heterocycles 1982, 19, 1487-1495 |
| 2-(3-Ethyl-isoxazol-4-yl)-phenol | R. Royer et al. Bull. Soc. Chim. France 1963, 1746-1752 |
| 2-(5-Ethyl-isoxazol-4-yl)-phenol | R. Royer et al. Bull. Soc. Chim. France 1963, 1746-1752 |
| 2-(5-Ethyl-1-methyl-1H-pyrazol- | M. Hubert-Habart et al. Bull. Soc. |

| Name | Reference |
|---|---|
| 4-yl)-phenol | Chim. France 1966, 1587-1598. |
| 2-(5-Ethyl-3-methyl-isoxazol-4-yl)-phenol | M. Hubert-Habart et al. Bull. Soc. Chim. France 1966, 1587-1598. |
| 2-(3-Ethyl-5-methyl-isoxazol-4-yl)-phenol | R. Royer et al. Bull. Soc. Chim. France 1963, 1746-1752 |
| 2-(3-Ethyl-5-phenyl-isoxazol-4-yl)-phenol | R. Royer et al. Bull. Soc. Chim. France 1963, 1746-1752 |
| 4-(5-Ethyl-thiophen-2-yl)-phenol | N. L. Campbell et al. J. Mater. Chem. 2002, 12, 2706-2721 |
| 4-(5-Fluoro-thiophen-2-yl)-phenol | S. Gronowitz et al. Acta Pharm. Suec. 1974, 11, 211-224 |
| 3-Fluoro-5-(thiophen-2-yl)-phenol | R. Friesen et al. Canadian Patent Application CA 2169231 |
| 2-Furan-2-yl-4-hydroxy-benzonitrile | Y. Yamamoto et al. Synthesis 1996, 949-953 |
| 4-Furan-2-yl-phenol | F. D. King et al. Synthesis 1976, 40-42 |
| 1-(2'-Hydroxy-4',6'-dimethylphenyl)-2-methylnaphthalene | G. Bringmann et al. Chem. Europ. J. 1999, 5, 3029-3038 |
| 4-Hydroxy-2-(2-furanyl)-benzonitrile | Y. Yamamoto et al. Synthesis 1996, 949-953 |
| 4'-Hydroxy-4,5-methylenedioxy-2-biphenylmethanol, | T. Ikeda et al. J. Chem. Soc. 1956, 4749-4761 |
| 3-(4-Hydroxy-2-nitrophenyl)pyridine | H. Shigyo et al. Chem. Pharm. Bull. 1993, 41, 1573-1582 |
| 2-(4'-Hydroxyphenyl)benzyl alcohol | C. -G. Huang et al. J. Org. Chem. 1991, 56, 4846-4853. |
| 4-p-Hydroxyphenyl-3,5-dimethylpyrazole | C. Foces-Foces et al. J. Chem. Crystallogr. 1996, 26, 127-132 |
| 4-(4-Hydroxyphenyl)pyrazole | J. Elguero et al. Synthesis 1997, 563-566. |
| 4-Hydroxy-2-(2-thienyl)-benzonitrile | Y. Yamamoto et al. Synthesis 1996, 949-953 |
| 5-(2-Iodo-thiophen-2-yl)-2-methoxy-phenol | B. L. Flynn et al. Bioorg. Med. Chem. Lett. 2001, 11, 2341-2344 |
| 2'-Methoxymethyl-biphenyl-4-ol | Y. Shi et al. J. Chem. Soc. Chem. Commun. 1995, 1217-1218 |
| 4-(3',4'-Methylenedioxyphenyl)phenol | L. Balazs et al. Tetrahedron Lett. 2000, 41, 7583-7587 |
| 4-(3',4'-Methylenedioxyphenyl)3-trifluoromethyl-phenol | T. Hiyama et al. Synlett 1990, 53-4 |
| 3-(5-Methyl-furan-2-yl)-phenol | M. A. Tobias J. Org. Chem. 1970, 35, 267-269 |
| 3-(5-Methyl-furan-2-yl)-phenol | M. A. Tobias J. Org. Chem. 1970, 35, 267-269 |
| 2-Methyl-5-(p-hydroxyphenyl)furan | A. F. Oleinik et al. Khim.-Farm. Zh. 1984, 18, 697-699 CAN 101: 230269 |
| 3-Methyl-2-(naphthalen-1-yl)-phenol | E. Bonfand et al. Synlett. 2000, 475-478. |
| 4-(4-Methyl-6-propyl-pyridin-3-yl)-phenol | J. M. Gourley et al. J. Chem. Soc. D 1969, 709-710 |
| 2-(3-Methyl-pyrazol-1-yl)-phenol | G. Fukata et al. Heterocycles 1982, 19, 1487-1495 |
| 3-(3-Methyl-pyrazol-1-yl)-phenol | Geigy French Patent Application FR 1320597, 1963; Chem. Abstr. CAN 60: 17449 |
| 4-(3-Methyl-1H-pyrazol-1-yl)-phenol | J. C. Antilla et att. J. Org. Chem. 2004, 69, 5578-5587 |
| 2-(5-Methyl-pyridin-3-yl)-phenol | R. A. Abramovitch et al. J. Am. Chem. Soc. 1974, 96, 5265-5267 |
| 2-(6-Methyl-pyridin-3-yl)-phenol | R. A. Abramovitch et al. J. Am. Chem. Soc. 1974, 96, 5265-5267 |
| 2-(2-Methyl-pyridin-3-yl)-phenol | R. A. Abramovitch et al. J. Am. Chem. Soc. 1974, 96, 5265-5267 |
| 4-Methyl-2-(3-pyridyl)phenol | G. Petrillo et al. Tetrahedron 1990, 46, 7977-7990 |
| 4-(5-Methyl-thiophen-2-yl)-phenol | N. L. Campbell et al. J. Mater. Chem. 2002, 12, 2706-2721 |
| 4-(Naphthalen-1-yl)-phenol | J. Jacques et al. Bull. Soc. Chim. France 1966, 128-144. |
| 3-(Naphthalen-1-yl)-phenol | D. Nasipuri et al. J. Chem. Soc. Perkin Trans. 1 1973, 1451-1456 |
| 2-(Naphthalen-1-yl)-phenol | M. Orchin J. Am. Chem. Soc. 1948, 70, 495-497 |
| 2-(5-Phenyl-isoxazol-4-yl)-phenol | M. Martynoff Bull. Soc. Chim. France 1952, 1056-1060 |
| 4-(5-Propyl-thiophen-2-yl)-phenol | N. L. Campbell et al. J. Mater. Chem. 2002, 12, 2706-2721 |
| 2-Pyrazol-1-yl-phenol | G. Fukata et al. Heterocycles 1982, 19, 1487-1495 |
| 4-Pyrazol-1-yl-phenol | H. Jones et al. J. Med. Chem. 1978, 21, 1100-1104 |
| 2-Pyridin-3-yl-phenol | R. A. Abramovitch et al. J. Am. Chem. Soc. 1974, 96, 5265-5267 |
| 4-Pyridin-3-yl-phenol | R. A. Johnson et al. J. Med. Chem. 1986, 29, 1461-1468. |
| 3-(Pyridin-3-yl)-phenol | V. Prelog et al. Helv. Chim. Acta 1947, 30, 675-89 |
| 4-Thiophen-2-yl-phenol | L. J. Baldwin et al. J. Heterocycl. Chem. 1985, 22, 1667-1669 |
| 4-Thiophen-3-yl-phenol | L. J. Baldwin et al. J. Heterocycl. Chem. 1985, 22, 1667-1669 |
| 3-Thiophen-3-yl-phenol | L. J. Baldwin et al. J. Heterocycl. Chem. 1985, 22, 1667-1669 |
| 3-(Thiophen-2-yl)-phenol | V. Prelog et al. Helv. Chim. Acta 1947, 30, 675-89 |

In addition, some compounds of formula 4 are commercially available, including the following:

| Name | Supplier |
|---|---|
| 4'-Hydroxy-biphenyl-3-carboxylic acid amide | Ambinter SARL, Paris, France |
| 4-(5-Chloro-thiophen-2-yl)-phenol | Specs and Biospecs, Rijswijk, Netherlands |
| 2-(3,5-Dimethyl-pyrazol-1-yl)-phenol | ChemDiv, Inc. San Diego, CA |
| 4-(5-Methyl-furan-2-yl)-phenol | ChemDiv, Inc. San Diego, CA |
| 1-Phenyl-1H-5-(5'-chloro-2'-hydroxy-4'-methylphenyl)pyrazole | Aldrich Chemical Company, Inc., Milwaukee, WI |
| 2-(3,5-Dimethyl-1-phenyl-1H-pyrazol-4-yl)-phenol | ChemDiv, Inc. San Diego, CA |

Compounds of formula 4 that are not known in the literature may be prepared using reactions that are known per se. For example, they may be conveniently prepared according to Scheme 3.

Scheme 3

The reaction of a compound of formula 15 to give a compound of formula 4 can be carried out by several different methods that are well known in the field of organic synthesis. Several of these methods are outlined in "Protective Groups in Organic Synthesis" (T. W. Greene and P. G. M. Wuts, 2$^{nd}$ Edition, John Wiley & Sons, N.Y. 1991). It will be clear to one skilled in the art that this approach to the synthesis of compounds of formula 4 is most suitable in the case where any substituents in the compound of formula 4 are stable to the conditions used to convert the compound of formula 15 to the compound of formula 4, and especially in the case where the compound of formula 4 does not bear any lower-alkoxy substituents.

For example, a compound of formula 15 can be treated with trimethylsilyl iodide in an inert solvent such as a halogenated hydrocarbon (for example, chloroform) at a temperature between about room temperature and the boiling point of the solvent, conveniently at about 60 degrees. The trimethylsilyl iodide can be added as a reagent, or it can be prepared in situ from trimethylsilyl chloride and an inorganic iodide, such as potassium iodide.

As another example, the compound of formula 15 can be treated with boron tribromide in an inert solvent such as a halogenated hydrocarbon (for example, methylene chloride) at low temperature (such as −78 degrees) to give the compound of formula 4. Examples of the conversion of a compound of formula 15 to a compound of formula 4 using this process can be seen in L. I. Kruse et al. *J. Med. Chem.* 1987, 30, 486-494, in D. J. Cram et al. *J. Am. Chem. Soc.* 1985, 107, 3645-3657, in A. Kende et al. *J. Am. Chem. Soc.* 1988, 110, 2210-2218, and in A. G. Myers et al. *J. Am. Chem. Soc.* 1997, 119, 6072-6094.

As a further example, the compound of formula 15 can be treated with a lower-alkyl thiolate (for example, sodium ethanethiolate) in N,N-dimethylformamide at a temperature between around 100 degrees and around 153 degrees, to give the compound of formula 4. Conditions appropriate for this reaction can be seen in G. I. Feutrill et al. *Tetrahedron Lett.* 1970, 11, 1327 and also in J. A. Dodge et al. *J. Org. Chem.* 1995, 60, 739-741.

As yet another example, the compound of formula 15 can be treated with pyridine hydrochloride at elevated temperature (for example, at between about 160 degrees and about 220 degrees) to give the compound of formula 4. Examples of the conversion of a compound of formula 15 to a compound of formula 4 using this process can be seen in L. J. Baldwin et al. *J. Heterocycl. Chem.* 1985, 22, 1667-1669, in S. Gauthier et al. *Tetrahedron* 2000, 56, 703-709, in J. Gilbert et al. *J. Med. Chem.* 1983, 26, 693-699, in M. Konno et al. *Synlett* 1997, 1472-1474, and in P. C. Astles et al. *J. Med. Chem.* 1998, 41, 2732-2744.

Several compounds of formula 15 are available commercially, and some of these are shown in the table below. Other compounds of formula 15 are known in the literature, or can be made by methods that are well known in the art. Specifically, compounds of formula 15 can be made using Stille or Suzuki reactions analogous to those described below for the synthesis of compounds of formula 4 (see Scheme 4), except that an anisole is used in place of the phenolic compound of formula 7.

| Name | Supplier |
|---|---|
| 3-(3-Bromo-4-methoxyphenyl)pyridine | Synchem Inc., Des Plaines, IL |
| 3-(3,5-Dimethyl-4-methoxyphenyl)thiophene | Rieke Metals, Inc., Lincoln, NE |
| 3-(3-Fluoro-4-methoxyphenyl)thiophene | Rieke Metals, Inc., Lincoln, NE |
| 3-(5-Fluoro-2-methoxyphenyl)thiophene | Rieke Metals, Inc., Lincoln, NE |
| 3-(2-Methoxy-5-methylphenyl)-4-methylthiophene | Rieke Metals, Inc., Lincoln, NE |
| 3-(4-Methoxy-3-methylphenyl)-4-methylthiophene | Rieke Metals, Inc., Lincoln, NE |
| 3-(2-Methoxy-5-methylphenyl)thiophene | Rieke Metals, Inc., Lincoln, NE |
| 3-(4-Methoxy-2-methylphenyl)thiophene | Rieke Metals, Inc., Lincoln, NE |
| 3-(4-Methoxy-3-methylphenyl)thiophene | Rieke Metals, Inc., Lincoln, NE |
| 4-(2-Methoxyphenyl)-3-methyl-1H-pyrazole | Maybridge plc, Tintagel, UK |
| 4-(4-Methoxyphenyl)-1-methyl-1H-pyrazole | Peakdale Molecular, High Peak, UK |

-continued

| Name | Supplier |
|---|---|
| 3-(3-Methoxyphenyl)-4-methylthiophene | Rieke Metals, Inc., Lincoln, NE |
| 4-(4-Methoxyphenyl)-1-phenyl-1H-pyrazole | Peakdale Molecular, High Peak, UK |
| 4-(4-Methoxyphenyl)-1H-pyrazole | Peakdale Molecular, High Peak, UK |
| 2-(4-Methoxyphenyl)thiophene | Fluorochem Ltd., Old Glossop, UK |
| 3-(2-Methoxyphenyl)thiophene | Rieke Metals, Inc., Lincoln, NE |
| 3-(3-Methoxyphenyl)thiophene | Rieke Metals, Inc., Lincoln, NE |
| 3-(4-Methoxyphenyl)thiophene | Rieke Metals, Inc., Lincoln, NE |

An alternative approach to the synthesis of compounds of formula 4 is shown in Scheme 4.

Scheme 4

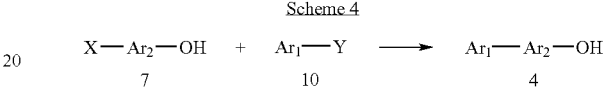

$$X-Ar_2-OH \ + \ Ar_1-Y \ \longrightarrow \ Ar_1-Ar_2-OH$$
$$\ \ \ \ \ 7 \ \ \ \ \ \ \ \ \ \ \ \ \ \ \ \ \ 10 \ \ \ \ \ \ \ \ \ \ \ \ \ \ \ \ \ \ 4$$

The reaction of a compound of formula 7, where X represents a leaving group such as iodine, bromine, chlorine, or triflate, with a compound of formula 10, where Y represents boronic acid, boronate ester, trimethyltin or tri-n-butyl-tin, to give a compound of formula 4 can be effected using Suzuki or Stille coupling conditions which are well known to one of average skill in the art. For example, the reaction can be conveniently carried out by reacting a compound of formula 7 where X represents iodine with a compound of formula 10 where Y represents $B(OH)_2$, in a convenient inert solvent such as a polar aprotic solvent (e.g., N,N-dimethylformamide) or an ether (e.g., dioxane) or water, in the presence of a catalytic amount of a palladium(0) complex (e.g., tetrakis(triphenylphosphine)palladium(0)) or a compound which can be reduced in situ to give palladium(0) (for example, palladium (II) acetate or bis(triphenylphosphine)pall-adium(II) chloride), in the optional additional presence of a catalytic amount of a phosphine ligand, for example tri-o-tolylphosphine or tri-tert-butylphosphine, and also in the presence of an inorganic base, for example, an alkali metal carbonate, bicarbonate or phosphate (e.g., potassium phosphate or sodium carbonate) at a temperature between about room temperature and about 100 degrees, and preferably at between about room temperature and about 50 degrees. As further examples, the reaction can be run according to the conditions of H. Sakurai et al. *J. Org. Chem.* 2002, 67, 2721, or the reaction can be run on solid phase using the conditions of J. D. Revell and A. Ganesan *Org. Lett.* 2002, 4, 3071.

In the case where $Ar_2$ is pyrazol-1-yl, compounds of formula 4 can be prepared according to Scheme 5, where Z is a group that can be converted to a hydroxy group. Examples of suitable Z groups will be evident to one of skill in the art, and include methoxy, nitro, and methanesulfonyloxy.

Scheme 5

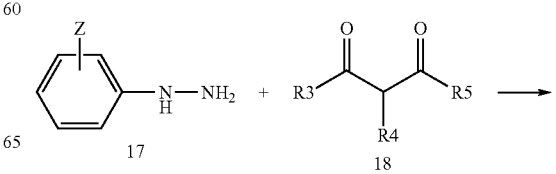

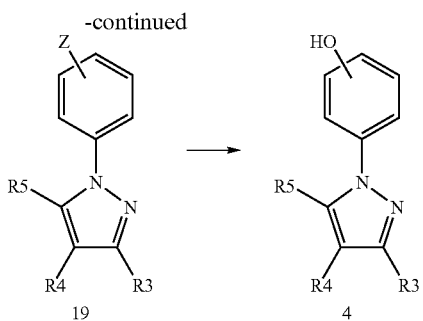

The compound of formula 17 is treated with a diketone of formula 18 in an inert solvent, such as an alcohol (e.g., ethanol) at the reflux temperature to give a pyrazole of formula 19, and then the Z group is converted to the hydroxy group to give the compound of formula 4. In the case where Z is methoxy, the reaction is conveniently carried out using reactions analogous to those described above in connection with Scheme 3. In the case where Z is nitro, the transformation takes place in two steps: hydrogenation to the aniline followed by a diazotization reaction to give the phenol. Conditions appropriate for this transformation can be seen in A. Michaelis et al. *Chem. Ber.* 1900, 33, 2595-2607. In the case where R is methanesulfonyloxy, the the transformation of the Z group to a hydroxy group is effected by a hydrolysis reaction where the compound of formula 19 is treated with an aqueous base, such as an alkali metal hydroxide (e.g., sodium hydroxide) in the optional additional presence of a co-solvent to ensure that the reaction mixture is in solution. Examples of suitable co-solvents are ethanol and dioxane. The reaction is conveniently carried out at between about 50 degrees and about the reflux temperature of the solvent or mixture of solvents. Conditions appropriate for this reaction can be seen in H. Ohyama et al. U.S. Pat. No. 4,752,326.

Starting Materials: Compounds of Formula 5

Many compounds of formula 5, in which R1 represents a protective group commonly used for the protection of a carboxylic acid, are known compounds and can be synthesized according to literature procedures. Some examples are included in the table.

| Name | Reference |
| --- | --- |
| 2-Bromomethyl-benzoic acid tert-butyl ester | T. Ziegler et al. Tetrahedron Lett. 2001, 42, 569-572 |
| 3-Bromomethyl-benzoic acid tert-butyl ester | W. Danho et al. U.S. Pat. No. 5,508,437 |
| 2-Bromomethyl-benzoic acid methyl ester | V. Dvornikovs et al. J. Org. Chem. 2002, 67, 2160-2167 |
| 3-Bromomethyl-benzoic acid methyl ester | V. Dvornikovs et al. J. Org. Chem. 2002, 67, 2160-2167 |
| 5-Bromomethyl-2-furancarboxylic acid ethyl ester | S. Tsuboi et al. Bull. Chem. Soc. Japan 1987, 60, 1807-1812 |
| 5-Bromomethyl-2-furancarboxylic acid methyl ester | J. Wityak et al. Bioorg. Med. Chem. Lett. 1995, 5, 2097-2100 |
| 6-Bromomethyl-pyridine-2-carboxylic acid methyl ester | D. I. C. Scopes et al. J. Med. Chem. 1992, 35, 490-501 |
| 2-Bromomethyl-thiazole-4-carboxylic acid ethyl ester | E. A. Hallinan et al. Bioorg. Med. Chem. 2001, 9, 1-6 |
| 5-Bromomethyl-thiophene-2-carboxylic acid methyl ester | M. L. Curtin et al. J. Med. Chem. 1998, 41, 74-95 |
| 3-Chloromethyl-benzoic acid benzyl ester | D. -W. Chen et al. J. Chem. Soc. Perkin Trans. 1 2001, 2796-2803 |
| 2-Chloromethyl-benzoic acid ethyl ester | F. Gadient et al. Helv. Chim. Acta 1962, 45, 1860-1870 |
| 3-Chloromethyl-benzoic acid methyl ester | T. Matsukawa et al. Yakugaku Zasshi 1950, 70, 535-537. Chem. Abs. 45: 36092 (1951) |
| 5-Chloromethyl-2-furancarboxylic acid n-butyl ester | J. G. M. Bremner et al. U.S. Pat. No. 2,450,108 |
| 5-Chloromethyl-2-furancarboxylic acid ethyl ester | T. K. Chakraborty et al. Tetrahedron Lett. 2002, 43, 1317-1320 |
| 6-Chloromethyl-pyridine-2-carboxylic acid ethyl ester | R. Fornasier et al. J. Chem. Soc. Perkin Trans. 2 1986, 233-238 |
| 5-Chloromethyl-thiophene-2-carboxylic acid methyl ester | V. Kozmik et al. Collect. Czech. Chem. Commun. 1992, 57, 1483-1486 |
| 3-Iodomethyl-benzoic acid methyl ester | R. C. Fuson et al. J. Am. Chem. Soc. 1940, 62, 1180-1183 |
| 5-Iodomethyl-2-furancarboxylic acid allyl ester | P. D. Greenspan et al. J. Med. Chem. 2001, 44, 4524-4534 |
| 5-Methanesulfonyloxymethyl-furan-2-carboxylic acid ethyl ester | J. B. Summers, Jr. et al. U.S. Pat. No. 5,486,525 |

In addition, some compounds of formula 5 are commercially available, including the following:

| Name | Supplier |
| --- | --- |
| 6-Bromomethyl-pyridine-2-carboxylic acid methyl ester | ChemPacific, Baltimore, MD |
| 5-Chloromethyl-2-furancarboxylic acid ethyl ester | Aldrich Chemical Company, Inc., Milwaukee, WI |
| 5-Chloromethyl-2-furancarboxylic acid methyl ester | Aldrich Chemical Company, Inc., Milwaukee, WI |
| 2-Bromomethyl-benzoic acid ethyl ester | Pfaltz &Bauer, Inc., Waterbury, CT |
| 2-Bromomethyl-benzoic acid methyl ester | ChemPacific, Baltimore, MD |
| 3-Bromomethyl-benzoic acid methyl ester | Lancaster Synthesis Ltd., Lancashire, UK |

Compounds of formula 5 that are neither known in the literature nor commercially available may be conveniently prepared by reactions that are well known in the field of organic synthesis, and these reactions can be represented generically as in Scheme 6.

Scheme 6

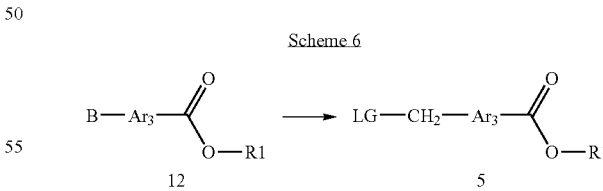

Three examples of reactions represented by Scheme 6 are described below. As will be clear to one of average skill in the art, not all reactions can be used to prepare all compounds of formula 5, but reactions appropriate for the preparation of specific compounds of formula-5 will be apparent to a synthetic organic chemist.

For example, a compound of formula 5, where LG represents chlorine, can be prepared from a compound of formula 12 where B represents hydrogen by an electrophilic aromatic substitution reaction by treating the compound of formula 12 where B represents hydrogen with formaldehyde and hydrogen chloride, in the presence of a Lewis acid catalyst, preferably zinc chloride, in a suitable inert solvent, for example, a halogenated alkane (such as methylene chloride, chloroform, 1,2-dichloroethane, or the like) at a temperature between about room temperature and the boiling point of the solvent, preferably at about 35 degrees celsius. Clearly this reaction is limited to cases where the compound of formula 12 is susceptible to electrophilic aromatic substitution at the desired point of attachment, and further, to cases where the compound of formula 5 is stable to mineral acids and to Lewis acids. Examples of compounds of formula 5 which fulfill these criteria will be known to one of average skill in the art. An example of such a reaction can be found in O. Moldenhauer et al. *Justus Liebigs Ann. Chem.* 1953, 580, 176.

Compounds of formula 5 where LG represents bromine can be prepared by treating a compound of formula 12 where B represents $CH_3$ with N-bromosuccinimide or 3,3-dimethyl-N,N'-dibromohydantoin in an inert solvent such as a halogenated alkane (for example, carbon tetrachloride) or acetonitrile, in the optional additional presence of a catalyst such as azobis(isobutyronitrile) or benzoyl peroxide at a suitable temperature, conveniently at the boiling point of the solvent, and in the optional additional presence of a source of light; or by treating a compound of formula 12 where B represents $CH_3$ with with bromine in an inert solvent such as a mixture of water and an aromatic hydrocarbon (e.g., benzene) or a halogenated alkane (e.g., chloroform) under irradiation with an incandescent light. Compounds of formula 5 where LG represents chlorine can be prepared by treating a compound of formula 12 where B represents $CH_3$ with N-chlorosuccinimide or sulfuryl chloride in an inert solvent such as a halogenated alkane (for example, carbon tetrachloride) or acetonitrile in the optional additional presence of a catalyst such as azobis(isobutyronitrile) or benzoyl peroxide at a suitable temperature, conveniently at the boiling point of the solvent, and in the optional additional presence of a source of light; or by treating a compound of formula 12 where B represents $CH_3$ with chlorine in an inert solvent such as a mixture of water and an aromatic hydrocarbon (e.g., benzene) or a halogenated alkane (e.g., chloroform or carbon tetrachloride) under irradiation with an incandescent light.

A compound of formula 5 where LG represents bromine can be prepared by treating a compound of formula 12 where B represents $CH_2OH$ with phosphorus tribromide or a mixture of N-bromosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 5 where LG represents chlorine can be prepared by treating a compound of formula 12 where B represents $CH_2OH$ with thionyl chloride or a mixture of N-chlorosuccinimide and triphenylphosphine in an inert solvent such as a halogenated alkane (e.g., methylene chloride or carbon tetrachloride) at a temperature between about 0 degrees and the boiling point of the solvent, conveniently at about 0 degrees. A compound of formula 5 where LG represents $OSO_2E$ where E represents lower alkyl or aryl can be prepared by treating a compound of formula 12 where B represents $CH_2OH$ with a sulfonyl chloride $ESO_2Cl$ (for example, methanesulfonyl chloride or p-toluenesulfonyl chloride) in the presence of a base such as a tertiary amine (e.g., triethylamine or diisopropylethylamine) in an inert solvent such as a halogenated hydrocarbon (e.g., methylene chloride) at a temperature between about 0 degrees and about room temperature, preferably about 0 degrees. A compound of formula 5 where LG represents iodine can be prepared by treating a compound of formula 5 where LG represents chlorine, bromine, or $OSO_2E$ where E represents lower alkyl or aryl, with an alkali metal iodide (e.g., sodium iodide) in an inert solvent such as a ketone (e.g., acetone or methyl ethyl ketone) at a temperature between about 50 degrees and about 80 degrees, conveniently at about the boiling point of the solvent.

Starting Materials: Compounds of Formula 7

Many compounds of formula 7, where X represents a leaving group such as chlorine, iodine, bromine, or triflate, are known compounds and can be synthesized according to literature procedures. Some examples are included in the table.

| Name | Reference |
|---|---|
| 3-Bromo-4-chloro-phenol | Liedholm, B. Acta Chem. Scand Series B 1984, B38, 877-894 |
| 4-Bromo-2-chloro-phenol | Jaeger, R. et al. U.S. Pat. No. 4,223,166 |
| 6-Bromo-5-chloro-pyridin-3-ol | Koch, V. et al. Synthesis 1990, 499-501 |
| 4-Bromo-2,6-dichlorophenol | Malm, J. et al. WO 02/62780 |
| 5-Bromo-2-hydroxy-benzene-sulfonamide | Meyer, W. et al. U.S. Pat. No. 4,479,821 |
| 4-Bromo-3-nitro-phenol | Lavoie, E. J. et al. U.S. Pat. No. 6,486,167 |
| 3-Bromo-4-methyl-phenol | Jacquesy, J. C. J. Chem. Soc. Chem. Commun. 1980, 110-111 |
| 5-Bromo-2-nitro-phenol | Makosza, M. et al. J. Org. Chem. 1998, 63, 4199-4208 |
| 3-Bromo-phenol | Matarasso-Tchiroukhine, E. Ann. Chim. (Paris) 1958, 3, 405-459 Chem. Abs. 53: 34694 |
| 2-tert-Butyl-4-iodophenol | Tashiro, M. et al. J. Org. Chem. 1977, 42, 835-838 |
| 3,5-Dimethyl-4-iodophenol | Lu, Y. et al. Synthesis 2001, 1639-1644 |
| 3-Iodo-phenol | Noelting and Stricker Chem. Ber. 1887, 20, 3019 |
| 5-Bromo-2-hydroxy-thiazole-4-carboxylic acid ethyl ester | Serra, G. et al. Heterocycles 1995, 41, 2701-2712 |
| 5-Bromo-3-hydroxy-thiophene-2-carbonitrile | Binder, D. et al. Arch. Pharm. (Weinheim) 1988, 321, 391-395 |
| 6-Bromo-pyridin-2-ol | Wibaut, J. P. et al. Recl. Trav. Chim. Pays-Bas 1940, 59, 202-206 |
| 6-Bromo-pyridin-3-ol | den Hertog, H. J. et al. Recl. Trav. Chim. Pays-Bas 1950, 69, 1281-1288 |
| 2-Chloro-4,6-dimethyl-pyrimidinol | Hurst, D. T. Heterocycles 1984, 22, 79-84 |
| 2-Chloro-4-methoxy-6-methyl-pyrimidin-5-ol | Dohmori, R. et al. Chem. Pharm. Bull. 1970, 18, 1908-1914 |
| 2-Chloro-pyrimidin-5-ol | Hurst, D. T. et al. J. Chem. Soc. 1965, 7116-7119 |
| 6-Iodo-pyridin-3-ol | Edgar, K. J. et al. J. Org. Chem. 1990, 55, 5287-5291 |

In addition, many compounds of formula 7 are commercially available, including the following:

| Name | Supplier |
|---|---|
| 4-Bromo-2-chloro-phenol | Aldrich Chemical Company, Inc., Milwaukee, WI |
| 4-Bromo-2-chloro-6-methyl-phenol | Lancaster Synthesis Ltd., Lancashire, UK |
| 5-Bromo-2,3-difluoro-phenol | Lancaster Synthesis Ltd., Lancashire, UK |
| 4-Bromo-3,5-dimethyl-phenol | Aldrich Chemical Company, Inc., Milwaukee, WI |
| 5-Bromo-2-hydroxy-benzamide | SALOR, Aldrich Chemical Company, Inc., Milwaukee, WI |
| 5-Bromo-2-hydroxy-benzonitrile | Oakwood Products, West Columbia, SC |

-continued

| Name | Supplier |
| --- | --- |
| 5-Bromo-2-hydroxy-3-nitro-pyridine | Oakwood Products, West Columbia, SC |
| 3-Bromo-5-hydroxy-pyridine | Specs and Biospecs, Rijswijk, Netherlands |
| 4-Bromo-phenol | Aldrich Chemical Company, Inc., Milwaukee, WI |
| 2-Chloro-3-fluoro-5-hydroxy-pyridine | Asymchem International, Inc., Durham, NC |
| 5-Chloro-2-hydroxy-4,6-dimethyl-nicotinonitrile | Maybridge plc, Tintagel, UK |
| 2-Chloro-5-hydroxy-pyridine | Asymchem International, Inc., Durham, NC |
| 2-Hydroxy-5-bromo-pyrimidine | Lancaster Synthesis Ltd., Lancashire, UK |
| 4-Iodo-2-methyl-phenol | Aldrich Chemical Company, Inc., Milwaukee, WI |
| 3-Iodo-phenol | Aldrich Chemical Company, Inc., Milwaukee, WI |
| 4-Iodo-phenol | Aldrich Chemical Company, Inc., Milwaukee, WI |

Compounds of formula 7 that are neither known in the literature nor commercially available may be conveniently prepared by reactions that are well known in the field of organic synthesis as shown in Scheme 7.

Scheme 7

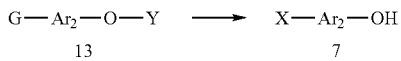

A compound of formula 7 can be prepared from a compound of formula 13 where G and X represent the same substituent selected from among chlorine, bromine, and iodine, and Y represents methyl, using reactions that are well known in the field of organic synthesis. Several of these methods are outlined in "Protective Groups in Organic Synthesis" (T. W. Greene and P. G. M. Wuts, $2^{nd}$ Edition, John Wiley & Sons, N.Y. 1991). For example, a compound of formula 7 can be formed by treating with trimethylsilyliodide a compound of formula 13 where G and X represent the same substituent selected from among chlorine, bromine, and iodine, and Y represents methyl. The reaction is conveniently carried out in an inert solvent, such as a halogenated alkane (e.g., chloroform) or acetonitrile, at a temperature between about room temperature and the boiling point of the solvent, preferably at about 50 degrees. Alternatively, a compound of formula 7 can be formed by heating a compound of formula 13 where G and X represent the same substituent selected from among chlorine, bromine, and iodine, and Y represents methyl with hydrogen bromide in acetic acid or water at reflux. As a third alternative, a compound of formula 7 can be formed by treating a compound of formula 13 where G and X represent the same substituent selected from among chlorine, bromine, and iodine, and Y represents methyl with boron tribromide in an inert solvent such as such as a halogenated alkane (e.g., chloroform or methylene chloride) at a temperature between about 0 degrees and about 40 degrees, conveniently at about room temperature.

A compound of formula 7 where X represents chlorine and the position of attachment of X is para to the hydroxy group can be prepared by treating a compound of formula 13 where G represents hydrogen and Y represents hydrogen with sulfuryl chloride in an inert solvent such as ether or a halogenated hydrocarbon (e.g. chloroform), at a temperature between about 0 degrees and about 35 degrees, preferably at about room temperature. A compound of formula 7 where X represents bromine and the position of attachment of X is para to the hydroxy group can be prepared by treating a compound of formula 13 where G represents hydrogen and Y represents hydrogen with bromine in an inert solvent such as water, or carbon tetrachloride, or acetic acid, at a temperature between about 0 degrees and about room temperature, preferably at about room temperature. Alternatively, the same compound 7 where X represents bromine and the position of attachment of X is para to the hydroxy group can be prepared by treating a compound of formula 13 where G represents hydrogen and Y represents hydrogen with a tribromide salt (e.g., tetrabutylammonium tribromide or benzyltrimethylammonium tribromide) in an inert solvent such as a halogenated hydrocarbon (e.g. methylene chloride or chloroform) at a temperature between about 0 degrees and about room temperature, preferably at about room temperature. A compound of formula 7 where X represents iodine and the position of attachment of X is para to the hydroxy group can be prepared by treating a compound of formula 13 where G represents hydrogen and Y represents hydrogen with iodine, or iodine monochloride in an inert solvent such as water, in the presence of an inorganic base such as an alkali metal hydroxide (e.g., sodium hydroxide) or an alkali metal carbonate (e.g., sodium carbonate) at a temperature between about 0 degrees and about room temperature, preferably at about room temperature. The same compound of formula 7 where X represents iodine and the position of attachment of X is para to the hydroxy group can be prepared by treating a compound of formula 13 where G represents hydrogen and Y represents hydrogen with sodium iodide and sodium hypochlorite in an inert solvent such as a mixture of water and an alcohol (e.g., methanol), at a temperature close to 0 degrees. This last reaction and several alternatives are described in K. J. Edgar and S. N. Falling J. Org. Chem. 1990, 55, 5287-5291.

A compound of formula 7 where X represents chlorine, bromine, or iodine can be prepared by treating a compound of formula 13 where G represents NH2 and Y represents hydrogen using the Sandmeyer reaction which is well known in the art of organic synthesis. Details of this reaction can be found in H. H. Hodgson Chem. Rev. 1947, 40, 251-277 and also in D. C. Nonhebel, Copper-catalyzed Single-electron Oxidations and Reductions, Special Publication—Chemical Society (London) 1970, 24, 409-437 ISSN: 0577-618X. For example, a compound of formula 13 where G represents NH2 and Y represents hydrogen can be converted to a diazonium intermediate of formula 13 where G represents $N_2^+$ and Y represents hydrogen by treament with sodium nitrite in the presence of a mineral acid (for example, hydrochloric acid or sulfuric acid) in water at a temperature between about −10 degrees and about 10 degrees, preferably about zero degrees. Without isolation, this diazonium intermediate can then be converted to a compound of formula 7 where X represents chlorine by treatment with copper(I) chloride, to a compound of formula 7 where X represents bromine by treatment with copper(I) bromide, or to a compound of formula 7 where X represents iodine by treatment with potassium iodide.

Starting Materials: Compounds of Formula 10

Many compounds of formula 10, where Y represents boronic acid, boronate ester, trimethyltin or tri-n-butyl-tin, are known compounds and can be synthesized according to literature procedures. Some examples are included in the table.

| Name | Reference |
|---|---|
| 4-Bromo-3,5-dimethyl-thiophen-2-yl-boronic acid | M. Takeshita et al. J. Org. Chem. 1998, 63, 6643-6649 |
| (4-Bromo-5-methyl-thiophen-2-yl)-boronic acid | S. L. Gilat et al. Chem. Eur. J. 1995, 1, 275-284 |
| 2-Chloro-6-methyl-pyridin-3-yl-boronic acid | M. Nishida et al. JP 2003160586 |
| 2,5-Dichloro-thiophen-3-yl-boronic acid | A. Kuno et al. PCT Int. Appl. WO 9604241 |
| 2,6-Dimethyl-4-(4,4,5,5-tetramethyl-[1,3,2]dioxaborolan-2-yl)-pyridine | Cho, J. -Y. et al. J. Am. Chem. Soc. 2000, 122, 12868-12869 |
| 2-(1-Ethoxyethyl)-phenyl-boronic acid | Dale, W. J. et al. J. Org. Chem. 1962, 27, 2598-2603 |
| 5-(Ethoxymethyl-pyridin-3-yl)-boronic acid | D. S. Hays et al. PCT Int. Appl. WO 2004058759 |
| 7-Ethyl-benzo[1,3]dioxole-5-boronic acid | T. E. Jacks et al. Org. Proc. Res. Dev. 2004, 8, 201-212 |
| (5-Ethyl-furan-2-yl)-boronic acid | L. Carles et al. J. Org. Chem. 2002, 67, 4304-4308 |
| (5-Ethyl-furan-2-yl)-trimethyl-stannane | Sasabe, M. et al. Perkin 1 2000, 3786-3790 |
| (5-Ethyl-thiophen-2-yl)-boronic acid | M. F. Chan et al. PCT Int. Appl. WO 9631492 |
| 4-Fluoro-naphthalen-1-yl-boronic acid | J. A. Lowe III et al. J. Med. Chem. 2004, 47, 1575-1586 |
| (3-Hydroxymethyl-thiophen-2-yl)-boronic acid | Y. Han et al. PCT Int. Appl. WO 9918099 |
| (4-Hydroxymethyl-thiophen-3-yl)-boronic acid | O. Axelsson et al. Eur. Pat. Appl. EP 604353 |
| 5-Methoxymethyl-pyridin-3-yl-boronic acid | S. Bourrain et al. PCT Int. Appl. WO 9745432 |
| (5-Methyl-furan-2-yl)-boronic acid | D. Florentin et al. J. Heterocycl. Chem. 1976, 13, 1265-1272 |
| 4-Methyl-naphthalen-1-yl-boronic acid | J. A. Lowe III et al. PCT Int. Appl. WO 9910339 |
| 2-Methyl-naphthalen-1-yl-boronic acid | A. N. Cammidge et al. Tetrahedron 2004, 60, 4377-4386 |
| (3-Methyl-thiophen-2-yl)-boronic acid | Y. Li et al. Macromolecules 2002, 35, 6900-6905 |
| 2-Methyl-thiophen-3-yl-boronic acid | A. Kuno et al. PCT Int. Appl. WO 9604241 |
| 4-n-Propyl-pyridin-3-yl-boronic acid | A. D. Borthwick et al. PCT Int. Appl. WO 2003053925 |
| (5-Propyl-thiophen-2-yl)-boronic acid | A. Seed et al. Liquid Crystals 2003, 30, 1089-1107 |
| Pyridin-3-yl-boronic acid | Fischer, F. C. et al. Recl. Trav. Chim. Pays-Bas 1974, 93, 21-24 |

In addition, many compounds of formula 10, where Y represents boronic acid, boronate ester, trimethyltin or tri-n-butyl-tin, are commercially available, including the following:

| Name | Supplier |
|---|---|
| 3-Acetamidobenzeneboronic acid | Aldrich Chemical Company, Inc., Milwaukee, WI |
| 4-Acetamidophenylboronic acid | Aldrich Chemical Company, Inc., Milwaukee, WI |
| 4-Acetamidophenylboronic acid | Apollo Scientific Ltd., Stockport, UK |
| (2-Aminocarbonylphenyl)boronic acid | Combi-Blocks Inc., San Diego, CA |
| (3-Aminocarbonylphenyl)boronic acid | Apollo Scientific Ltd., Stockport, UK |
| (4-Aminocarbonylphenyl)boronic acid | Apollo Scientific Ltd., Stockport, UK |
| 1-Benzyl-1H-pyrazole-4-boronic acid | Frontier Scientific, Inc., Logan, UT |
| 4-Benzyloxy-3-fluorobenzeneboronic acid | Lancaster Synthesis Ltd., Morecambe, UK |
| (2-Benzyloxy-4-fluorophenyl)boronic acid | ABCR GmbH &CO. KG, Karlsruhe, Germany |
| (2-Benzyloxyphenyl)boronic acid | Aldrich Chemical Company, Inc., Milwaukee, WI |
| 3-Benzyloxyphenylboronic acid | Aldrich Chemical Company, Inc., Milwaukee, WI |
| Biphenyl-3-boronic acid | Lancaster Synthesis Ltd., Morecambe, UK |
| 5-Bromopyridine-3-boronic acid | Lancaster Synthesis Ltd., Morecambe, UK |
| (3-Bromo-2-thienyl)-boronic acid | Rare Chemicals GmbH, Gettorf, Germany |
| 4-Bromo-2-thienylboronic acid | Acros Organics USA, Morris Plains, NJ |
| 5-Bromothiophene-2-boronic acid | Aldrich Chemical Company, Inc., Milwaukee, WI |
| 2-Chloro-5-fluoropyridine-3-boronic acid | Asymchem Laboratories, Inc., Durham, NC |
| 2-Chloropyridine-3-boronic acid | Lancaster Synthesis Ltd., Morecambe, UK |
| 2-Chloropyridine-5-boronic acid | Asymchem Laboratories, Inc., Durham, NC |
| 2-Chlorothiophene-3-boronic acid | Asymchem Laboratories, Inc., Durham, NC |
| 4-Chlorothiophene-2-boronic acid | Digital Specialty Chemicals, Inc., Dublin, NH |
| 5-Chlorothiophene-2-boronic acid | Aldrich Chemical Company, Inc., Milwaukee, WI |
| (2,6-Dichloro-3-pyridinyl)-boronic acid | Asymchem Laboratories, Inc., Durham, NC |
| 3,5-Dimethylisoxazole-4-boronic acid | Acros Organics USA, Morris Plains, NJ |
| 3,5-Dimethyl-4-(4,4,5,5-tetramethyl-1,3,2-dioxaborolan-2-yl)-1H-pyrazole | Boron Molecular Pty Ltd, Noble Park, Australia |
| 2-Fluoro-6-methylpyridine-3-boronic acid | Asymchem Laboratories, Inc., Durham, NC |
| 2-Fluoro-6-methylpyridine-5-boronic acid | Asymchem Laboratories, Inc., Durham, NC |
| 4-Fluoronaphthylene-1-boronic acid | Apollo Scientific Ltd., Stockport, UK |
| 2-Fluoropyridine-3-boronic acid | Lancaster Synthesis Ltd., Morecambe, UK |
| 2-Fluoropyridine-5-boronic acid | Frontier Scientific, Inc., Logan, UT |
| Furan-2-boronic acid | Aldrich Chemical Company, Inc., Milwaukee, WI |
| Furan-3-boronic acid | Aldrich Chemical Company, Inc., Milwaukee, WI |
| 5-Hydroxymethylfuran-2-boronic acid | Asymchem Laboratories, Inc., Durham, NC |
| 3-(Hydroxymethyl)phenylboronic acid | Aldrich Chemical Company, Inc., Milwaukee, WI |
| (2-Hydroxymethylphenyl)boronic acid dehydrate | Asymchem Laboratories, Inc., Durham, NC |
| 5-Hydroxymethylthiophene-2-boronic acid | Asymchem Laboratories, Inc., Durham, NC |
| 1-Isobutyl-4-(4,4,5,5-tetramethyl-1,3,2-dioxaborolan-2-yl)-1H-pyrazole | Boron Molecular Pty Ltd, Noble Park, Australia |
| 5-Isoquinolineboronic acid | Frontier Scientific, Inc., Logan, UT |
| 2-Methoxymethylphenylboronic acid | Apollo Scientific Ltd., Stockport, UK |
| 3-Methoxymethylphenylboronic acid | Digital Specialty Chemicals, Inc., Dublin, NH |
| 2-Methoxy-pyridine-3-boronic acid | Lancaster Synthesis Ltd., Lancashire, UK |
| 3,4-Methylenedioxybenzeneboronic acid | Aldrich Chemical Company, Inc., Milwaukee, WI |
| 4-Methyl-furan-2-boronic acid | Rare Chemicals GmbH, Gettorf, Germany |
| 5-Methylfuran-2-boronic acid | Aldrich Chemical Company, Inc., Milwaukee, WI |
| (4-Methyl-1-naphthalene)boronic acid | Aldrich Chemical Company, Inc., Milwaukee, WI |
| (4-Methyl-3-pyridinyl)-boronic acid | Synchem Laborgemeinschaft OHG, Kassel, Germany |
| (5-Methyl-3-pyridinyl)-boronic acid | Chontech, Inc., Waterford, CT |
| 8-Methyl-5-quinolineboronic acid | ACB Blocks Ltd., Moscow, Russia |

-continued

| Name | Supplier |
| --- | --- |
| 1-Methyl-4-(4,4,5,5-tetramethyl-1,3,2-dioxaborolan)-1H-pyrazole | Aldrich Chemical Company, Inc., Milwaukee, WI |
| 4-Methylthiophene-2-boronic acid | Acros Organics USA, Morris Plains, NJ |
| 4-Methylthiophene-3-boronic acid | Aldrich Chemical Company, Inc., Milwaukee, WI |
| 5-Methylthiophene-2-boronic acid | Aldrich Chemical Company, Inc., Milwaukee, WI |
| 1-Naphthaleneboronic acid | Aldrich Chemical Company, Inc., Milwaukee, WI |
| (2-Phenoxy)phenylboronic acid | Aldrich Chemical Company, Inc., Milwaukee, WI |
| 5-Phenyl-2-thienylboronic acid | Acros Organics USA, Morris Plains, NJ |
| Pyridine-3-boronic acid | Aldrich Chemical Company, Inc., Milwaukee, WI |
| 5-Quinolineboronic acid | Lancaster Synthesis Ltd., Morecambe, UK |
| 4-(4,4,5,5-Tetramethyl-1,3,2-dioxaborolan-2-yl)-1H-pyrazole | Aldrich Chemical Company, Inc., Milwaukee, WI |
| Thiophene-2-boronic acid | Aldrich Chemical Company, Inc., Milwaukee, WI |
| Thiophene-3-boronic acid | Aldrich Chemical Company, Inc., Milwaukee, WI |
| 2-(Trifluoromethoxy)benzeneboronic acid | Apin Chemicals Ltd., Abingdon, UK |
| 3-(Trifluoromethoxy)benzeneboronic acid | Aldrich Chemical Company, Inc., Milwaukee, WI |
| 4-(Trifluoromethoxy)benzeneboronic acid | Aldrich Chemical Company, Inc., Milwaukee, WI |
| Trimethyl(phenyl)tin | Aldrich Chemical Company, Inc., Milwaukee, WI |
| 3-(Tri-n-butylstannyl)pyridine | Maybridge plc, Tintagel, UK |
| Tri-n-butyl(2-thienyl)tin | Aldrich Chemical Company, Inc., Milwaukee, WI |

Compounds of formula 10, where Y represents boronic acid, boronate ester, trimethyltin or tri-n-butyl-tin, that are neither known in the literature nor commercially available can be synthesized by procedures that are well known to one skilled in the art of organic synthesis. For example, a compound of this type can conveniently be synthesized according to Scheme 8 from a compound of formula 14, in which X represents bromine or iodine, by treatment with an alkyllithium (e.g., n-butyllithium) or magnesium (to form the Grignard reagent) in a suitable inert solvent such as an ether (such as tetrahydrofuran or diethyl ether) at a temperature appropriate for the reaction (for example, at approximately −78 degrees for reaction with an alkyllithium, or at approximately room temperature for reaction with magnesium), followed by treatment with a trialkyl borate or trialkyltin chloride to form the compound of formula 10 where Y represents $B(OH)_2$ or trialkyltin, respectively.

Scheme 8

Additionally, the reaction can be carried out under noble metal catalysis. According to this route, the compound of formula-14 is conveniently reacted with a hexa-alkyl-distannane (such as hexamethyl-distannane or hexa-n-butyl-distannane) or 4,4,5,5-tetramethyl-[1,3,2]dioxaborolane or 4,4,5,5,4',4',5',5'-octamethyl-[2,2']bi[[1,3,2]dioxa-borolanyl], in the presence of a noble metal catalyst (preferably a palladium catalyst such as tetrakis(triphenylphosphine)palladium(0) or palladium(II) chloride or palladium (II) acetate), and in the optional additional presence of a catalytic amount of a phosphine ligand, for example tri-o-tolylphosphine or tri-tert-butylphosphine. In the case of reaction with a hexa-alkyl-distannane, the reaction is optionally carried out in the presence of an organic base, for example, a tertiary amine (e.g., triethylamine), while in the case of reaction with a dioxaborolane, the reaction is carried out in the presence of an inorganic base (e.g., cesium fluoride, or potassium acetate, preferably potassium acetate). The reaction is conveniently carried out in an appropriate inert solvent such as a polar aprotic solvent (e.g., N,N-dimethylformamide, N,N-dimethylacetamide, dimethylsulfoxide, or acetonitrile) or an aromatic hydrocarbon (e.g., toluene) at a temperature between about room temperature and about 100 degrees, and preferably at between about room temperature and about 50 degrees. As additional examples, the specific reaction conditions utilized in the following publications can be followed: O. Baudoin et al. *J. Org. Chem. Soc.* 2000, 65, 9268-9271; T. Ishiyama et al. *Tetrahedron Lett.* 1997, 38, 3447-3450; M. D. Hylarides *J. Organomet. Chem.* 1989, 367, 259-265; M. W. Read et al. *Org. Lett.* 2000, 2, 3201-3204; T. Ishiyama et al. *Tetrahedron* 1997, 57, 9813-9816; A. Fuerster et al. *Org. Lett.* 2002, 4, 541-544.

Acylated Amino Acids

As shown in Scheme 9, a compound of the invention of formula 1 where $R^4$ represents a hydroxy group can be converted to a compound of formula 1 where $R^4$ represents an amino acid attached through a nitrogen atom of the amino acid. This reaction can be carried out using a variety of procedures that are well known in the field of organic synthesis, and especially well known in the field of peptide synthesis. The reaction is typically carried out in two steps. First, the compound of formula 1 where $R^4$ represents a hydroxy group is reacted with a suitably protected amino acid to give an intermediate of formula 1 where $R^4$ represents a protected amino acid, and subsequently the protective group is removed to give the compound of formula 1 where $R^4$ represents an amino acid attached through a nitrogen atom of the amino acid. Many examples of suitable protective groups for the amino acid are known to those of skill in the art of organic synthesis. For example, several suitable protective groups are enumerated in "Protective Groups in Organic Synthesis" [T. W. Greene and P. G. M. Wuts, $2^{nd}$ Edition, John Wiley & Sons, N.Y. 1991]. Preferred protective groups are those compatible with the reaction conditions used to prepare compounds of the invention. Examples of such protective groups are lower alkyl straight-chain or branched esters (e.g., the methyl, the ethyl, or the tert-butyl ester), or the benzyl ester.

Scheme 9

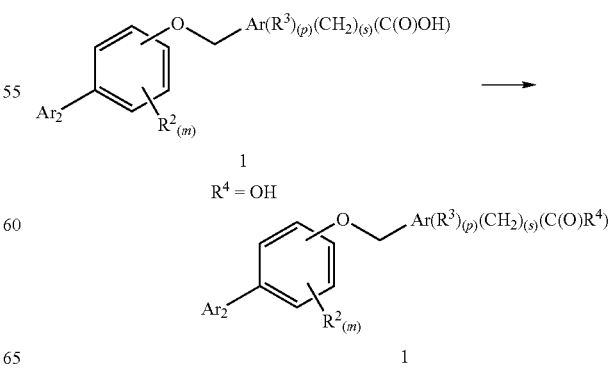

For example, the first reaction can be carried out by treating the compound of formula 1 in which $R^4$ represents a hydroxy group, with a protected amino acid in the presence of a coupling agent, many examples of which are well known per se in peptide chemistry, and in the optional presence of a substance that increases the rate of the reaction, such as 1-hydroxybenzotriazole or 1-hydroxy-7-azabenzo-triazole; or by reaction of the protected amino acid with a reactive derivative of the compound of formula 1 in which $R^4$ represents a hydroxy group such as the corresponding acid halide (for example, the acid chloride), acid anhydride, mixed anhydride, activated ester etc. The reaction is conveniently carried out by treating the protected amino acid with the compound of formula 1 in which $R^4$ represents a hydroxy group in the presence of a carbodiimide reagent such as diisopropyl carbodiimide and 1-hydroxy-7-azabenzotriazole in an inert solvent such as N,N-dimethylformamide or N-methylpyrrolidinone at a temperature between about 0 degrees and about room temperature, preferably at about room temperature.

The removal of the protective group from the compound of formula 1 in which $R^4$ represents a protected amino acid attached through a nitrogen atom of the amino acid can be effected using one of several choices of reactions conditions, the selection of which will depend on the nature of the protective group, and the other functionality present in the compound of formula 1. Many suitable reaction conditions are outlined in "Protective Groups in Organic Synthesis" [T. W. Greene and P. G. M. Wuts, 2nd Edition, John Wiley & Sons, N.Y. 1991]. For example, in the case where the protective group is methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature. As another example, in the case where the protective group is a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0 degrees and about room temperature, preferably at about room temperature. As a final (but not limiting) example, in the case where the protective group is a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

EXAMPLES

The following examples illustrate preferred methods for synthesizing the compounds and formulations of the present invention.

The purity of the exemplified compounds was determined by analytical HPLC. Where the purity of the compound did not exceed 85 percent as judged by UV absorption at 214 nm, the compound was purified by preparative HPLC. The conditions for analytical and preparative HPLC are given below.

Analytical HPLC

Analytical HPLC was carried out with a Waters 600 LC pump and Supelco Discovery C18 column (5 µm, 50 mm×4.6 mm). Mobile phases A (0.1% formic acid in water) and B (0.1% formic acid in acetonitrile) were used in a gradient of 5% B rising to 98% B after 5 mins, held for 4 min at a flow rate of 2 mL/min. Photo-diode array (PDA) detection was by a Waters 996 Photodiode Array Detector, range 210-400 nm UV and ELS detection with a Polymer Laboratories PL-ELS 1000 (Nitrogen flow rate 1.3 L/min. Nebulizer temp. 80° C., Evap. temp. 110° C.). The Mass spectrometer was a Micromass ZQ operating in electrospray ionization mode.

Preparative HPLC

Samples that required purification were purified with a Waters mass-directed purification system utilizing a Waters 600 LC pump, Waters Xterra C18 column (5 µm, 19 mm×50 mm) and Micromass ZQ mass spectrometer, operating in positive ion electrospray ionization mode. Mobile phases A (0.1% formic acid in water) and B (0.1% formic acid in acetonitrile) were used in a gradient; 5% B to 30% B over 7 mins, held for 1 min, at a flow rate of 20 mL/min.

Intermediate 1: 3-(4-Iodo-phenoxymethyl)-benzoic acid methyl ester

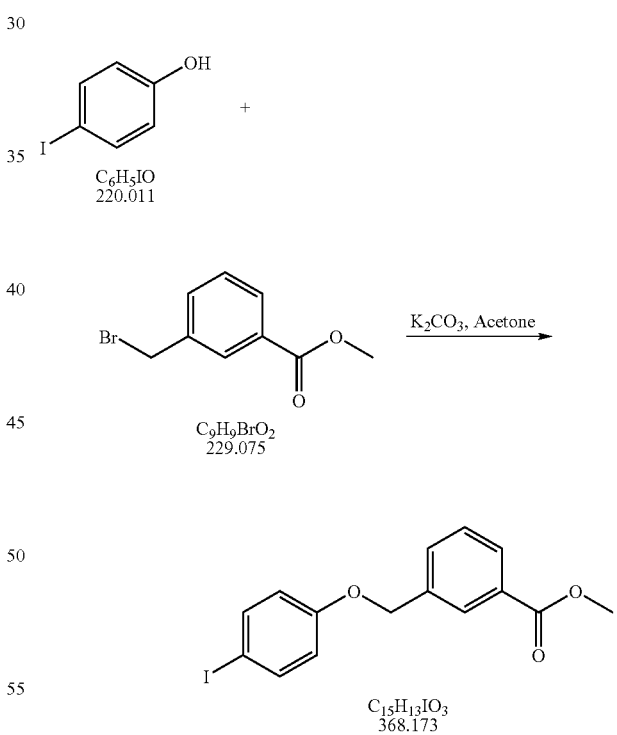

Freshly ground potassium carbonate (8.3 g, 60 mmol) was added to a solution of methyl 3-bromomethyl-benzoate (12.83 g, 56 mmol; available from Lancaster Synthesis Ltd., Lancashire, UK) and 4-iodophenol (13.2 g, 60 mmol; available from Aldrich Chemical Company, Inc., Milwaukee, Wis.) in acetone (600 mL). The reaction mixture was heated at reflux overnight and then it was filtered and water was added. The resulting white solid was filtered off and dried in a vacuum oven overnight to give 3-(4-iodo-phenoxymethyl)-benzoic acid methyl ester (18.63 g, 90%) as a white solid Intermediate 2:
2-(4-Iodo-phenoxymethyl)-thiazole-4-carboxylic acid ethyl ester

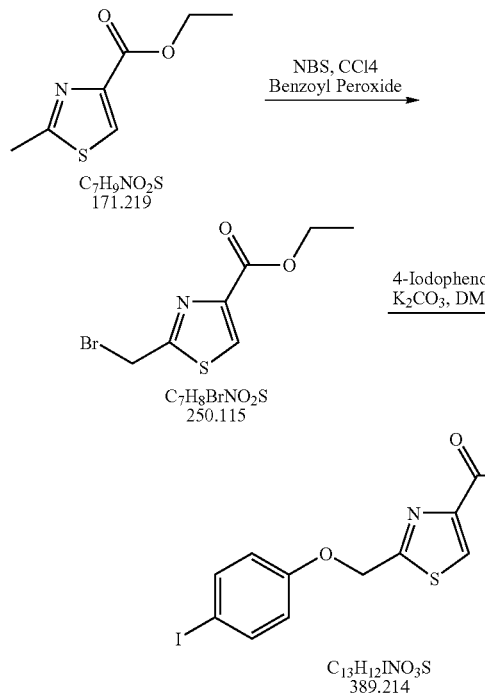

Step 1: 2-Bromomethyl-thiazole-4-carboxylic acid ethyl ester

2-Bromomethyl-thiazole-4-carboxylic acid ethyl ester was prepared according to N. Kindon et al. (U.S. Pat. No. 6,162,808): A mixture of 2-methyl-thiazole-4-carboxylic acid (available from Maybridge plc, Tintagel, UK; 9.8 g, 57.2 mmol), benzoyl peroxide (40 mg, 0.165 mmol) and NBS (10.6 g, 60.0 mmol) in carbon tetrachloride (250 mL) was heated at reflux over the weekend. The reaction mixture was cooled to room temperature and evaporated under reduced pressure. The crude material was partitioned between ethyl acetate and water. The organic layer was dried (magnesium sulfate), filtered, evaporated, and purified by chromatography on flash silica gel, eluting with 20% ethyl acetate/hexane to give 2-bromomethyl-thiazole-4-carboxylic acid ethyl ester (4.4 g, 31%) as an orange oil. $^1$HNMR (CDCl$_3$): δ 9.23 (s, 1H), 4.77 (s, 2H), 4.44 (q, J=7.0 Hz, 2H), 1.41 (t, J=7.0 Hz, 3H). MS (APCl+): 252 (100), 250 (90).

Step 2: 2-(4-Iodo-phenoxymethyl)-thiazole-4-carboxylic acid ethyl ester

Ground potassium carbonate (3.4 g, 24.6 mmol) was added to a solution of 2-bromomethyl-thiazole-4-carboxylic acid ethyl ester (12.83 g, 56 mmol; from Step 1 above) and 4-iodophenol (5.5 g, 25 mmol; available from Aldrich Chemical Company, Inc., Milwaukee, Wis.) in acetone (440 mL). The reaction mixture was heated at reflux for 15 h and then it was filtered and water was added to the filtrate until it turned cloudy. The filtrate was left on ice and then the resulting white solid was filtered off, washed with acetone/hexanes (2:1) and dried to give 2-(4-iodo-phenoxymethyl)-thiazole-4-carboxylic acid ethyl ester (5.6 g, 65%) as a white solid. $^1$HNMR (CDCl$_3$): δ 1.4 (t, 3H, J=7 Hz), 4.46 (q, 2H, J=7 Hz), 5.4 (s, 2H), 6.7 (d, 2H, J=9 Hz), 7.6 (d, 2H, J=9 Hz), 8.2 (s, 1H).

Intermediate 3:
6-(4-Iodo-phenoxymethyl)-pyridine-2-carboxylic acid ethyl ester

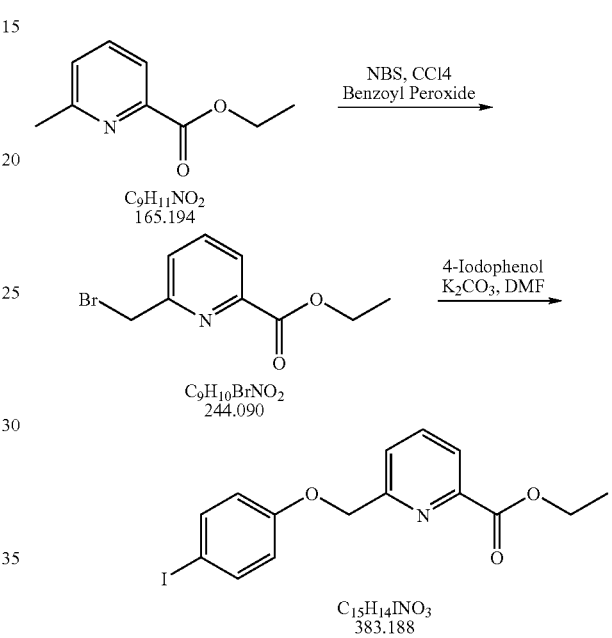

Step 1: 6-Bromomethyl-pyridine-2-carboxylic acid ethyl ester

Finely ground N-bromo-succinimide (29.4 g, 165.2 mmol) was added in several portions to a solution of 6-methyl-pyridine-2-carboxylic acid ethyl ester (24.7 g, 150.0 mmol; available from Aldrich Chemical Company, Inc., Milwaukee, Wis.) in carbon tetrachloride (500 mL), and then benzoyl peroxide (100 mg, 0.4 mmol) was added. The mixture was heated at 84 degrees under nitrogen for approximately 40 h. Further portions of N-bromo-succinimide (14.8 g, 83.2 mmol) and then benzoyl peroxide (100 mg, 0.4 mmol) were added and heating was continued overnight. The reaction mixture was cooled to room temperature, filtered, evaporated, and purified by chromatography on silica gel using a Biotage system, eluting with 1:1 dichloromethane/hexane and dichloromethane to give 6-bromomethyl-pyridine-2-carboxylic acid ethyl ester (11.8 g, 32%) as a pale yellow oil. MS (MH+): 244/246. From HPLC, the purity was estimated at 85-90% and the material was used in the next step without further purification.

Step 2: 6-(4-Iodo-phenoxymethyl)-pyridine-2-carboxylic acid ethyl ester

6-Bromomethyl-pyridine-2-carboxylic acid ethyl ester (1:1.72 g, 48 mmol; from Step 1 above) was dissolved in acetone (250 mL) and 4-iodophenol (11.61 g, 52.8 mmol; available from Aldrich Chemical Company, Inc., Milwaukee, Wis.) was added, followed by potassium carbonate (7.55 g, 54.6 mmol). The mixture was heated overnight at 65 degrees, and it was then cooled and filtered. The solid was washed with small portions of acetone and the filtrate was concentrated to approximately 100 mL by evaporation. The solution was warmed and then diluted with water (approximately 70 mL). The resulting brown solution was cloudy and started to precipitate an oily solid. The mixture was scratched with a spatula and allowed to cool to room temperature. The off-white precipitate was filtered off, washed with several portions of acetone/water (1:1), and then dried in vacuo over phosphorus pentoxide to give 6-(4-iodo-phenoxymethyl)-pyridine-2-carboxylic acid ethyl ester (13.72 g, 75%) as an off-white crystalline solid. MS (MH+) 384. $^1$HNMR (CDCl$_3$): δ 1.47 (t, 3H, J=7 Hz), 4.52 (q, 2H, J=7 Hz), 5.33 (s, 2H), 6.78 (d, 2H, J=9 Hz), 7.58 (d, 2H, J=9 Hz), 7.74 (d, 1H, J=7.8 Hz), 7.91 (dd, 1H, J=7.8, 7.8 Hz), 8.09 (d, 1H, J=7.8 Hz).

Intermediate 4:
[3-(4-Iodo-phenoxymethyl)-phenyl]-acetic acid ethyl ester

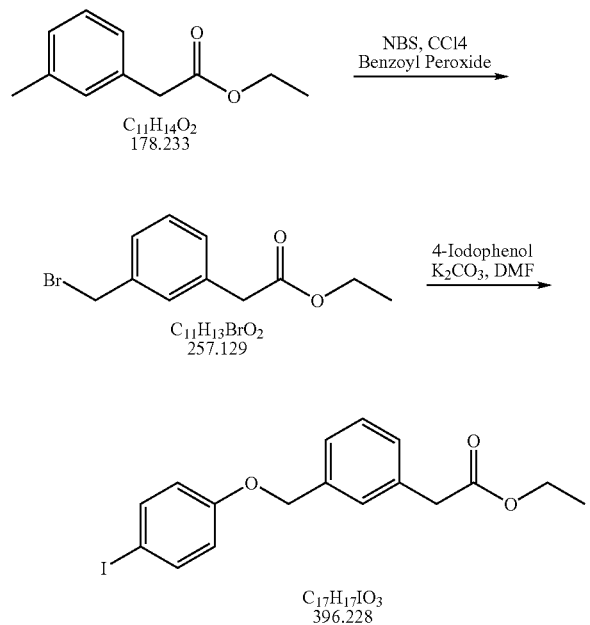

Step 1: (3-Bromomethyl-phenyl)-acetic acid ethyl ester

A mixture of N-bromo-succinimide (10.68 g, 60.0 mmol), m-tolyl-acetic acid ethyl ester (10.0 g, 56.1 mmol; available from Aldrich Chemical Company, Inc., Milwaukee, Wis.) and benzoyl peroxide (40 mg, 0.17 mmol) in carbon tetrachloride (250 mL) was heated at reflux under nitrogen for 36 h. The reaction mixture was filtered, evaporated, and purified by chromatography on silica gel, eluting with 0-100% dichloromethane in hexane to give (3-bromomethyl-phenyl)-acetic acid ethyl ester (4.79 g, 33%). MS m/z 257. $^1$HNMR (DMSO-d$_6$): δ 7.2-7.35 (m, 4H), 4.50 (s, 2H), 4.18 (q, 2H), 3.62 (s, 2H), 1.28 (t, 3H).

Step 2: [3-(4-Iodo-phenoxymethyl)-phenyl]-acetic acid ethyl ester (3-Bromomethyl-phenyl)-acetic acid ethyl ester (4.37 g, 17.0 mmol; from Step 1 above) was dissolved in acetone (100 mL) and 4-iodophenol (4.11 g, 18.7 mmol; available from Aldrich Chemical Company, Inc., Milwaukee, Wis.) was added, followed by potassium carbonate (2.66 g, 19.3 mmol). The mixture was heated overnight at reflux, and it was then combined with material from an earlier run using the same conditions but on a 2 mmol scale. The combined materials were cooled and filtered. The solid was washed with acetone and the filtrate was evaporated to give an oil (8 g). The solution was purified by chromatography using a Biotage system with an S90 cartridge, eluting with 0-50% dichloromethane in hexane to give [3-(4-iodo-phenoxymethyl)-phenyl]-acetic acid ethyl ester (4.3 g, 57%). $^1$HNMR (CDCl$_3$): δ 1.26 (t, 3H, J=7 Hz), 3.65 (s, 2H), 4.16 (q, 2H, J=7 Hz), 5.04 (s, 2H), 6.76 (d, 2H, J=9 Hz), 7.26-7.37 (m, 4H+solvent), 7.57 (d, 2H, J=9 Hz).

Intermediate 5:
6-(4-Iodo-phenoxymethyl)-pyridine-2-carboxylic acid methyl ester

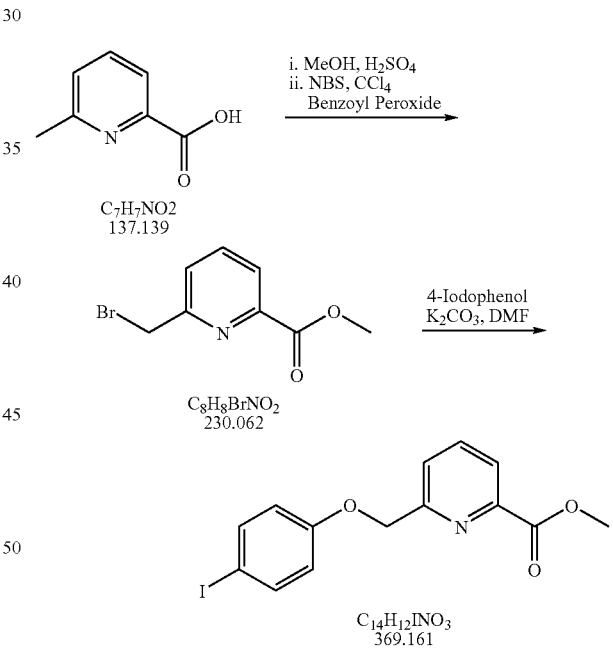

Step 1: 6-Methyl-pyridine-2-carboxylic acid methyl ester

Concentrated sulfuric acid (5 mL) was added cautiously with stirring to a suspension of 6-methyl-pyridine-2-carboxylic acid (available from Aldrich Chemical Company, Inc., Milwaukee, Wis.; 7.00 g, 51 mmol) in methanol (approximately 250 mL). The mixture was heated at reflux overnight (with a calcium chloride drying tube) and then the solution was concentrated almost to dryness. A little water was added and then aqueous sodium bicarbonate was added to bring the pH to 8. The solution was extracted with ethyl acetate (2×100 mL) and the extracts were washed with brine, then dried (magnesium sulfate), filtered, and evaporated to give 6-methyl-pyridine-2-carboxylic acid methyl ester (3.53 g, 46%) as a pale yellow oil. Mass spectrum m/z 152.

Step 2: 6-Bromomethyl-pyridine-2-carboxylic acid methyl ester

N-Bromosuccinimide (4.9 g, 27.3 mmol) was added in portions to a stirred solution of 6-methyl-pyridine-2-carboxylic acid methyl ester (3.90 g, 25.8 mmol) in carbon tetrachloride (100 mL). Dibenzoyl peroxide (20 mg) was added and the mixture was heated in an oil bath at 85 degrees for two days. TLC (eluting with dichloromethane) showed that there was unreacted starting material in addition to two new spots, so further quantities of N-bromosuccinimide (1.1 g, 6.1 mmol) and dibenzoyl peroxide (20 mg) were added and the reaction mixture was heated at reflux for 24 hours, and then filtered to remove succinimide. The filtrate was evaporated to give an oil that was chromatographed on silica gel (Biotage 90) eluting with 0-100% dichloromethane/hexanes to give 6-bromomethyl-pyridine-2-carboxylic acid methyl ester (2.27 g, 38%) as a crystalline solid. Mass spectrum m/z 230/232.

Step 3: 6-(4-Iodo-phenoxymethyl)-pyridine-2-carboxylic acid methyl ester

6-Bromomethyl-pyridine-2-carboxylic acid methyl ester (2.27 g, 9.9 mmol; from Step 2 above) was dissolved in acetone (50 mL) and 4-iodophenol (2.37 g, 10.8 mmol; available from Aldrich Chemical Company, Inc., Milwaukee, Wis.) was added, followed by finely ground potassium carbonate (1.54 g, 11.2 mmol). The mixture was heated overnight at 60 degrees, and it was then cooled and filtered. The solid was washed with acetone and the filtrate was concentrated to dryness. Ethyl acetate (100 mL) was added and the solution was washed twice with 2 M NaOH, with water, and with brine. The solution was dried (magnesium sulfate), filtered and evaporated to give the crude product. This was dissolved in acetone (approximately 25 mL) with warming, and water (approximately 20 mL) was added. An oil came out of solution and it crystallized. The mixture was heated to redissolve the solid and the solution was seeded with a crystal of the product to give crystals of the product. The recrystallization was repeated to give 6-(4-iodo-phenoxymethyl)-pyridine-2-carboxylic acid methyl ester (2.24 g, 62%) as a white crystalline solid. Mass spectrum m/z 370.

General Procedure 1 for the Preparation of 3-Biaryloxymethyl-benzoic Acids

A stock solution was prepared consisting of 3-(4-iodo-phenoxymethyl)-benzoic acid methyl ester (of intermediate 1; 962 mg, 2.6 mmol), potassium carbonate (1079 mg, 7.8 mmol), bis(tri-cyclohexylphosphine)palladium (available from Strem Chemicals, Inc., Newburyport, Mass.; 91 mg, 0.14 mmol), water (approximately 5.8 mL), and dioxane (approximately 58 mL). The solution was sonicated and degassed by bubbling nitrogen gas through it. A portion of this solution (4.5 mL) was added to each of a number of tubes containing an aryl-boronic acid. The mixtures were each heated in a microwave oven at 170 degrees for 25 min. The mixtures were filtered in parallel with silica cartridges and washed with dioxane (1 mL) and dimethylacetamide (1 mL). The filtrates were placed in vials and 2 M potassium hydroxide solution (0.4 mL) was added to each vial. The mixtures were stirred at room temperature overnight, then 1 M HCl (0.8 mL) was added to each vial and the solvents were evaporated using a Genevac system. Aqueous methanol (50%; approximately 2 mL) was added to each vial, then the vials were centrifuged and the solvent was removed. This process was repeated and then the samples were dried overnight in the oven.

General Procedure 2 for the Preparation of 2-Biaryloxymethyl-thiazole-4-carboxylic Acids A first stock solution was prepared consisting of 2-(4-iodo-phenoxymethyl)-thiazole-4-carboxylic acid ethyl ester (of intermediate 2; 1.87 g, 4.8 mmol), bis(tri-cyclohexyl-phosphine)palladium (available from Strem Chemicals, Inc., Newburyport, Mass.; 168 mg, 0.25 mmol), and dioxane (approximately 100 mL). A second stock solution was prepared consisting of potassium carbonate (1.99 g, 14.4 mmol) and water (approximately 10 mL). The solutions were sonicated and degassed by bubbling nitrogen gas through them. 4 mL of the first stock solution and 0.4 mL of the second stock solution were added to each of a number of tubes containing an aryl-boronic acid. The mixtures were each heated in a microwave oven at 170 degrees for 25 min. 1 M HCl (0.1 mL) was added to each vial, and the solution were passed through silica gel columns (1 g of silica), and washed with dimethylacetamide (2×1 mL). The solutions were evaporated to dryness and triturated with aqueous methanol (2×2 mL) to give the product.

General Procedure 3 for the Preparation of 6-Biaryloxymethyl-pyridine-2-carboxylic Acids A first stock solution was prepared consisting of 6-(4-iodo-phenoxymethyl)-pyridine-2-carboxylic acid ethyl ester (of intermediate 3; 1.85 g, 4.8 mmol), bis(tri-cyclohexyl-phosphine)palladium (available from Strem Chemicals, Inc., Newburyport, Mass.; 168 mg, 0.25 mmol), and dioxane (approximately 96 mL). A second stock solution was prepared consisting of potassium carbonate (1.99 g, 14.4 mmol) and water (approximately 9.6 mL). The solutions were sonicated and degassed by bubbling nitrogen gas through them. 4 mL of the first stock solution and 0.4 mL of the second stock solution were added to each of a number of tubes containing an aryl-boronic acid. The mixtures were each heated in a microwave oven at 170 degrees for 25 min, then filtered through a 20 micron polyethylene filter and washed with dimethylacetamide (2×1 mL). The crude products were purified by preparative HPLC (see above for conditions). Fractions containing the purified product were evaporated to dryness using a Genevac system.

General Procedure 4 for the Preparation of 3-Biaryloxymethyl-phenylacetic Acids

A first stock solution was prepared consisting of [3-(4-iodo-phenoxymethyl)-phenyl]-acetic acid ethyl ester (of intermediate 4; 1.89 g, 4.8 mmol), bis(tri-cyclohexyl-phosphine)palladium (available from Strem Chemicals, Inc., Newburyport, Mass.; 168 mg, 0.25 mmol), and dioxane (approximately 96 mL). This solution was sonicated and degassed by bubbling nitrogen gas through it. A second stock solution was prepared consisting of potassium carbonate (1.99 g, 14.4 mmol) and water (approximately 9.6 mL). 4 mL of the first stock solution and 0.4 mL of the second stock solution were added to each of a number of tubes containing an aryl-boronic acid. The mixtures were each heated in a microwave oven at 170 degrees for 25 min. To each reaction mixture was added 1 M KOH solution (0.8 mL, 0.8 mmol) and the solutions were heated at 60 degrees overnight. 1 M HCl (0.8 mL, 0.8 mmol) was added to each solution and the reactions were then filtered through silica (1 g) and washed with dimethylacetamide. The solutions were evaporated to dryness using a Genevac system and further dried in the vacuum oven at 50 degrees.

General Procedure 5 for the Preparation of 3-Biaryloxymethyl-phenylacetic Acids

A first stock solution was prepared consisting of [3-(4-iodo-phenoxymethyl)-phenyl]-acetic acid ethyl ester (of intermediate 4; 1.89 g, 4.8 mmol), bis(tri-cyclohexyl-phosphine)palladium (available from Strem Chemicals, Inc., Newburyport, Mass.; 168 mg, 0.25 mmol), and dioxane (approximately 96 mL). This solution was sonicated and degassed by bubbling nitrogen gas through it. A second stock solution was prepared consisting of potassium carbonate (1.99 g, 14.4 mmol) and water (approximately 9.6 mL). 4 mL of the first stock solution and 0.4 mL of the second stock solution were added to each of a number of tubes containing an aryl-boronic acid. The mixtures were each heated in a microwave oven at 170 degrees for 25 min. To each reaction mixture was added 2 M KOH solution (0.4 mL, 0.8 mmol) and the solutions were heated at 65 degrees overnight. 2 M HCl (0.4 mL, 0.8 mmol) was added to each solution and the reactions were then filtered through silica (3 g). The solutions were evaporated to dryness using a Genevac system and the resulting solids were triturated with 50% aqueous methanol (2×2 mL) to give the products.

Example 1

3-(3'-Acetylamino-biphenyl-4-yloxymethyl)-benzoic acid

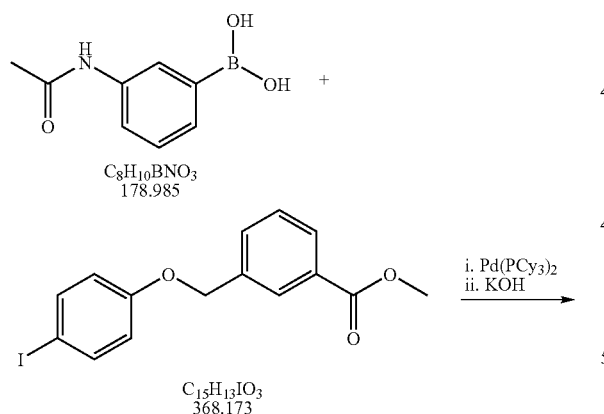

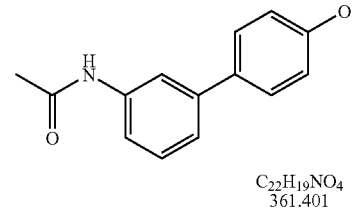

3-(3'-Acetylamino-biphenyl-4-yloxymethyl)-benzoic acid was prepared using general procedure 1 from 3-(4-iodo-phenoxymethyl)-benzoic acid methyl ester (of Intermediate 1) and 3-acetamidobenzeneboronic acid (ASDI Incorporated, Newark, Del.). Mass spectrum MH+=362.

Example 2

3-(4-Benzo[1,3]dioxol-5-yl-phenoxymethyl)-benzoic acid

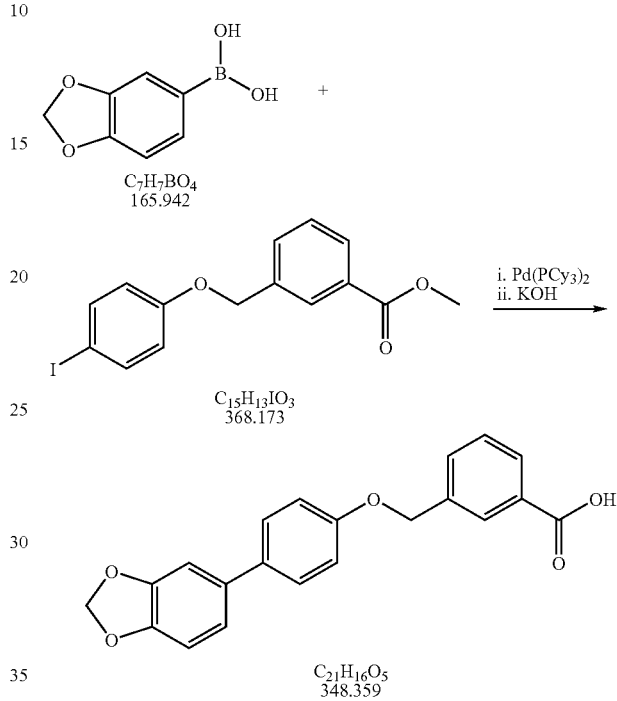

3-(4-Benzo[1,3]dioxol-5-yl-phenoxymethyl)-benzoic acid was prepared using general procedure 1 from 3-(4-iodo-phenoxymethyl)-benzoic acid methyl ester (of Intermediate 1) and 3,4-methylenedioxybenzeneboronic acid (ASDI Incorporated, Newark, Del.). Mass spectrum MH+=349.

Example 3

3-(3'-Carbamoyl-biphenyl-4-yloxymethyl)-benzoic acid

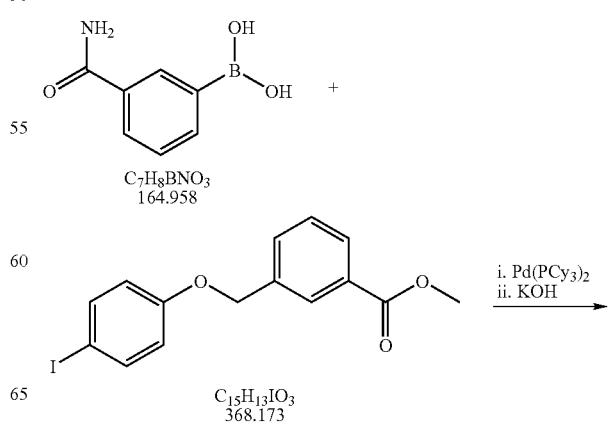

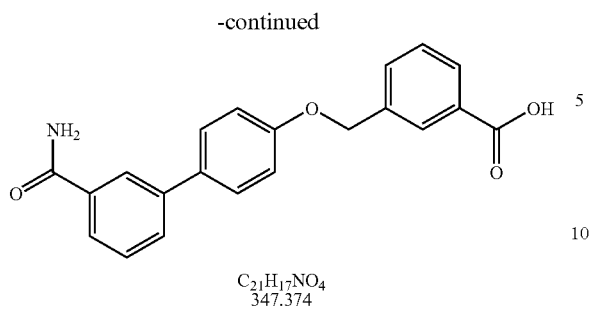

C₂₁H₁₇NO₄
347.374

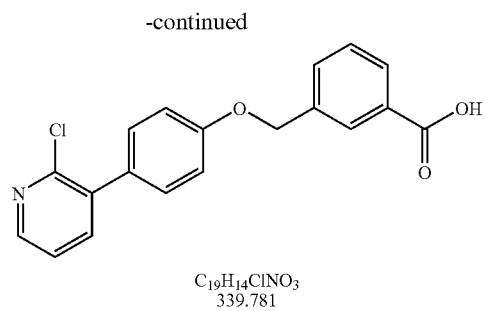

C₁₉H₁₄ClNO₃
339.781

A first stock solution was prepared consisting of 3-(4-iodo-phenoxymethyl)-benzoic acid methyl ester (of Intermediate 1; 1.11 g, 3 mmol), bis(tri-cyclohexyl-phosphine)palladium (available from Strem Chemicals, Inc., Newburyport, Mass.; 105 mg, 0.16 mmol), and dioxane (approximately 62 mL). A second stock solution was prepared consisting of potassium carbonate (1.245 g, 9 mmol) and water (approximately 6.2 mL). The solutions were sonicated and degassed by bubbling nitrogen gas through them. 4 mL of the first stock solution and 0.4 mL of the second stock solution were added to a reaction vial containing (3-aminocarbonylphenyl)boronic acid (available from Apollo Scientific Ltd., Stockport, UK; 99 mg, 0.6 mmol). The mixture was heated in a microwave oven at 170 degrees for 25 min and then passed through a silica gel column (1 g of silica), and washed with dioxane (1 mL) and dimethylacetamide (1 mL). 2 M potassium hydroxide solution (0.4 mL) was added. The mixture was stirred at room temperature overnight, and then 1 M HCl (0.8 mL) was added and the solvents were removed in the Genevac. Aqueous methanol (50%; approximately 2 mL) was added, then the vial was centrifuged and the solvent was removed. This process was repeated to give 3-(3'-carbamoyl-biphenyl-4-yloxymethyl)-benzoic acid. Mass spectrum MH+=348.

A first stock solution was prepared consisting of 3-(4-iodo-phenoxymethyl)-benzoic acid methyl ester (of Intermediate 1; 1.77 g, 4.8 mmol), bis(tri-cyclohexyl-phosphine)palladium (available from Strem Chemicals, Inc., Newburyport, Mass.; 168 mg, 0.25 mmol), and dioxane (approximately 100 mL). A second stock solution was prepared consisting of potassium carbonate (1.99 g, 14.4 mmol) and water (approximately 10 mL). The solutions were sonicated and degassed by bubbling nitrogen gas through them. 4 mL of the first stock solution and 0.4 mL of the second stock solution were added to a reaction vial containing 2-chloropyridine-3-boronic acid (ASDI Incorporated, Newark, Del.; 94 mg, 0.6 mmol). The mixture was heated in a microwave oven at 170 degrees for 25 min and then passed through a silica gel column (1 g of silica), and washed with dioxane (1 mL) and dimethylacetamide (1 mL). 2 M potassium hydroxide solution (0.4 mL) was added. The mixture was stirred at room temperature overnight, and then 1 M HCl (0.8 mL) was added and the solvents were removed in the Genevac. Aqueous methanol (50%; approximately 2 mL) was added, then the vial was centrifuged and the solvent was removed. This process was repeated and then the sample was dried overnight in the oven to give 3-[4-(2-chloro-pyridin-3-yl)-phenoxymethyl]-benzoic acid. Mass spectrum MH+=340.

Example 4

3-[4-(2-Chloro-pyridin-3-yl)-phenoxymethyl]-benzoic acid

Example 5

3-[4-(6-Chloro-pyridin-3-yl)-phenoxymethyl]-benzoic acid

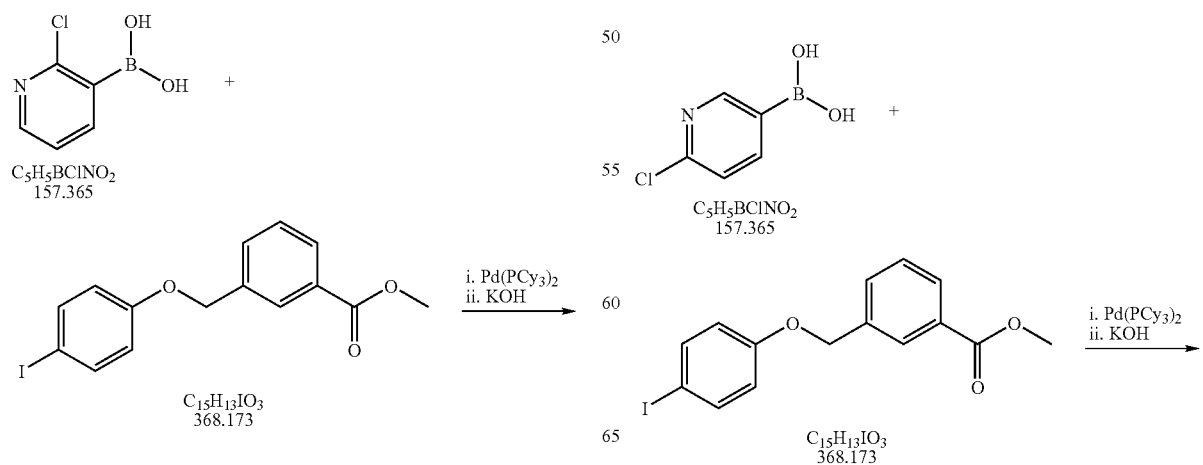

-continued

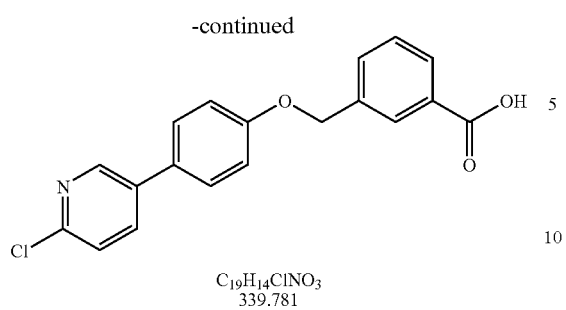

C₁₉H₁₄ClNO₃
339.781

3-[4-(6-Chloro-pyridin-3-yl)-phenoxymethyl]-benzoic acid was prepared using the procedure described above for the synthesis of Example 4 from 3-(4-iodo-phenoxymethyl)-benzoic acid methyl ester (of Intermediate 1) and 2-chloro-pyridine-5-boronic acid (ASDI Incorporated, Newark, Del.). Mass spectrum MH+=340.

Example 6

3-[4-(3,5-Dimethyl-isoxazol-4-yl)-phenoxymethyl]-benzoic acid

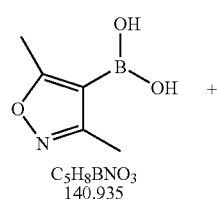

C₅H₈BNO₃
140.935

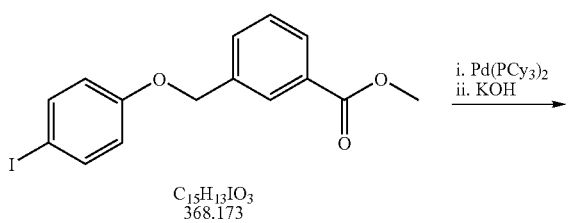

C₁₅H₁₃IO₃
368.173 i. Pd(PCy₃)₂
ii. KOH

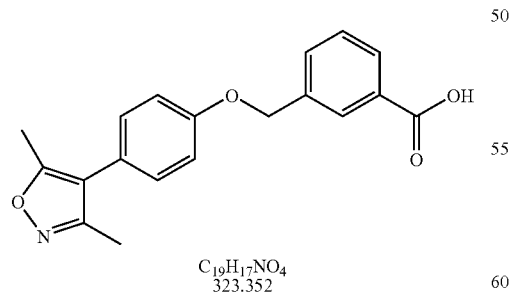

C₁₉H₁₇NO₄
323.352

3-[4-(3,5-Dimethyl-isoxazol-4-yl)-phenoxymethyl]-benzoic acid was prepared using general procedure 1 from 3-(4-iodo-phenoxymethyl)-benzoic acid methyl ester (of Intermediate 1) and 3,5-dimethylisoxazole-4-boronic acid (ASDI Incorporated, Newark, Del.). Mass spectrum MH+=324.

Example 7

3-[4-(2-Fluoro-pyridin-3-yl)-phenoxymethyl]-benzoic acid

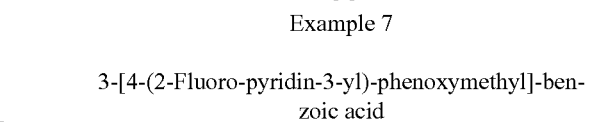

C₅H₅BFNO₂
140.910

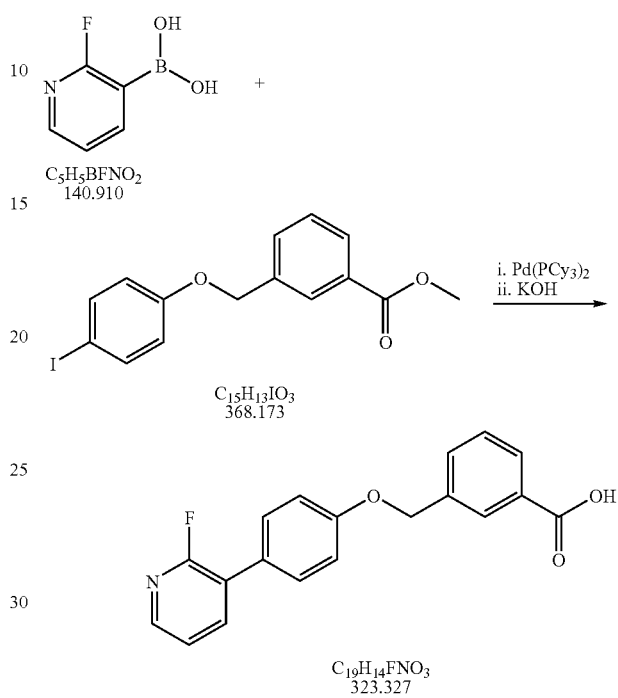

C₁₅H₁₃IO₃
368.173 i. Pd(PCy₃)₂
ii. KOH

C₁₉H₁₄FNO₃
323.327

3-[4-(2-Fluoro-pyridin-3-yl)-phenoxymethyl]-benzoic acid was prepared using the procedure described above for the synthesis of Example 4 from 3-(4-iodo-phenoxymethyl)-benzoic acid methyl ester (of Intermediate 1) and 2-fluoro-pyridine-3-boronic acid (ASDI Incorporated, Newark, Del.). Mass spectrum MH+=324.

Example 8

3-[4-(6-Fluoro-pyridin-3-yl)-phenoxymethyl]-benzoic acid

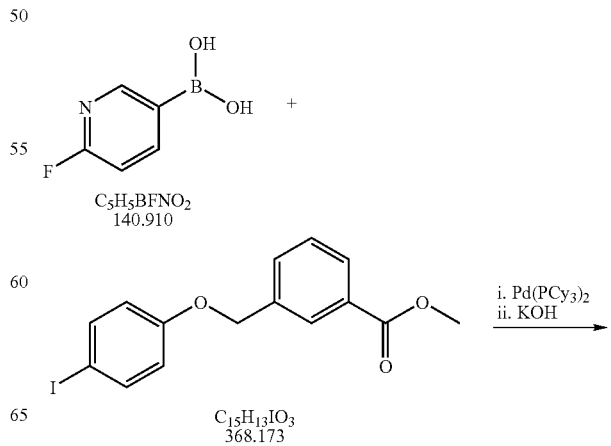

C₅H₅BFNO₂
140.910

C₁₅H₁₃IO₃
368.173 i. Pd(PCy₃)₂
ii. KOH

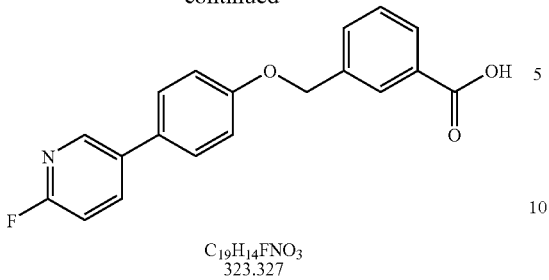

3-[4-(6-Fluoro-pyridin-3-yl)-phenoxymethyl]-benzoic acid was prepared using the procedure described above for the synthesis of Example 4 from 3-(4-iodo phenoxymethyl)-benzoic acid methyl ester (of Intermediate 1) and 2-fluoro-pyridine-5-boronic acid (ASDI Incorporated, Newark, Del.). Mass spectrum MH+=324.

Example 9

3-(4-Furan-2-yl-phenoxymethyl)-benzoic acid

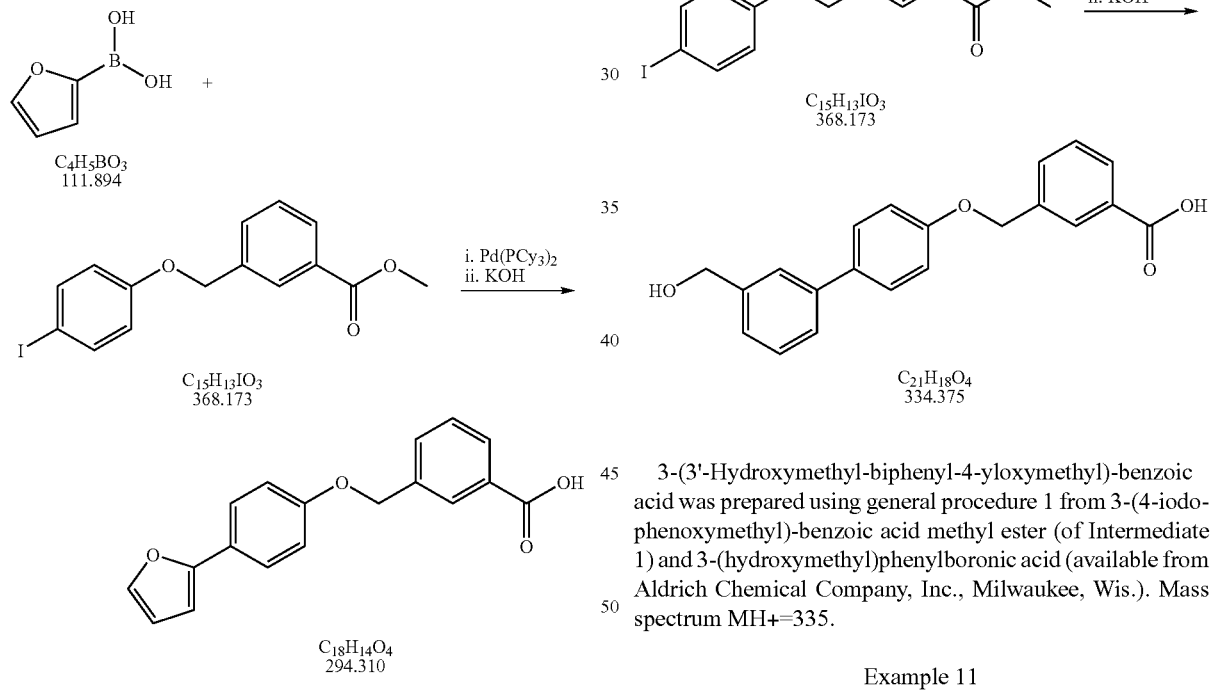

A solution of 3-(4-iodo-phenoxymethyl)-benzoic acid methyl ester (of intermediate 1; 74 mg, 0.2 mmol) in dioxane/water (10:1, 4.4 mL) was degassed for 20 min and then added to a reaction vial containing potassium carbonate (82 mg, 0.6 mmol) and furan-2-boronic acid (0.6 mmol; available from Aldrich Chemical Company, Inc., Milwaukee, Wis.). The solution was degassed for a further 2 min and then bis(tricyclohexylphosphine)palladium (available from Strem Chemicals, Inc., Newburyport, Mass.; 14 mg, 0.02 mmol) was added. The mixture was degassed for 30 seconds and then heated in a microwave oven at 170 degrees for 25 min. The reaction mixture was filtered through silica and the silica washed with dioxane (1 mL), dimethylacetamide (1 mL), and 20% methanol in dichloromethane (1 mL). The filtrate was placed in a vial and 2 M potassium hydroxide solution (0.4 mL) was added. The mixture was stirred at room temperature overnight, and then 1 M HCl was added until a solid formed (approxiamtely 2 mL). The vial was centrifuged and the solvent was removed. The product was dried overnight in the oven. Mass spectrum MH+=295.

Example 10

3-(3'-Hydroxymethyl-biphenyl-4-yloxymethyl)-benzoic acid 3-(3'-Hydroxymethyl-biphenyl-4-yloxymethyl)-benzoic acid was prepared using general procedure 1 from 3-(4-iodo-phenoxymethyl)-benzoic acid methyl ester (of Intermediate 1) and 3-(hydroxymethyl)phenylboronic acid (available from Aldrich Chemical Company, Inc., Milwaukee, Wis.). Mass spectrum MH+=335.

Example 11

3-(4-Isoquinolin-5-yl-phenoxymethyl)-benzoic acid

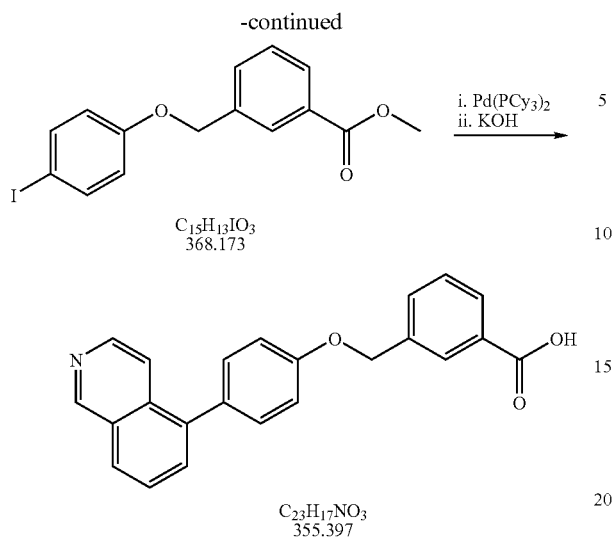

4.5 mL of a sonicated and degassed solution of 3-(4-iodo-phenoxymethyl)-benzoic acid methyl ester (of Intermediate 1; 740 mg, 2 mmol), potassium carbonate (830 mg, 6 mmol), bis(tri-cyclohexylphosphine)palladium (available from Strem Chemicals, Inc., Newburyport, Mass.; 70 mg, 0.1 mmol), dioxane (41 mL) and water (4.1 mL) was added to a reaction vial containing 5-isoquinolineboronic acid (available from Frontier Scientific, Inc., Logan, Utah; 104 mg, 0.6 mmol). The solution was sonicated and degassed. The mixture was heated in a microwave oven at 170 degrees for 25 min. The reaction mixture was filtered through silica, and washed with dioxane (1 mL) and dimethylacetamide (1 mL). 2 M potassium hydroxide solution (0.4 mL) was added. The mixture was stirred at room temperature overnight, and then 1 M HCl (0.8 mL) was added. The solvents were removed in the Genevac and then 50% aqueous methanol (2 mL) was added. The vial was centrifuged and the solvent removed. This process was repeated and then the same was dried overnight in the oven to give 3-(4-isoquinolin-5-yl-phenoxymethyl)-benzoic acid. Mass spectrum MH+=356.

Example 12

3-(2'-Methoxymethyl-biphenyl-4-yloxymethyl)-benzoic acid

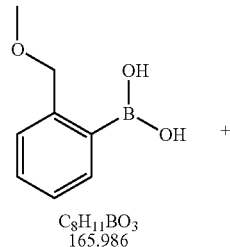

A solution of 3-(4-iodo-phenoxymethyl)-benzoic acid methyl ester (of intermediate 1; 37 mg, 0.1 mmol) in dioxane (2 mL) was degassed with nitrogen and then added to a reaction vial containing 2-methoxymethylphenylboronic acid (available from Apollo Scientific Ltd., Stockport, UK). The solution was sonicated and degassed and a solution of sodium hydroxide (4 M, 0.2 mL) was added, followed by bis(tri-cyclo-hexylphosphine)palladium (available from Strem Chemicals, Inc., Newburyport, Mass.; 0.005 mmol) was added. The mixture was degassed and then heated in a microwave oven at 170 degrees for 25 min. The reaction mixture was filtered through silica and the silica washed with dioxane (1 mL), and dimethylacetamide (1 mL). 1 M HCl was added until a solid formed. The vial was centrifuged and the solvent was removed. The crude product was washed with water and centrifuged again for 5 min. The water was decanted and the solid was dried in a vacuum oven at 50 degrees to give 3-(2'-methoxymethyl-biphenyl-4-yloxymethyl)-benzoic acid. Mass spectrum MH+=349.

Example 13

3-(3'-Methoxymethyl-biphenyl-4-yloxymethyl)-benzoic acid

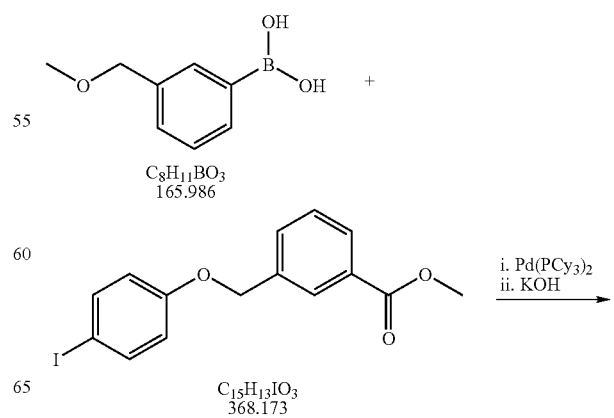

-continued

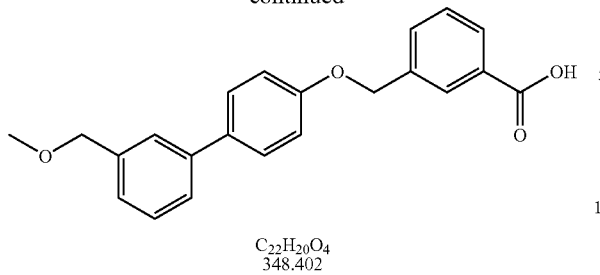

C₂₂H₂₀O₄
348.402

3-(3'-Methoxymethyl-biphenyl-4-yloxymethyl)-benzoic acid was prepared using the procedure described above for the preparation of Example 12 from 3-(4-iodo-phenoxymethyl)-benzoic acid methyl ester (of Intermediate 1) and 3-methoxymethylphenylboronic acid (available from Digital Specialty Chemicals, Inc., Dublin, N.H.). Mass spectrum MH+=349.

Example 14

3-(4-Naphthalen-1-yl-phenoxymethyl)-benzoic acid

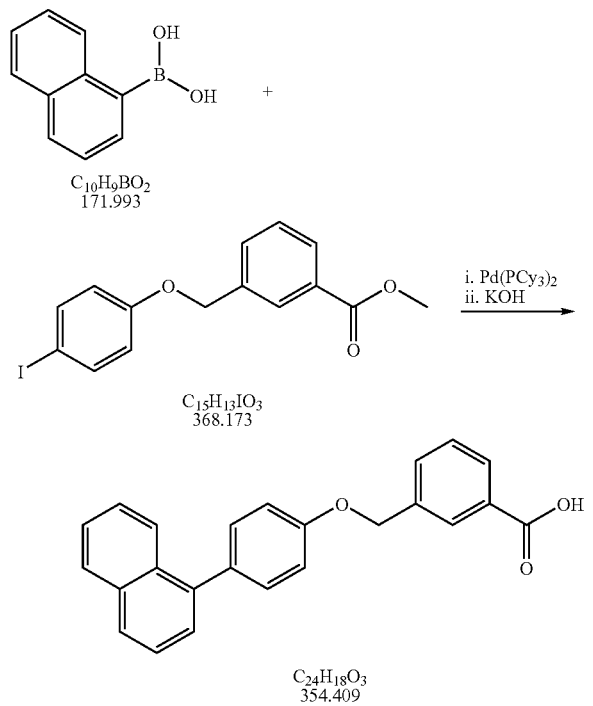

A solution of 3-(4-iodo-phenoxymethyl)-benzoic acid methyl ester (of intermediate 1; 74 mg, 0.2 mmol) in dioxane/water (10:1, 4.4 mL) was degassed for 20 min and then added to a reaction vial containing potassium carbonate (82 mg, 0.6 mmol) and 1-naphthaleneboronic acid (0.6 mmol; available from Aldrich Chemical Company, Inc., Milwaukee, Wis.). The solution was degassed for a further 2 min and then bis (tri-cyclohexylphosphine)palladium (available from Strem Chemicals, Inc., Newburyport, Mass.; 14 mg, 0.02 mmol) was added. The mixture was degassed for 30 seconds and then heated in a microwave oven at 170 degrees for 25 min. The reaction mixture was filtered through silica and the silica washed with dioxane (1 mL), dimethylacetamide (1 mL), and 20% methanol in dichloromethane (1 mL). The filtrate was placed in a vial and 2 M potassium hydroxide solution (0.4 mL) was added. The mixture was stirred at room temperature overnight, and then 1 M HCl was added until a solid formed (approxiamtely 2 mL). The vial was centrifuged and the solvent was removed. The product was dried overnight in the oven to give 3-(4-naphthalen-1-yl-phenoxymethyl)-benzoic acid. Mass spectrum MH+=355.

Example 15

3-(2'-Phenoxy-biphenyl-4-yloxymethyl)-benzoic acid

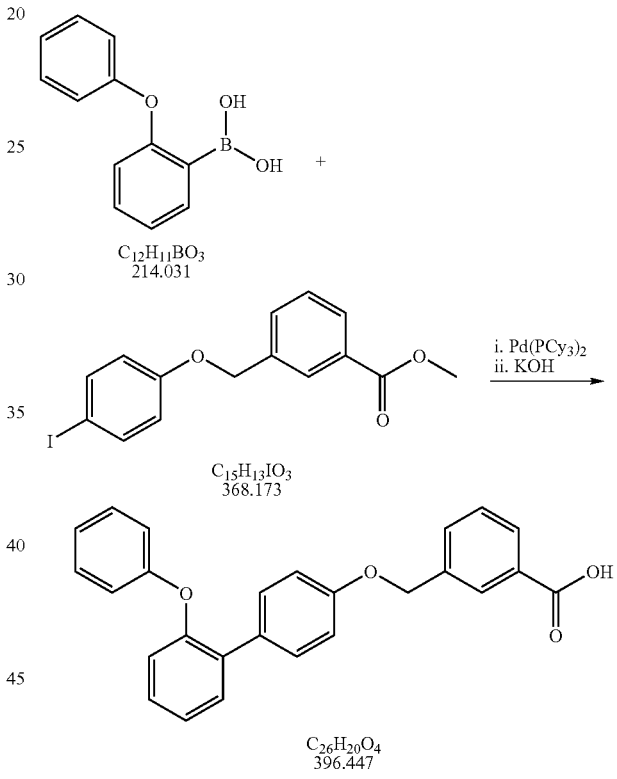

A degassed solution of 3-(4-iodo-phenoxymethyl)-benzoic acid methyl ester (of Inter-mediate 1; 74 mg, 0.2 mmol) in dioxane (4 mL) and a degassed solution of potassium carbonate (83 mg) in water (0.4 mL) were added to a reaction vial containing (2-phenoxy)phenylboronic acid (available from Aldrich Chemical Company, Inc., Milwaukee, Wis.; 128 mg, 0.6 mmol). The solution was degassed and bis(tri-cyclohexylphos-phine)palladium (available from Strem Chemicals, Inc., Newburyport, Mass.; 7 mg, 0.01 mmol) was added. The mixture was heated in a microwave oven at 170 degrees for 25 min. The reaction mixture was filtered through silica, and washed with dioxane (1 mL) and dimethylacetamide (1 mL). 2 M potassium hydroxide solution (0.4 mL) was added. The mixture was stirred at room temperature overnight, and then 1 M HCl (0.8 mL) was added. The solvent was evaporated and the residue was triurated with 50% aqueous methanol to give 3-(2'-phenoxy-biphenyl-4-yloxymethyl)-benzoic acid. Mass spectrum MH+=397.

Example 16

3-(3'-Pyrazol-1-yl-biphenyl-4-yloxymethyl)-benzoic acid

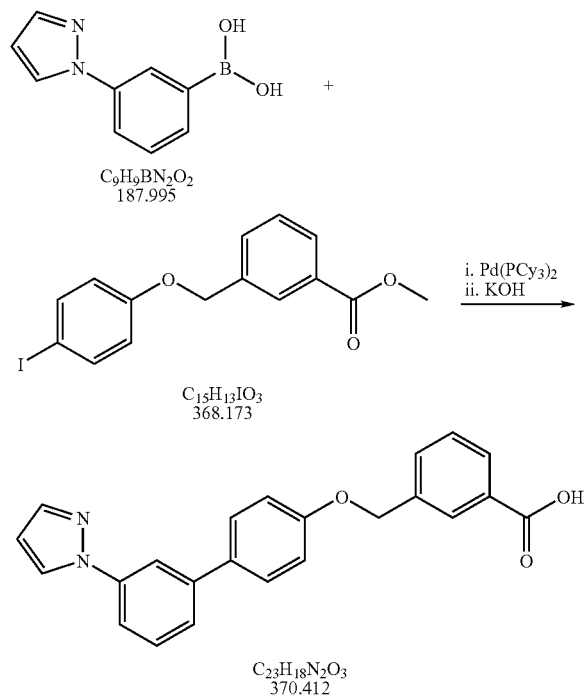

3-(3'-Pyrazol-1-yl-biphenyl-4-yloxymethyl)-benzoic acid was prepared using the procedure described above for the synthesis of Example 4 from 3-(4-iodo -phenoxymethyl)-benzoic acid methyl ester (of Intermediate 1) and 3-(1H-pyrazol-1-yl)phenylboronic acid (available from ASDI Inc., Newark, Del.). Mass spectrum MH+=371.

Example 17

3-(4-Pyridin-3-yl-phenoxymethyl)-benzoic acid

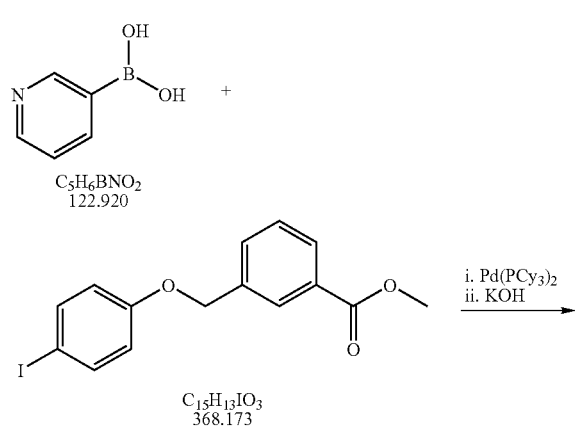

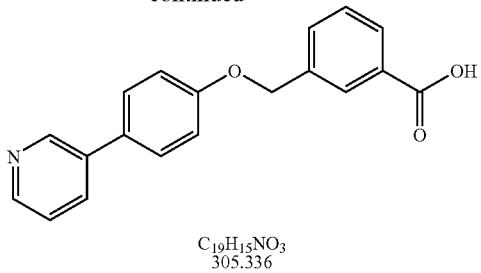

3-(4-Pyridin-3-yl-phenoxymethyl)-benzoic acid was prepared using the procedure described above for the synthesis of Example 3 from 3-(4-iodo -phenoxymethyl)-benzoic acid methyl ester (of Intermediate 1) and pyridine-3-boronic acid (available from Aldrich Chemical Company, Inc., Milwaukee, Wis.). Mass spectrum MH+=306.

Example 18

3-(4-Thiophen-3-yl-phenoxymethyl)-benzoic acid

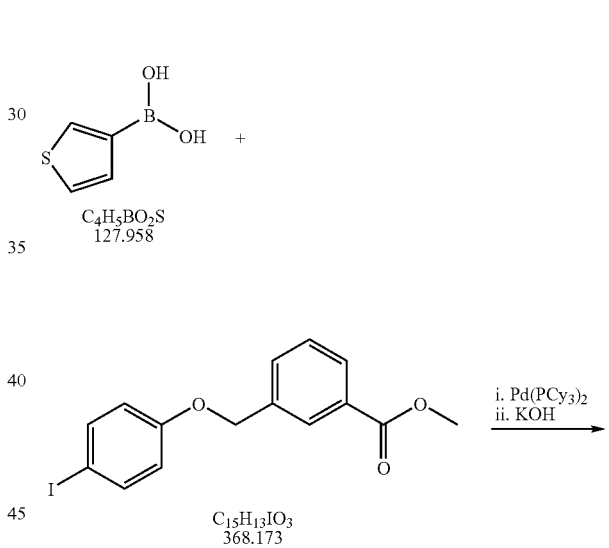

3-(4-Thiophen-3-yl-phenoxymethyl)-benzoic acid was prepared using the procedure described above for the preparation of Example 15 from 3-(4-iodo -phenoxymethyl)-benzoic acid methyl ester (of Intermediate 1) and thiophene-3-boronic acid (available from Aldrich Chemical Company, Inc., Milwaukee, Wis.). Mass spectrum MH+=311.

Example 19

3-(2'-Trifluoromethoxy-biphenyl-4-yloxymethyl)-benzoic acid

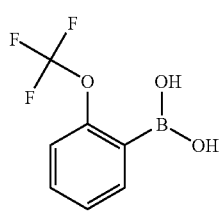

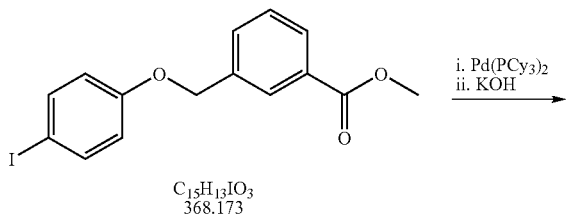

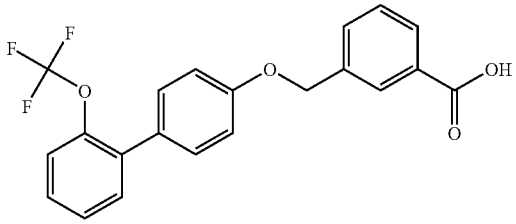

3-(2'-Trifluoromethoxy-biphenyl-4-yloxymethyl)-benzoic acid was prepared using general procedure 1 from 3-(4-iodo-phenoxymethyl)-benzoic acid methyl ester (of Intermediate 1) and 2-(trifluoromethoxy)benzeneboronic acid (ASDI Incorporated, Newark, Del.). Mass spectrum MH+=389.

Example 20

3-(4'-Trifluoromethoxy-biphenyl-4-yloxymethyl)-benzoic acid

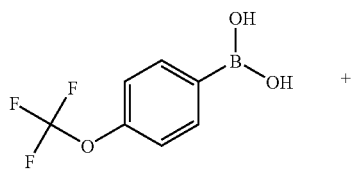

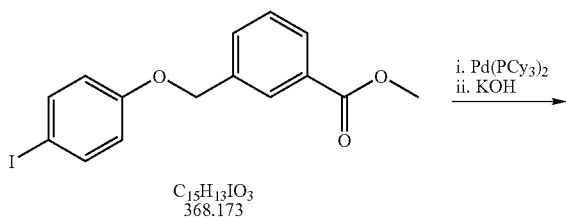

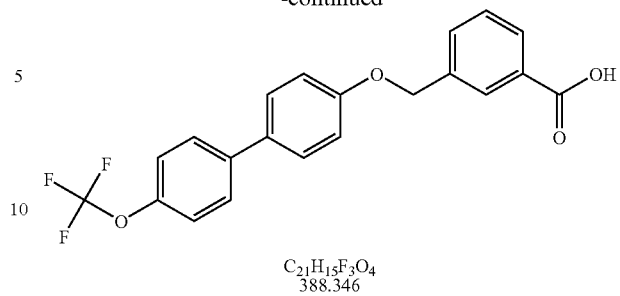

3-(4'-Trifluoromethoxy-biphenyl-4-yloxymethyl)-benzoic acid was prepared using general procedure 1 from 3-(4-iodo-phenoxymethyl)-benzoic acid methyl ester (of Intermediate 1) and 4-(trifluoromethoxy)benzeneboronic acid (ASDI Incorporated, Newark, Del.). Mass spectrum MH+=389.

Example 21

2-(3'-Acetylamino-biphenyl-4-yloxymethyl)-thiazole-4-carboxylic acid

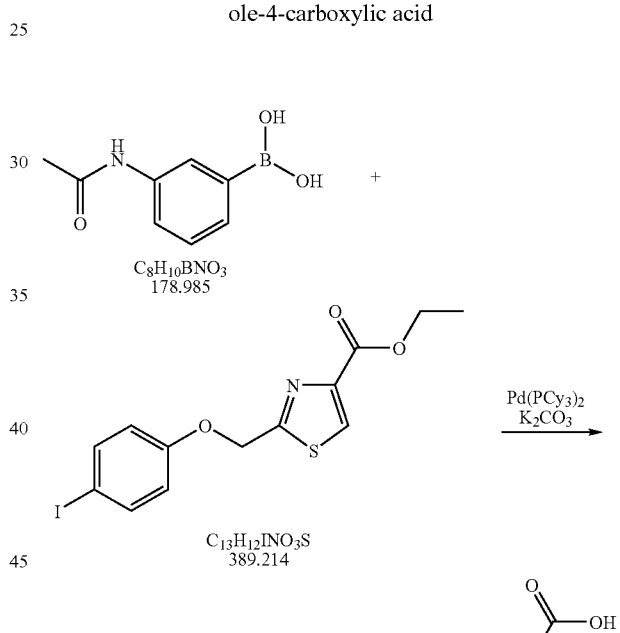

A first stock solution was prepared consisting of 2-(4-iodo-phenoxymethyl)-thiazole-4-carboxylic acid ethyl ester (of intermediate 2; 1.56 g, 4 mmol), bis(tri-cyclohexyl-phosphine)palladium (available from Strem Chemicals, Inc., Newburyport, Mass.; 140 mg, 0.21 mmol), and dioxane (approximately 82 mL). A second stock solution was prepared consisting of potassium carbonate (1.66 g, 12 mmol) and water (approximately 8.2 mL). The solutions were sonicated and degassed by bubbling nitrogen gas through them. 4 mL of the first stock solution and 0.4 mL of the second stock solution were added to a reaction vial containing 3-acetamidobenzeneboronic acid (ASDI Incorporated, Newark, Del.; 107 mg, 0.6 mmol). The mixture was heated in a microwave oven at 170 degrees for 25 min. 1 M HCl (0.1 mL) was added to each vial, and the solution were passed through silica gel columns (1 g of silica), and washed with dimethylacetamide (2×1 mL). The solution was evaporated to dryness to give 2-(3'-acetylamino-biphenyl-4-yloxymethyl) -thiazole-4-carboxylic acid. Mass spectrum MH+=369.

Example 22

2-(4-Benzo[1,3]dioxol-5-yl-phenoxymethyl)-thiazole-4-carboxylic acid

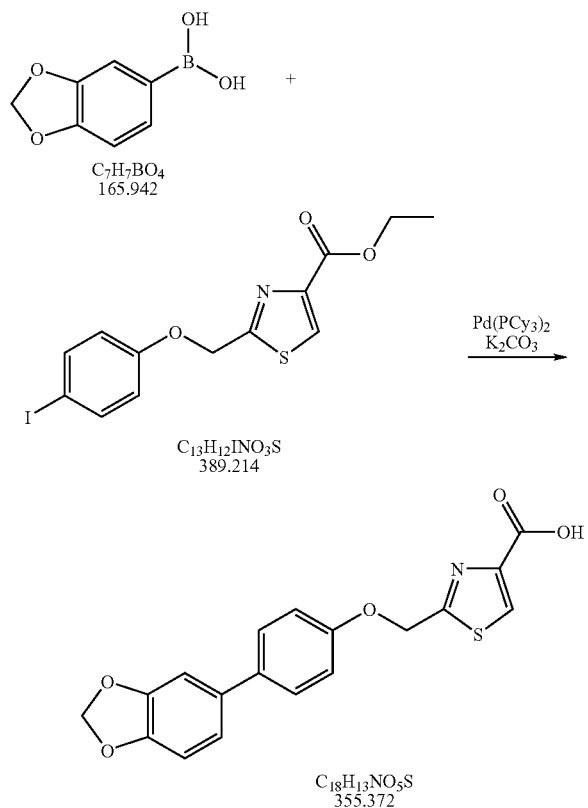

A solution of 2-(4-iodo-phenoxymethyl)-thiazole-4-carboxylic acid ethyl ester (of intermediate 2; 75 mg, 0.2 mmol) in dioxane (4 mL) was added to a reaction tube containing 3,4-methylenedioxybenzeneboronic acid (ASDI Incorporated, Newark, Del.; 100 mg, 0.6 mmol). A solution of potassium carbonate (80 mg, 0.6 mmol) in water (0.4 mL) was added and the mixture was degassed. A solution of bis(tricyclohexylphosphine)-palladium (available from Strem Chemicals, Inc., Newburyport, Mass.; 7 mg, 0.01 mmol) in dioxane (0.5 mL) was added and the tube was heated in a microwave oven at 170 degrees for 25 min. The solution was acidified, filtered through silica gel, evaporated, and triturated with aqueous methanol to give 2-(4-benzo[1,3]dioxol-5-yl-phenoxymethyl)-thiazole-4-carboxylic acid. Mass spectrum MH+=356.

Example 23

2-(2'-Benzyloxy-biphenyl-4-yloxymethyl)-thiazole-4-carboxylic acid

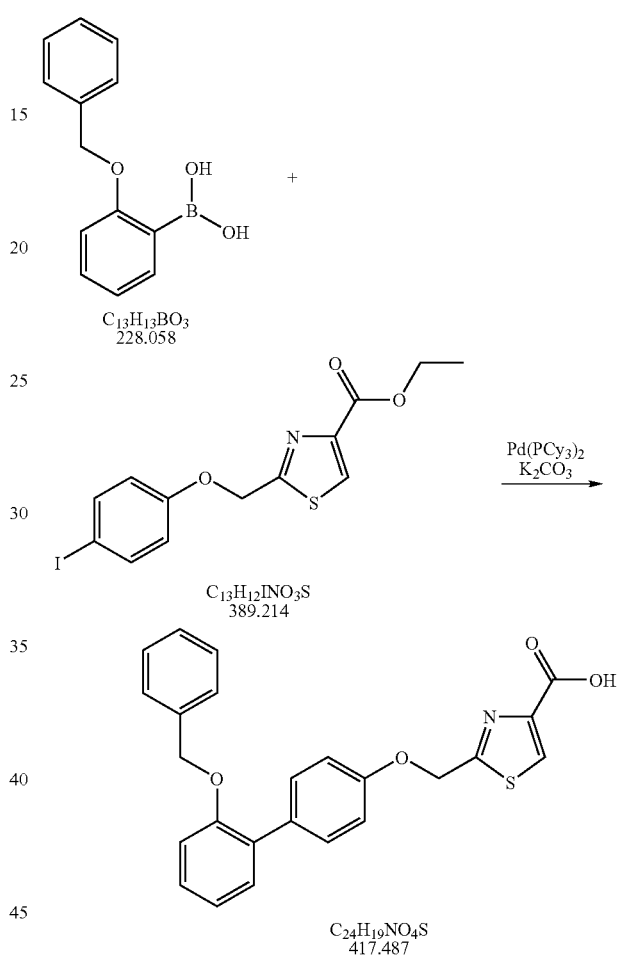

A first stock solution was prepared consisting of 2-(4-iodophenoxymethyl) -thiazole-4-carboxylic acid ethyl ester (of Intermediate 2; 1.72 g, 4.4 mmol), bis(tri -cyclohexyl-phosphine)palladium (available from Strem Chemicals, Inc., Newburyport, Mass.; 154 mg, 0.23 mmol), and dioxane (approximately 90 mL). A second stock solution was prepared consisting of potassium carbonate (1.826 g, 13.2 mmol) and water (approximately 9 mL). The solutions were sonicated and degassed by bubbling nitrogen gas through them. 4 mL of the first stock solution and 0.4 mL of the second stock solution were added to a reaction vial containing (Z-benzyloxyphenyl)boronic acid (available from Aldrich Chemical Company, Inc., Milwaukee, Wis.; 260 mg, 0.4 mmol). The mixture was heated in a microwave oven at 170 degrees for 25 min and then passed through a silica gel column (1 g of silica), and washed with dimethylacetamide (2×1 mL). The solvents were removed in the Genevac to give 2-(2'-benzyloxy-biphenyl-4-yloxymethyl)-thiazole-4-carboxylic acid. Mass spectrum MH+=418.

Example 24

2-[4-(1-Benzyl-1H-pyrazol-4-yl)-phenoxymethyl]-thiazole-4-carboxylic acid

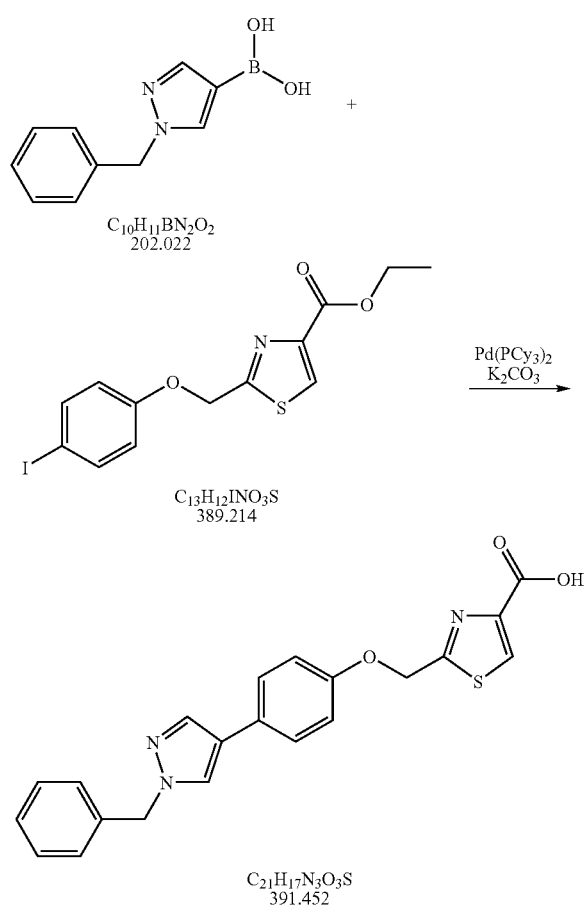

2-[4-(1-Benzyl-1H-pyrazol-4-yl)-phenoxymethyl]-thiazole-4-carboxylic acid was prepared using general procedure 2 from 2-(4-iodo-phenoxymethyl)-thiazole-4-carboxylic acid ethyl ester (of Intermediate 2) and 1-benzyl-1h-pyrazole-4-boronic acid (available from Frontier Scientific, Inc., Logan, Utah). Mass spectrum MH+=392.

Example 25

2-([1,1':3',1"]Terphenyl-4-yloxymethyl)-thiazole-4-carboxylic acid

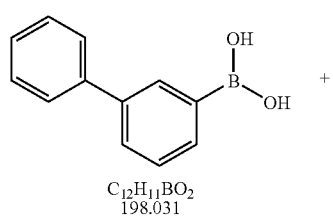

A solution of 2-(4-iodo-phenoxymethyl)-thiazole-4-carboxylic acid ethyl ester (of intermediate 2; 71 mg, 0.2 mmol) in dioxane (3.5 mL) was added to a reaction tube containing biphenyl-3-boronic acid (available from Lancaster Synthesis Ltd., Morecambe, UK; 119 mg, 0.6 mmol). A solution of potassium carbonate (74 mg, 0.5 mmol) in water (0.4 mL) was added and the mixture was degassed. A solution of bis(tricyclohexylphosphine)-palladium (available from Strem Chemicals, Inc., Newburyport, Mass.; 7 mg, 0.01 mmol) in dioxane (0.5 mL) was added and the tube was heated in a microwave oven at 170 degrees for 25 min. Concentrated hydrochloric acid (0.1 mL) was added and the mixture was passed through a silica gel column (1 g of silica), and washed with dimethylacetamide (2×1 mL). The filtrate was evaporated to dryness and the resulting gum was triturated twice with 50% aqueous methanol to give 2-([1,1';3',1"]terphenyl-4-yloxymethyl)-thiazole-4-carboxylic acid. Mass spectrum MH+=388

Example 26

2-(3'-Carbamoyl-biphenyl-4-yloxymethyl)-thiazole-4-carboxylic acid

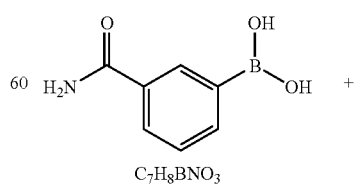

-continued

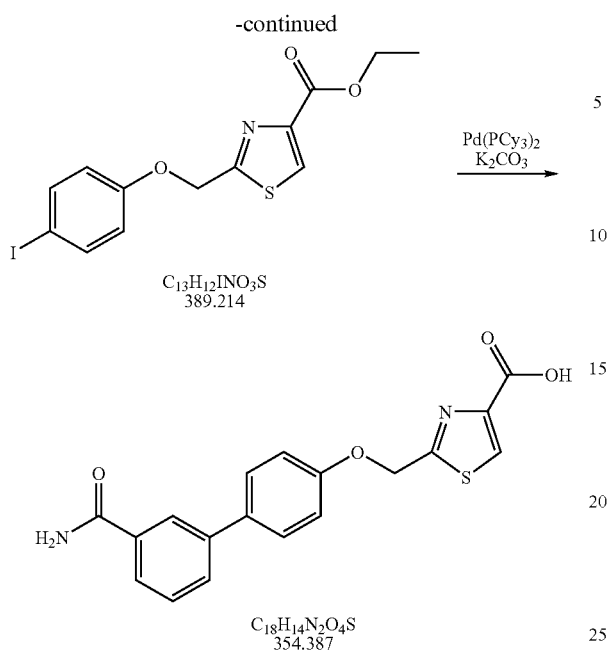

2-(3'-Carbamoyl-biphenyl-4-yloxymethyl)-thiazole-4-carboxylic acid was prepared using general procedure 2 from 2-(4-iodo-phenoxymethyl)-thiazole-4-carboxylic acid ethyl ester (of Intermediate 2) and (3-aminocarbonylphenyl)boronic acid (available from Apollo Scientific Ltd., Stockport, UK). Mass spectrum MH+=355.

Example 27

2-[4-(2-Chloro-pyridin-3-yl)-phenoxymethyl]-thiazole-4-carboxylic acid

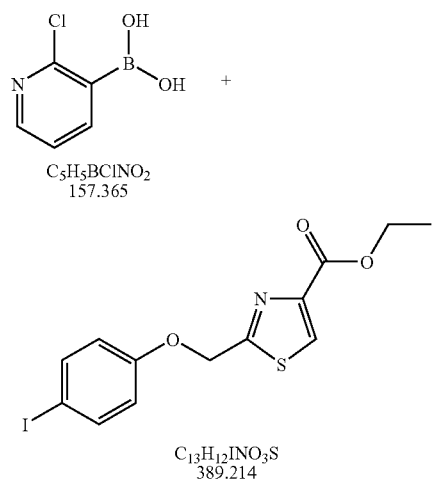

-continued

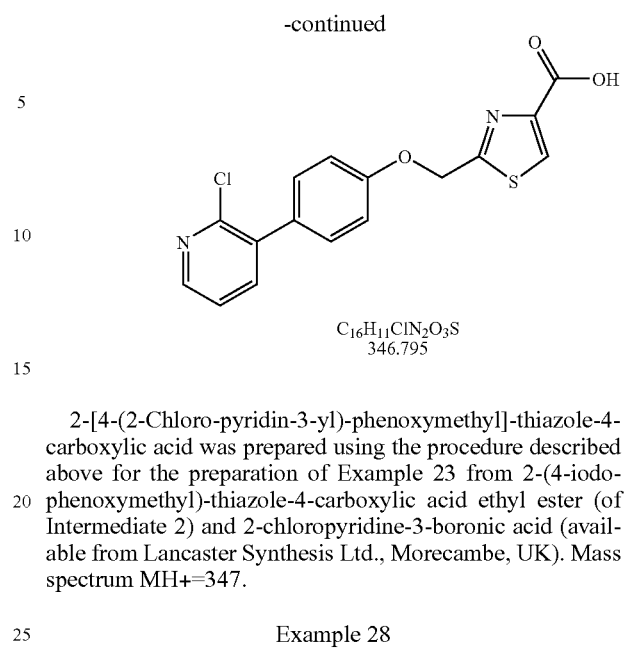

2-[4-(2-Chloro-pyridin-3-yl)-phenoxymethyl]-thiazole-4-carboxylic acid was prepared using the procedure described above for the preparation of Example 23 from 2-(4-iodo-phenoxymethyl)-thiazole-4-carboxylic acid ethyl ester (of Intermediate 2) and 2-chloropyridine-3-boronic acid (available from Lancaster Synthesis Ltd., Morecambe, UK). Mass spectrum MH+=347.

Example 28

2-[4-(6-Fluoro-pyridin-3-yl)-phenoxymethyl]-thiazole-4-carboxylic acid

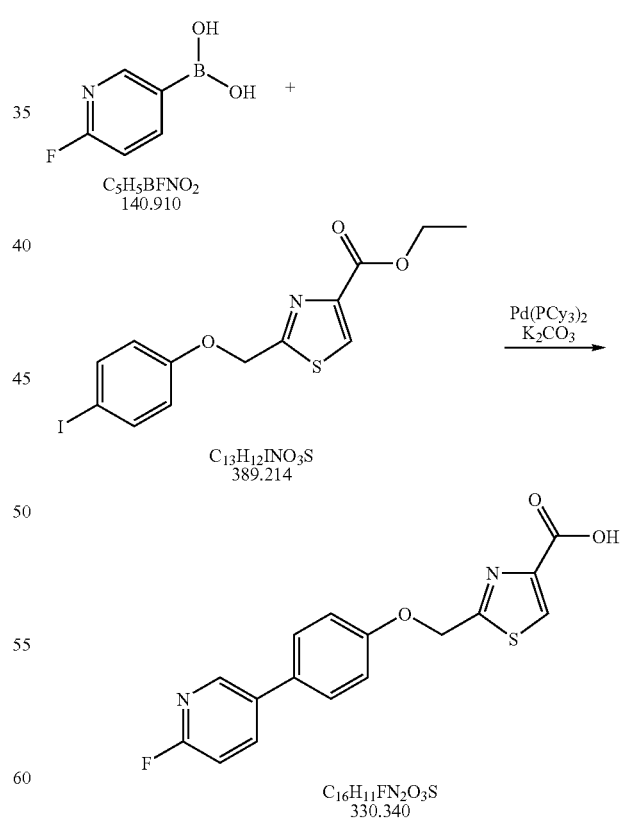

2-[4-(6-Fluoro-pyridin-3-yl)-phenoxymethyl]-thiazole-4-carboxylic acid was prepared using the procedure described above for the preparation of Example 23 from 2-(4-iodo-phenoxymethyl)-thiazole-4-carboxylic acid ethyl ester (of Intermediate 2) and 2-fluoropyridine-5-boronic acid (available from Frontier Scientific, Inc., Logan, Utah). Mass spectrum MH+=331.

Example 29

2-(3'-Hydroxymethyl-biphenyl-4-yloxymethyl)-thiazole-4-carboxylic acid

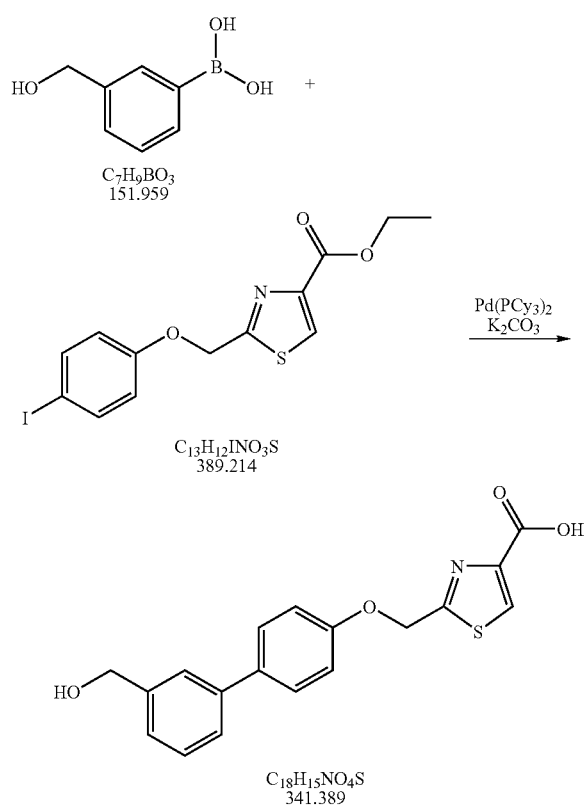

2-(3'-Hydroxymethyl-biphenyl-4-yloxymethyl)-thiazole-4-carboxylic acid was prepared using the procedure described above for the preparation of Example 22 from 2-(4-iodo-phenoxymethyl)-thiazole-4-carboxylic acid ethyl ester (of Intermediate 2) and 3-(hydroxymethyl)phenylboronic acid (available from Aldrich Chemical Company, Inc., Milwaukee, Wis.). Mass spectrum MH+=342.

Example 30

2-(4-Isoquinolin-5-yl-phenoxymethyl)-thiazole-4-carboxylic acid

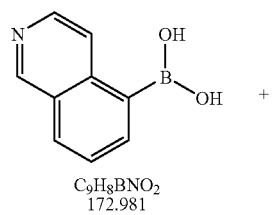

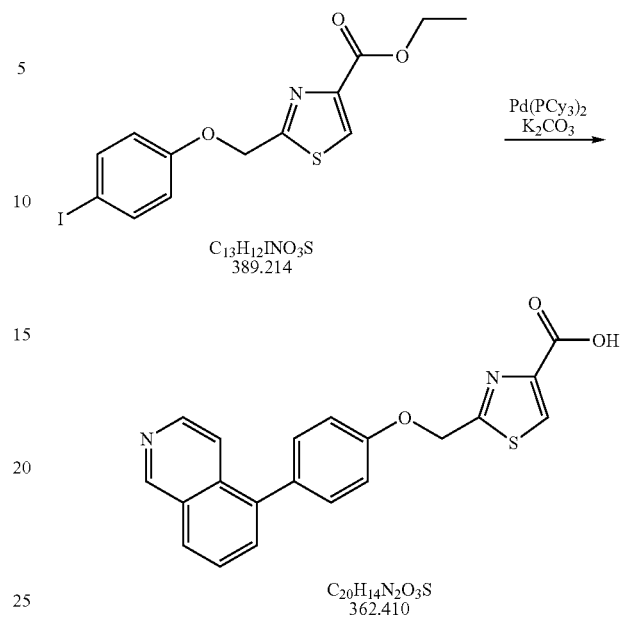

2-(4-Isoquinolin-5-yl-phenoxymethyl)-thiazole-4-carboxylic acid was prepared using general procedure 2 from 2-(4-iodo-phenoxymethyl)-thiazole-4-carboxylic acid ethyl ester (of Intermediate 2) and 5-isoquinolineboronic acid (available from Frontier Scientific, Inc., Logan, Utah). Mass spectrum MH+=363.

Example 31

2-(2'-Methoxymethyl-biphenyl-4-yloxymethyl)-thiazole-4-carboxylic acid

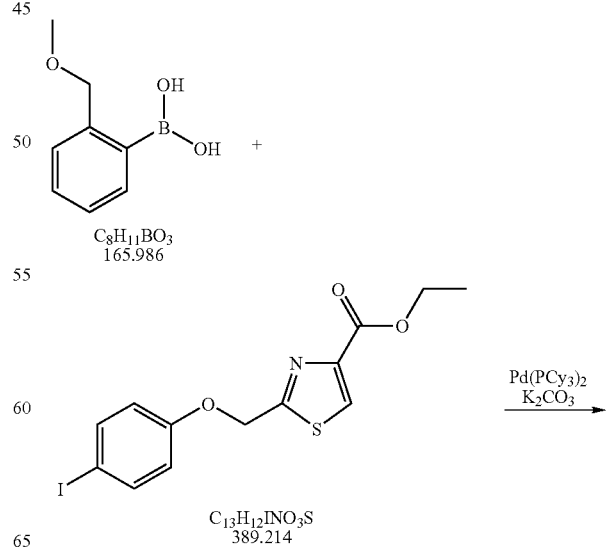

-continued

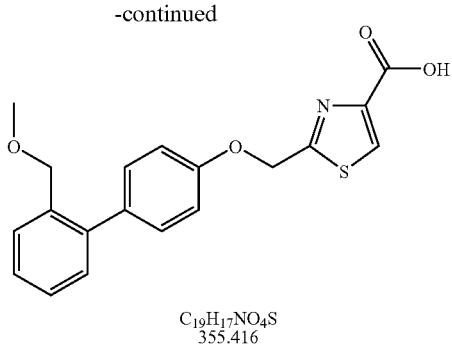

2-(2'-Methoxymethyl-biphenyl-4-yloxymethyl)-thiazole-4-carboxylic acid was prepared using general procedure 2 from 2-(4-iodo-phenoxymethyl)-thiazole-4-carboxylic acid ethyl ester (of Intermediate 2) and 2-methoxymethylphenylboronic acid (available from Apollo Scientific Ltd., Stockport, UK). Mass spectrum MH+=356.

Example 32

2-(3'-Methoxymethyl-biphenyl-4-yloxymethyl)-thiazole-4-carboxylic acid

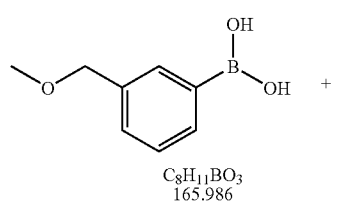

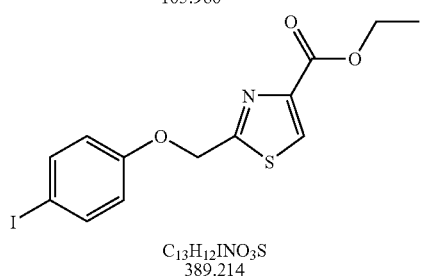

2-(3'-Methoxymethyl-biphenyl-4-yloxymethyl)-thiazole-4-carboxylic acid was prepared using general procedure 2 from 2-(4-iodo-phenoxymethyl)-thiazole-4-carboxylic acid ethyl ester (of Intermediate 2) and 3-methoxymethylphenylboronic acid (available from Digital Specialty Chemicals, Inc., Dublin, N.H.). Mass spectrum MH+=356.

Example 33

2-(4-Naphthalen-1-yl-phenoxymethyl)-thiazole-4-carboxylic acid

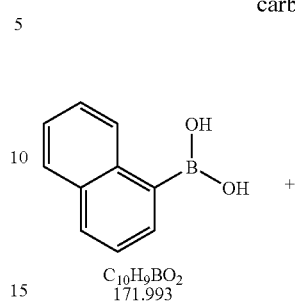

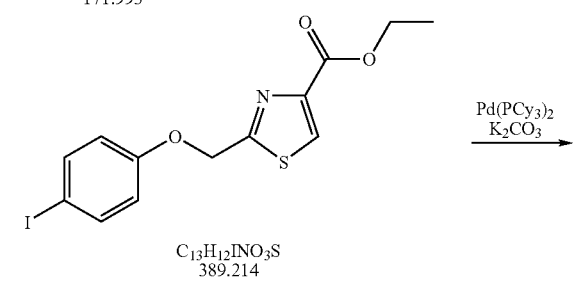

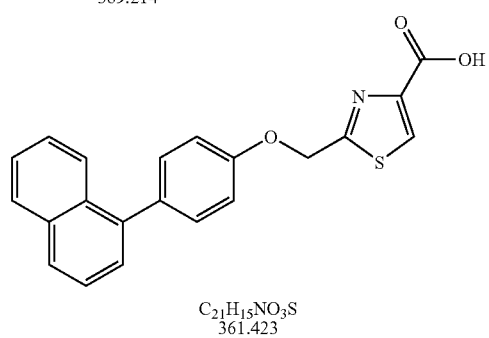

2-(4-Naphthalen-1-yl-phenoxymethyl)-thiazole-4-carboxylic acid was prepared using the procedure described above for the preparation of Example 22 from 2-(4-iodo-phenoxymethyl)-thiazole-4-carboxylic acid ethyl ester (of Intermediate 2) and 1-naphthaleneboronic acid (available from Aldrich Chemical Company, Inc., Milwaukee, Wis.). Mass spectrum MH+=362.

Example 34

2-(2'-Phenoxy-biphenyl-4-yloxymethyl)-thiazole-4-carboxylic acid

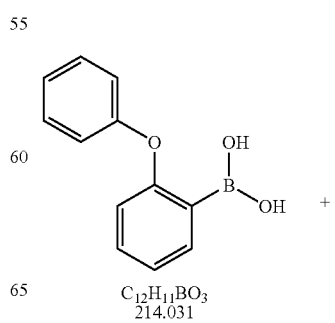

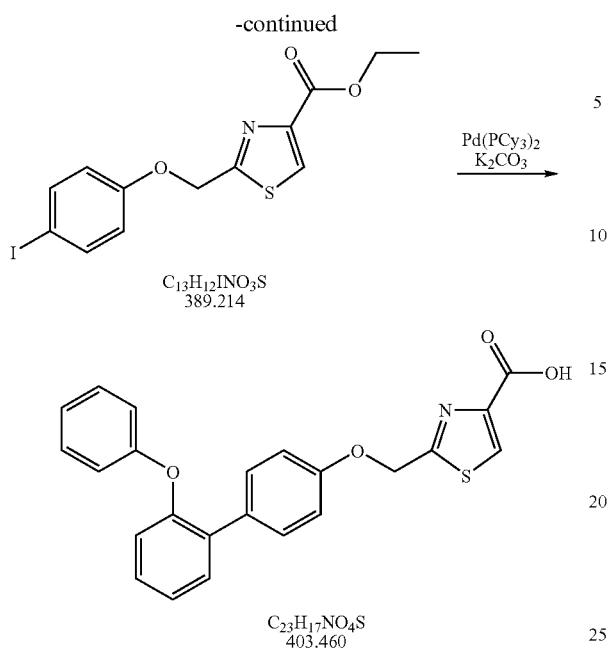

2-(2'-Phenoxy-biphenyl-4-yloxymethyl)-thiazole-4-carboxylic acid was prepared using the procedure described above for the preparation of Example 25 from 2-(4-iodo-phenoxymethyl)-thiazole-4-carboxylic acid ethyl ester (of Intermediate 2) and (2-phenoxy)phenylboronic acid (available from Aldrich Chemical Company, Inc., Milwaukee, Wis.). Mass spectrum MH+=404.

Example 35

2-(4-Thiophen-3-yl-phenoxymethyl)-thiazole-4-carboxylic acid

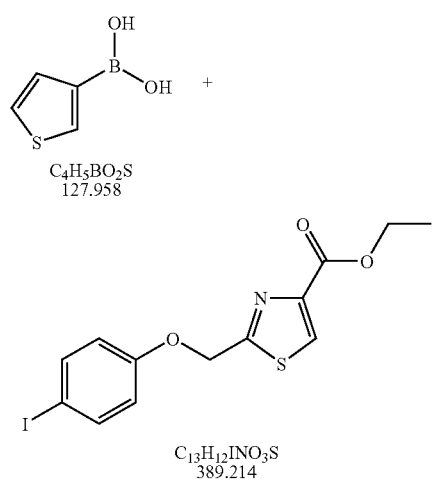

A solution of 2-(4-iodo-phenoxymethyl)-thiazole-4-carboxylic acid ethyl ester (of Intermediate 2; 78 mg, 0.2 mmol) in dioxane (2 mL) was degassed with nitrogen and then added to a reaction vial containing thiophene-3-boronic acid (available from Aldrich Chemical Company, Inc., Milwaukee, Wis.). The solution was sonicated and degassed and a solution of potassium carbonate (1.5 M, 0.4 mL) was added, followed by bis(tri-cyclo-hexylphosphine)palladium (available from Strem Chemicals, Inc., Newburyport, Mass.; 7 mg, 0.01 mmol) was added. The mixture was degassed and then heated in a microwave oven at 170 degrees for 25 min. The reaction mixture was evaporated in the Genevac to give 2-(4-thiophen-3-yl-phenoxymethyl)-thiazole-4-carboxylic acid. Mass spectrum MH+=318.

Example 36

2-(2'-Trifluoromethoxy-biphenyl-4-yloxymethyl)-thiazole-4-carboxylic acid

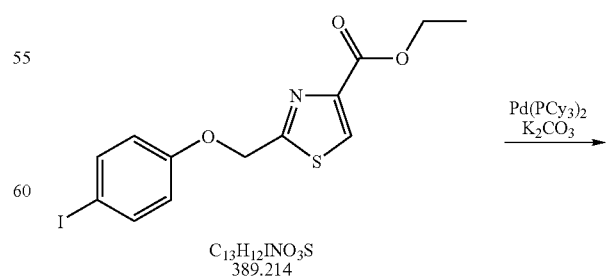

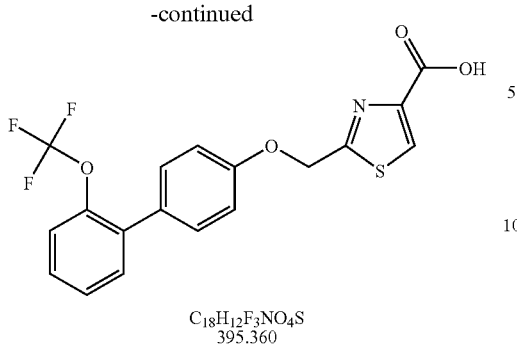

$C_{18}H_{12}F_3NO_4S$
395.360

2-(2'-Trifluoromethoxy-biphenyl-4-yloxymethyl)-thiazole-4-carboxylic acid was pre-pared using the procedure described above for the preparation of Example 21 from 2-(4-iodo-phenoxymethyl)-thiazole-4-carboxylic acid ethyl ester (of Intermediate 2) and 2-(trifluoromethoxy)benzeneboronic acid (available from Apin Chemicals Ltd., Abingdon, UK). Mass spectrum MH+=396.

Example 37

6-(4-Benzor[1,3]dioxol-5-yl-phenoxymethyl)-pyridine-2-carboxylic acid

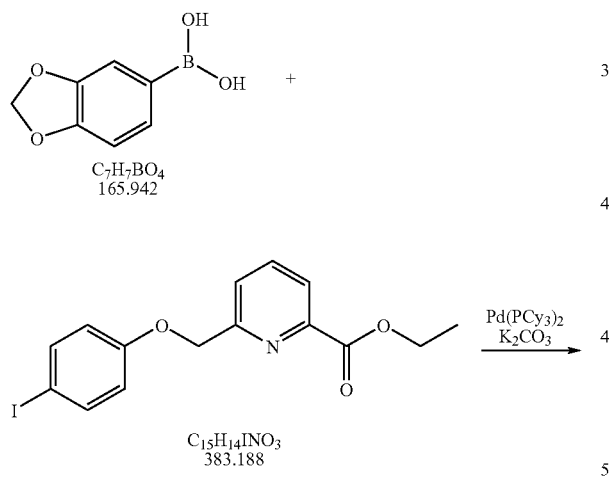

$C_7H_7BO_4$
165.942

$C_{15}H_{14}INO_3$
383.188

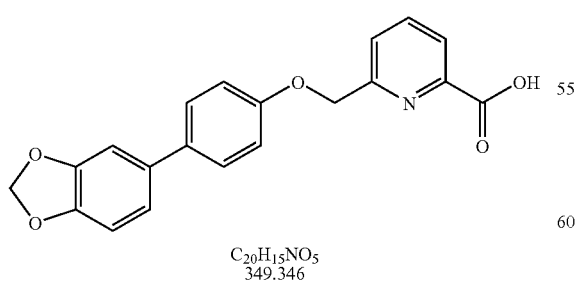

$C_{20}H_{15}NO_5$
349.346

6-(4-Benzo[1,3]dioxol-5-yl-phenoxymethyl)-pyridine-2-carboxylic acid was prepared using general procedure 3 from 6-(4-iodo-phenoxymethyl)-pyridine-2-carboxylic acid ethyl ester (of Intermediate 3) and 3,4-methylenedioxybenzeneboronic acid (ASDI Incorporated, Newark, Del.). Mass spectrum MH+=350.

Example 38

6-(2'-Methoxymethyl-biphenyl-4-yloxymethyl)-pyridine-2-carboxylic acid

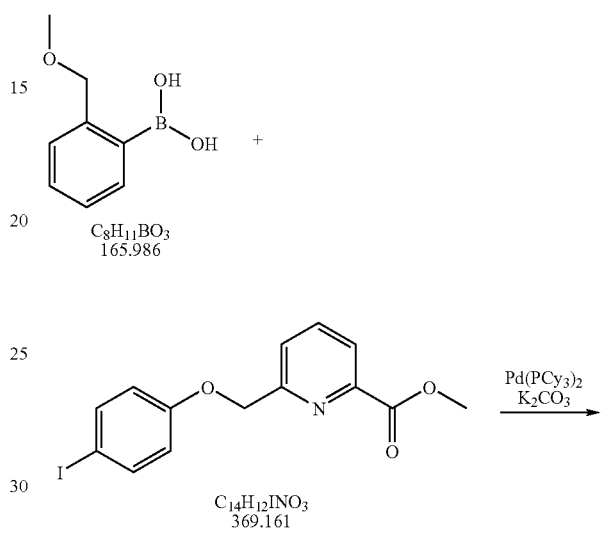

$C_8H_{11}BO_3$
165.986

$C_{14}H_{12}INO_3$
369.161

$C_{21}H_{19}NO_4$
349.390

A first stock solution was prepared consisting of 6-(4-iodo-phenoxymethyl)-pyridine-2-carboxylic acid methyl ester (of intermediate 5; 1.77 g, 4.8 mmol), bis(tri-cyclohexyl-phosphine)palladium (available from Strem Chemicals, Inc., Newburyport, Mass.; 168 mg, 0.25 mmol), and dioxane (approximately 100 mL). A second stock solution was prepared consisting of potassium carbonate (1.99 g, 14.4 mmol) and water (approximately 10 mL). The solutions were sonicated and degassed by bubbling nitrogen gas through them. 4 mL of the first stock solution and 0.4 mL of the second stock solution were added to a reaction tube containing 2-methoxymethyl-phenylboronic acid (available from Apollo Scientific Ltd., Stockport, UK; 100 mg, 0.6 mmol). The mixture was heated in a microwave oven at 170 degrees for 25 min, and then 1 M KOH solution (1 equivalent) was added and the reaction mixture was heated in the microwave for 10 minutes at 120 degrees, for 10 minutes at 130 degrees, and at 170 degrees for one hour. The reaction mixture was then filtered through a silica column (1 g) and washed with dimethylacetamide (2×1 mL). The solvent was evaporated to give 6-(2'- methoxymethyl-biphenyl-4-yloxymethyl)-pyridine-2-carboxylic acid. Mass spectrum MH+=350.

Example 39

6-(4-Thiophen-2-yl-phenoxymethyl)-pyridine-2-carboxylic acid

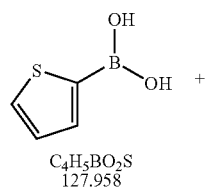

C₄H₅BO₂S
127.958

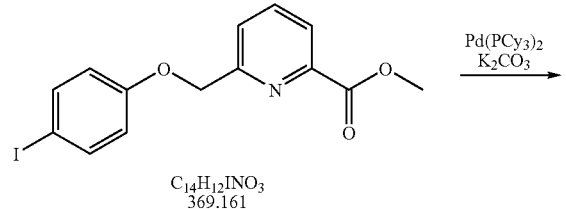

C₁₄H₁₂INO₃
369.161

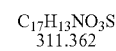

C₁₇H₁₃NO₃S
311.362

6-(4-Thiophen-2-yl-phenoxymethyl)-pyridine-2-carboxylic acid was prepared using the procedure described above for the preparation of Example 38 from 6-(4-iodophenoxymethyl)-pyridine-2-carboxylic acid methyl ester (of Intermediate 5) and 2-methoxymethylphenylboronic acid (available from Aldrich Chemical Company, Inc., Milwaukee, Wis.). Mass spectrum MH+=312.

Example 40

[3-(3'-Acetylamino-biphenyl-4-yloxymethyl)-phenyl]-acetic acid

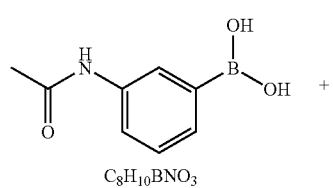

C₈H₁₀BNO₃
178.985

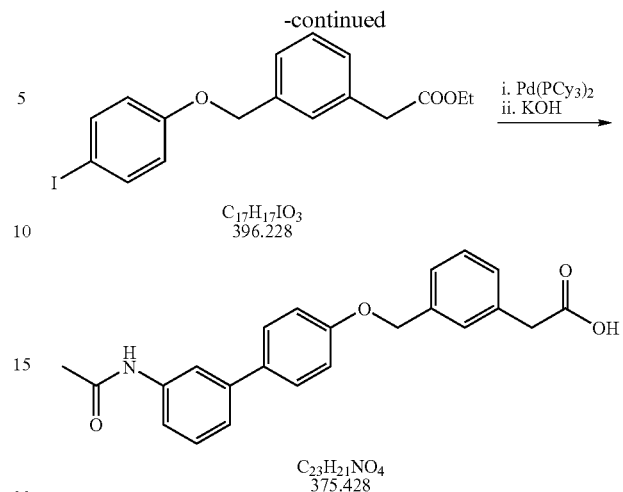

C₁₇H₁₇IO₃
396.228

C₂₃H₂₁NO₄
375.428

[3-(3'-Acetylamino-biphenyl-4-yloxymethyl)-phenyl]-acetic acid was prepared using general procedure 5 from [3-(4-iodo-phenoxymethyl)-phenyl]-acetic acid ethyl ester (of intermediate 4) and 3-acetamidobenzeneboronic acid (ASDI Incorporated, Newark, Del.). Mass spectrum MH+=376.

Example 41

[3-(3'-Hydroxymethyl-biphenyl-4-yloxymethyl)-phenyl]-acetic acid

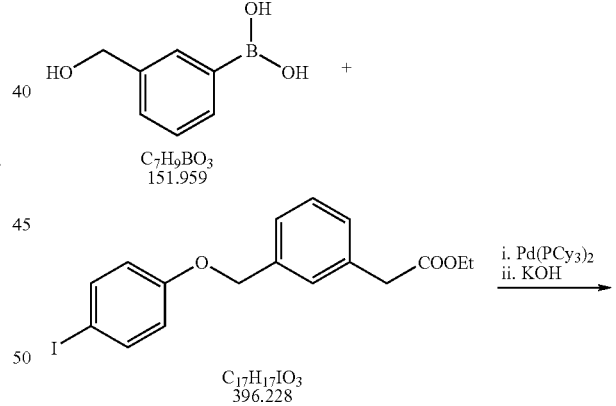

C₇H₉BO₃
151.959

C₁₇H₁₇IO₃
396.228

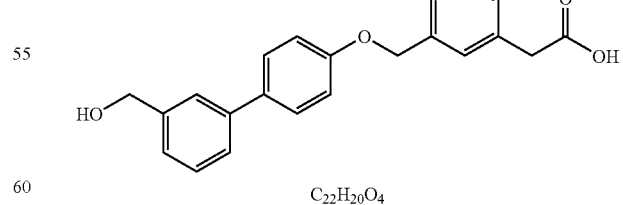

C₂₂H₂₀O₄
348.402

[3-(3'-Hydroxymethyl-biphenyl-4-yloxymethyl)-phenyl]-acetic acid was prepared using general procedure 5 from [3-(4-iodo-phenoxymethyl)-phenyl]-acetic acid ethyl ester (of intermediate 4) and 3-(hydroxymethyl)phenylboronic acid (available from Aldrich Chemical Company, Inc., Milwaukee, Wis.). Mass spectrum MH+=349.

Example 42

[3-(2'-Methoxymethyl-biphenyl-4-yloxymethyl)-phenyl]-acetic acid

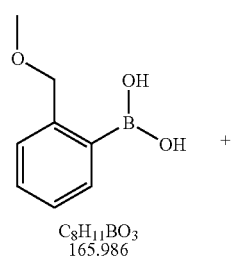

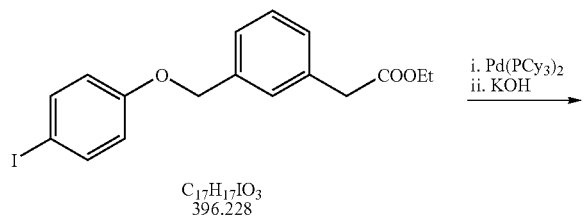

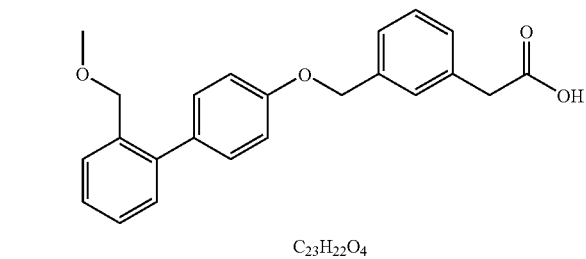

[3-(2'-Methoxymethyl-biphenyl-4-yloxymethyl)-phenyl]-acetic acid was prepared using general procedure 4 from [3-(4-iodo-phenoxymethyl)-phenyl]-acetic acid ethyl ester (of intermediate 4) and 2-methoxymethylphenylboronic acid (available from Apollo Scientific Ltd., Stockport, UK). Mass spectrum MH+=363.

Example 43

{3-[4-(2-Methoxy-pyridin-3-yl)-phenoxymethyl]-phenyl}-acetic acid

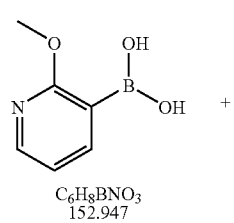

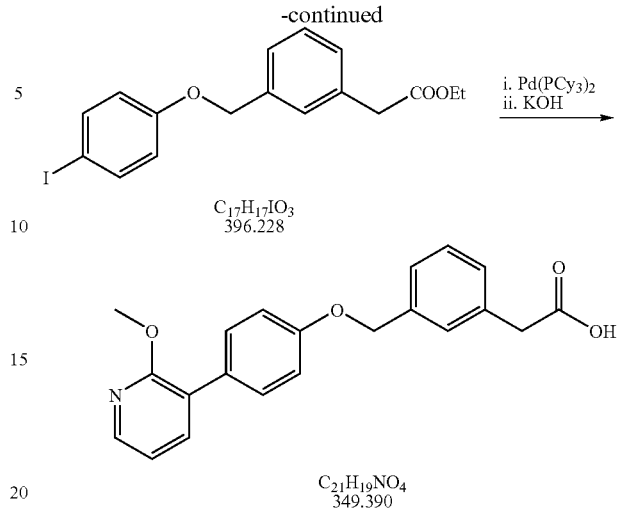

{3-[4-(2-Methoxy-pyridin-3-yl)-phenoxymethyl]-phenyl}-acetic acid was prepared using general procedure 4 from [3-(4-iodo-phenoxymethyl)-phenyl]-acetic acid ethyl ester (of intermediate 4) and 2-methoxy-pyridine-3-boronic acid (available from Lan-caster Synthesis Ltd., Lancashire, UK). Mass spectrum MH+=350.

Example 44

[3-(2'-Trifluoromethoxy-biphenyl-4-yloxymethyl)-phenyl]-acetic acid

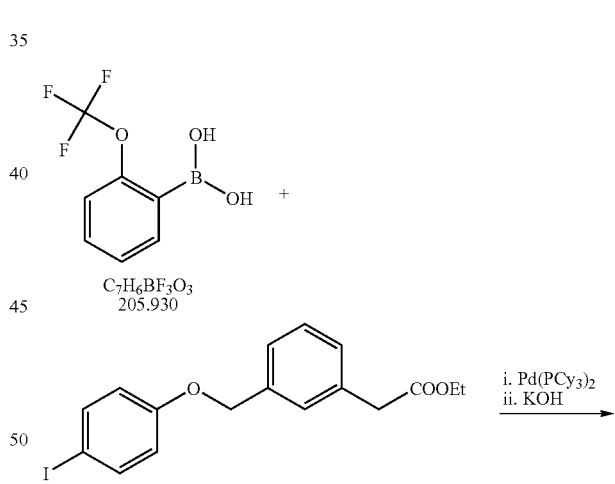

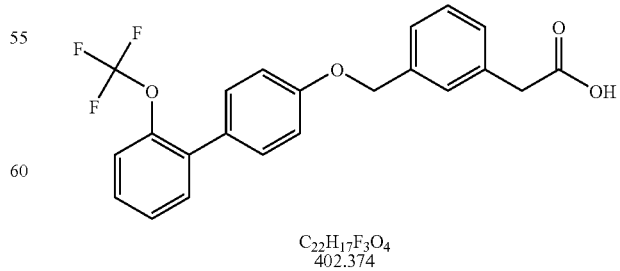

[3-(2'-Trifluoromethoxy-biphenyl-4-yloxymethyl)-phenyl]-acetic acid was pre-pared using general procedure 5 from [3-(4-iodo-phenoxymethyl)-phenyl]-acetic acid ethyl ester (of intermediate 4) and 2-(trifluoromethoxy)benzeneboronic acid (ASDI Incorporated, Newark, Del.). Mass spectrum MH+=403.

Glycogen Synthase (GS) Assay

The following tests were carried out in order to determine the activity of the compounds of formula (I).

Twelve μL per well of substrate solution containing glycogen (4.32 mg/mL), 21.6 mM UDP-glucose, 21.6 mM phospho(enol)pyruvate and 2.7 mM NADH in 30 mM glycylglycine, pH 7.3 buffer was added into a polystyrene 384-well assay plate (BD Biosciences). Compound solution (8 μL/well) at various concentrations (0-57 μM) in 30 mM glycylglycine, pH 7.3, 40 mM KCl, 20 mM MgCl2 plus 9.2% DMSO were added to the assay plate (columns 5-24). Enzyme solution (12 μL/well) containing glycogen synthase (16.88 μg/mL), pyruvate kinase (0.27 mg/mL), lactate dehydrogenase (0.27 mg/mL) in 50 mM Tris-HCl, pH 8.0, 27 mM DTT and bovine serum albumin (BSA, 0.2 mg/mL) was added to the assay plate (columns 3-24). As a blank control, enzyme solution without glycogen synthase was added into the top half wells of columns 1-2. To the bottom half wells of columns 1-2 were added a known activator, glucose 6-phosphate (18.9 mM) in addition to the enzyme solution. The reaction mixture was incubated at 37° C. The assay plate was then read for absorbance at 340 nm on a Tecan Ultra reader every 3 minutes up to a total of 30 minutes.

The enzyme activity (with or without compound) was calculated by the reaction rate and represented by the optical density change (ΔOD) per minute. Percent stimulation of glycogen synthase activity by a compound at various concentrations was calculated by the following formula:

% stimulation=100*$Rs/Rt$, where Rs is the reaction rate of the enzyme in the presence of compound and Rt is the reaction rate of the enzyme in the absence of compound.

SC2.0 is defined as the compound concentration that is needed to stimulate 200% of the enzyme activity.

The compounds of the examples exhibit SC2.0 activities of less than 30 μM.

It should be understood, of course, that the foregoing relates to preferred embodiments of the invention and that modifications may be made without departing from the spirit and scope of the invention as set forth in the following claims.

What is claimed is:

1. A compound of formula (I)

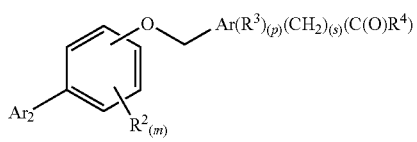

wherein

Ar is an aromatic heterocyclic ring selected from a thiazolyl or pyridinyl ring;

$Ar_2$ is a substituted or unsubstituted cyclic ring selected from the group consisting of benzo[1,3]dioxol-5-yl, furan-2-yl, isoquinolin-5-yl, isoxazol-4-yl, 1-naphthyl, pyrazol-1-yl, pyrazol-4-yl, pyridin-3-yl, thiophen-2-yl, thiophen-3-yl and phenyl and where substituted the substituents are selected from the group consisting of acetamido, aminocarbonyl, benzyl, benzyloxy, halogen, hydroxyl-lower alkyl, lower alkyl, lower alkoxy-lower alkyl, phenoxy, phenyl, lower alkoxy and trifluoromethoxy;

$R^2$ and $R^3$ are independently selected from the group consisting of lower alkyl, lower alkoxy, trifluoromethyl, halogen, hydroxy, amino, alkylamino, diakylamino, cyano and nitro;

$R^4$ is hydroxy or an amino acid attached through a nitrogen atom of the amino acid;

m is 0,1,2, 3 or 4;

p is 0, 1 or 2, and s is 0, 1, or 2, provided that when $Ar_2$ is phenyl, the phenyl ring is substituted by at least one substituent selected from the group consisting of acetamido, aminocarbonyl, benzloxy, hydroxyl-lower alkyl, lower-alkoxy-lower alkyl, phenoxy, phenyl, pyrazol-1-yl and trifluoromethoxy and when $Ar_2$ is substituted phenyl, there are not two lower alkyl substituents ortho to the point of attachment of the $Ar_2$ ring to the adjacent phenyl ring or a pharmaceutically acceptable salt thereof.

2. The compound of claim 1 wherein $Ar_2$ is phenyl substituted in the meta position by acetamido, aminocarbonyl or hydroxymethyl.

3. The compound of claim 1 wherein $Ar_2$ is pyridin-3-yl.

4. The compound of claim 3 wherein the pyridin-3-yl is substituted by halogen.

5. The compound of claim 1 wherein $Ar_2$ is phenyl substituted in the ortho position by trifluoromethoxy.

6. The compound of claim 1 wherein $Ar_2$ is phenyl substituted in the ortho position by methoxymethyl, benzyloxy or phenoxy.

7. The compound of claim 1 wherein $Ar_2$ is 1-naphthyl.

8. The compound of claim 1 wherein $Ar_2$ is benzo[1,3]dioxol-5-yl.

9. The compound of claim 1 wherein $Ar_2$ is thiophen-3-yl.

10. A compound of claim 1 having the formula

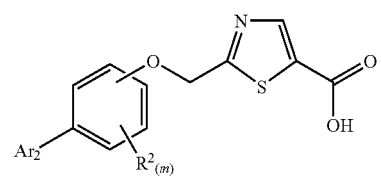

wherein $Ar_2$ is a substituted or unsubstituted cyclic ring selected from the group consisting of benzo[1,3]dioxol-5-yl, furan-2-yl, isoquinolin-5-yl, isoxazol-4-yl, 1-naphthyl, pyrazol-1-yl, pyrazol-4-yl, pyridin-3-yl, thiophen-2-yl, thiophen-3-yl and phenyl and where substituted the substituents are selected from the group consisting of acetamido, aminocarbonyl, benzyl, benzyloxy, halogen, hydroxyl-lower alkyl, lower alkyl, lower alkoxy-lower alkyl, phenoxy, phenyl, lower alkoxy and trifluoromethoxy;

$R^2$ is selected from the group consisting of lower alkyl, lower alkoxy, trifluoromethyl, halogen, hydroxy, amino, alkylamino, diakylamino, cyano and nitro;

provided that when $Ar_2$ is phenyl, the phenyl ring is substituted by at least one substituent selected from the group consisting of acetamido, aminocarbonyl, benzloxy, hydroxyl-lower alkyl, lower-alkoxy-lower alkyl, phenoxy, phenyl, pyrazol-1-yl and trifluoromethoxy and when Ar₂ is substituted phenyl, there are not two lower alkyl substituents ortho to the point of attachment of the Ar₂ ring to the adjacent phenyl ring;

m is 0,1,2,3 or 4 or a pharmaceutically acceptable salt thereof.

11. A compound of claim 1 having the formula

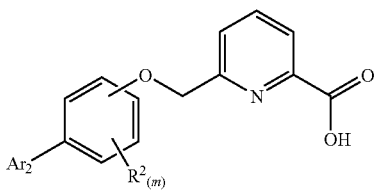

wherein

Ar₂ is a substituted or unsubstituted cyclic ring selected from the group consisting of benzo[1,3]dioxol-5-yl, furan-2-yl, isoquinolin-5-yl, isoxazol-4-yl, 1-naphthyl, pyrazol-1-yl, pyrazol-4-yl, pyridin-3-yl, thiophen-2-yl, thiophen-3-yl and phenyl and where substituted the substituents are selected from the group consisting of acetamido, aminocarbonyl, benzyl, benzyloxy, halogen, hydroxyl-lower alkyl, lower alkyl, lower alkoxy-lower alkyl, phenoxy, phenyl, lower alkoxy and trifluoromethoxy;

$R^2$ is selected from the group consisting of lower alkyl, lower alkoxy, trifluoromethyl, halogen, hydroxy, amino, alkylamino, diakylamino, cyano and nitro;

provided that when Ar₂ is phenyl, the phenyl ring is substituted by at least one substituent selected from the group consisting of acetamido, aminocarbonyl, benzyloxy, hydroxyl-lower alkyl, lower-alkoxy-lower alkyl, phenoxy, phenyl, pyrazol-1-yl and trifluoromethoxy and when Ar₂ is substituted phenyl, there are not two lower alkyl substituents ortho to the point of attachment of the Ar₂ ring to the adjacent phenyl ring;

m is 0,1,2,3 or 4 or a pharmaceutically acceptable salts thereof.

12. A compound selected from the group consisting of 2-(3'-Acetylamino-biphenyl-4-yloxymethyl)- thiazole-4-carboxylic acid;

2-(4-Benzo[1,3]dioxol-5-yl-phenoxymethyl)- thiazole-4-carboxylic acid;

2-(2'-Benzyloxy-biphenyl-4-yloxymethyl)- thiazole-4-carboxylic acid;

2-[4-(1-Benzyl-1 H-pyrazol-4-yl)- phenoxymethyl]-thiazole-4-carboxylic acid;

([1,1';3',1'']Terphenyl-4-yloxymethyl) -thiazole-4-carboxylic acid;

2-(3'-Carbamoyl-biphenyl-4-yloxymethyl) -thiazole-4-carboxylic acid;

2-[4-(2-Chloro-pyridin-3-yl) -phenoxymethyl]-thiazole-4-carboxylic acid;

2-[4-(6-Fluoro-pyridin-3-yl) -phenoxymethyl]-thiazole-4-carboxylic acid;

2-(3'-Hydroxymethyl-biphenyl-4-yloxymethyl) -thiazole-4-carboxylic acid;

2-(4-Isoquinolin-5-yl-phenoxymethyl) -thiazole-4-carboxylic acid;

2-(2'-Methoxymethyl-biphenyl-4-yloxymethyl) -thiazole-4-carboxylic acid;

2-(3'-Methoxymethyl-biphenyl-4-yloxymethyl) -thiazole-4-carboxylic acid;

2-(4-Naphthalen-1-yl-phenoxymethyl) -thiazole-4-carboxylic acid;

2-(2'-Phenoxy-biphenyl-4-yloxymethyl) -thiazole-4-carboxylic acid;

2-(4-Thiophen-3-yl-phenoxymethyl) -thiazole-4-carboxylic acid;

2-(2'-Trifluoromethoxy-biphenyl-4-yloxymethyl) -thiazole-4-carboxylic acid;

6-(4-Benzo[1,3]dioxol-5-yl-phenoxymethyl) -pyridine-2-carboxylic acid;

6-(2'-Methoxymethyl-biphenyl-4-yloxymethyl) -pyridine-2-carboxylic acid; and 6-(4-Thiophen-2-yl-phenoxymethyl) -pyridine-2-carboxylic acid.

13. A pharmaceutical composition comprising a compound of the formula

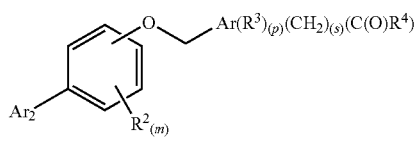

wherein

Ar is an aromatic heterocyclic ring selected from a thiazolyl or pyridinyl ring;

Ar₂ is a substituted or unsubstituted cyclic ring selected from the group consisting of benzo[1,3]dioxol-5-yl, furan-2-yl, isoquinolin-5-yl, isoxazol-4-yl, 1-naphthyl, pyrazol-1-yl, pyrazol-4-yl, pyridin-3-yl, thiophen-2-yl, thiophen-3-yl and phenyl and where substituted the substituents are selected from the group consisting of acetamido, aminocarbonyl, benzyl, benzyloxy, halogen, hydroxyl-lower alkyl, lower alkyl, lower alkoxy-lower alkyl, phenoxy, phenyl, lower alkoxy and trifluoromethoxy;

$R^2$ and $R^3$ are independently selected from the group consisting of lower alkyl, lower alkoxy, trifluoromethyl, halogen, hydroxy, amino, alkylamino, diakylamino, cyano and nitro;

$R^4$ is hydroxy or an amino acid attached through a nitrogen atom of the amino acid;

m is 0,1,2,3 or 4;

p is 0, 1 or 2, and s is 0, 1 or 2 or a pharmaceutically acceptable salt thereof, provided that when Ar₂ is phenyl, the phenyl ring is substituted by at least one substituent selected from the group consisting of acetamido, aminocarbonyl, benzloxy, hydroxyl-lower alkyl, lower-alkoxy-lower alkyl, phenoxy, phenyl, pyrazol-1-yl and trifluoromethoxy and when Ar₂ is substituted phenyl, there are not two lower alkyl substituents ortho to the point of attachment of the Ar₂ ring to the adjacent phenyl ring, together with a pharmaceutically acceptable carrier and/or excipient.

* * * * *

UNITED STATES PATENT AND TRADEMARK OFFICE
CERTIFICATE OF CORRECTION

PATENT NO. : 7,524,870 B2
APPLICATION NO. : 11/283925
DATED : April 28, 2009
INVENTOR(S) : Paul Gillespie, Robert Alan Goodnow, Jr. and Jefferson Wright Tilley Page 1 of 1

It is certified that error appears in the above-identified patent and that said Letters Patent is hereby corrected as shown below:

In Claim 12 at Column 75, Line 51, please delete -

"([1,1';3',1"]Terphenyl-4-yloxymethyl)-thiazole-4-carboxylic acid;"
and insert

--2-([1,1';3',1"]Terphenyl-4-yloxymethyl)-thiazole-4-carboxylic acid;--

Signed and Sealed this

Ninth Day of June, 2009

JOHN DOLL
*Acting Director of the United States Patent and Trademark Office*